United States Patent
Konishi et al.

(10) Patent No.: US 9,187,771 B2
(45) Date of Patent: Nov. 17, 2015

(54) PHENYLPYRUVATE REDUCTASE AND METHOD FOR MANUFACTURING OPTICALLY-ACTIVE PHENYLLACTIC ACID AND 4-HYDROXYL-PHENYLLACTIC ACID USING SAME ENZYME

(75) Inventors: Kazunobu Konishi, Tokyo (JP); Naoki Takaya, Ibaraki (JP)

(73) Assignee: Asahi Kasei Chemicals Corporation, Tokyo (JP)

( * ) Notice: Subject to any disclaimer, the term of this patent is extended or adjusted under 35 U.S.C. 154(b) by 92 days.

(21) Appl. No.: 13/981,832

(22) PCT Filed: Jan. 30, 2012

(86) PCT No.: PCT/JP2012/051989
§ 371 (c)(1),
(2), (4) Date: Oct. 11, 2013

(87) PCT Pub. No.: WO2012/105495
PCT Pub. Date: Aug. 9, 2012

(65) Prior Publication Data
US 2014/0073024 A1 Mar. 13, 2014

(30) Foreign Application Priority Data

Jan. 31, 2011 (JP) .................................. 2011-018892
Jan. 31, 2011 (JP) .................................. 2011-018895

(51) Int. Cl.
C12P 7/42 (2006.01)
C12N 9/02 (2006.01)
C12N 1/20 (2006.01)
C12N 9/04 (2006.01)
C12R 1/645 (2006.01)
A23L 1/03 (2006.01)

(52) U.S. Cl.
CPC ................ *C12P 7/42* (2013.01); *A23L 1/0315* (2013.01); *C12N 9/0006* (2013.01); *C12R 1/645* (2013.01); *C12Y 101/01237* (2013.01)

(58) Field of Classification Search
None
See application file for complete search history.

(56) References Cited

U.S. PATENT DOCUMENTS 5,256,552 A 10/1993 Matsuyama et al.

FOREIGN PATENT DOCUMENTS

| EP | 1291417 A1 | 3/2003 |
|---|---|---|
| JP | 9-37792 | 2/1997 |
| JP | 2000-300284 | 10/2000 |
| JP | 2003-192633 | 7/2003 |
| WO | 01/81563 | 11/2001 |

OTHER PUBLICATIONS

Accession B9WAK9. Mar. 24, 2009.*
Chica et al. Curr Opin Biotechnol. Aug. 2005;16(4):378-84.*
Sen et al. Appl Biochem Biotechnol. Dec. 2007;143(3):212-23.*
Fauvart et al., "Identification of a novel glyoxylate reductase supports phylogeny-based enzymatic substrate specificity prediction," Biochimica et Biophysica Acta, 1774(9):1092-1098 (2007).
Fujii et al., "Novel fungal phenylpyruvate reductase belongs to d-isomer-specific 2-hydroxyacid dehydrogenase family," Biochimica et Biophysica Acta, 1814(12):1669-1676 (2011).
Wanmeng et al., "Characterization of d-lactate dehydrogenase from *Pediococcus acidilactici* that converts phenylpyruvic acid into phenyllactic acid," Biotechnology Letters, 34(5): 907-911 (2012).
Supplementary European Search Report issued in European Patent Application No. 12741920.8 dated Feb. 20, 2014.
Dieuleveux, Purification and Characterization of Anti-Listeria Compounds Produced by *Geotrichum candidum*, Applied and Environmental Microbiology, 64, pp. 800-803, 1998.
Mu, Production of 4-Hydroxyphenyllactic Acid by *Lactobacillus* sp, SK007 Fermentation, Journal of Bioscience and Bioengineering, 109, pp. 369-371, 2010.
Ohhira, Identification of 3-Phenyllactic Acid as a Possible Antibacterial Substance Produced by *Enterococcus* Facalis TH 10, Biocontrol Science, 9, pp. 77-81, 2004.
Dieuleveux, Antimicrobial Effects of D-3-Phenyllactic Acid on *Listeria monocytogenes* in TSB-YE Medium, Milk, and Cheese, Journal of Food Protection, 61, pp. 1281-1285, 1998.
Dieuleveux, Antimicrobial Spectrum and Target Site of D-3-Phenyllactic Acid, International Journal of Food Microbiology, 40, pp. 177-183, 1998.
Thierry, Production of Cheese Flavour Compounds Derived from Amino Acid Catabolism by *Propionibacterium freudenreichii*, Lait, 82, pp. 17-32, 2002.
Strom, *Lactobacillus plantarum* MiLAB 393 Produces the Antifungal Cyclic Dipeptides Cyclo(L-Phe-L-Pro) and Cyclo (L-Phe-trans-4-OH-L-Pro) and 3-Phenyllactic Acid, Applied Environmental Microbiology, 68, pp. 4322-4327, 2002.
Magnusson, Broad and Complex Antifungal Activity Among Environmental Isolates of Lactic Acid Bacteria, FEMS Microbiology Letters, 219, 129-135, 2003.
Valerio, Production of Phenyllactic Acid by Lactic Acid Bacterial: An Approach to the Selection of Strains Contributing to Food Quality and Preservation, FEMS Microbiology Letters, 233, pp. 289-295.
Li, Purification and Partial Characterization of *Lactobacillus* Species SK007 Lactate Dehydrogenase (LDH) Catalyzing Phenylpyruvic Acid (PPA) Conversion into Phenyllactic Acid (PLA), Journal of Agricultural and Food Chemistry, 56, pp. 2392-2399, 2008.
Jia, Bioconversion of Phenylpyruvate to Phenyllactate: Gene Cloning, Expression, and Enzymatic Characterization of D- and L1-Lactate Dehydrogenases from *Lactobacillus plantarum* SK002, Appl Biochem Biotechnol, 162, pp. 242-251, 2010.

(Continued)

*Primary Examiner* — Christian Fronda
(74) *Attorney, Agent, or Firm* — Morgan, Lewis & Bockius LLP

(57) ABSTRACT

The present invention provides a phenylpyruvate reductase for efficiently obtaining highly pure, optically active 3-phenyllactate and 4-hydroxyphenyllactate; a gene coding for the same; and a method for manufacturing optically active 3-phenyllactate and 4-hydroxyphenyllactate employing the same.

8 Claims, 16 Drawing Sheets

(56) References Cited

OTHER PUBLICATIONS

Ishikura, Recognition Site for the Side Chain of 2-Ketoacid Substrate in D-Lactate Dehydrogenase, J. Biochem., 138, pp. 741-749, 2005.

Lavermicocca, Purification and Characterization of Novel Antifungal Compounds from the Sourdough *Lactobacillus plantarum* Strain 21B, Appl. Enviorn. Microbiol. 66, pp. 4084-4090, 2000.

International Search Report for PCT/JP2012/051989 dated Apr. 24, 2012.

Notice of Allowance issued in counterpart Korean Patent Application No. 10-2013-7019832 dated May 22, 2015.

\* cited by examiner

Vegetative cells of Strain TK1

FIG. 12
(a)
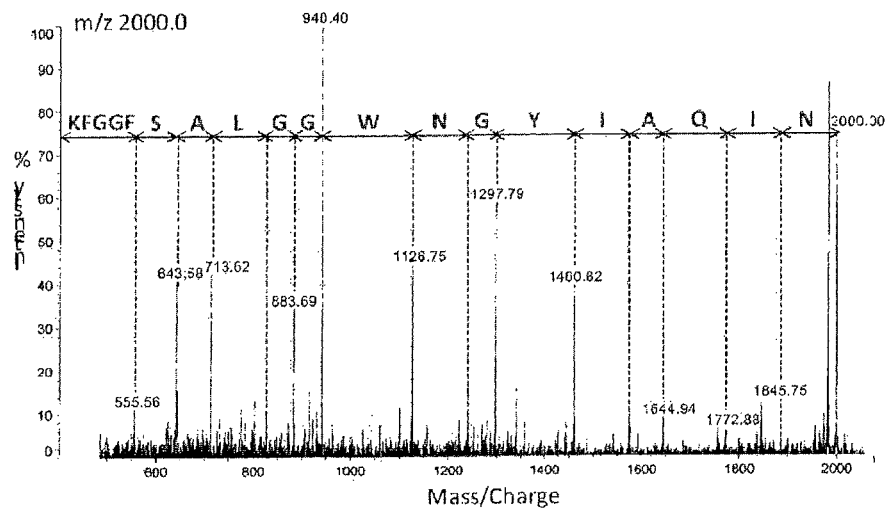
(b)
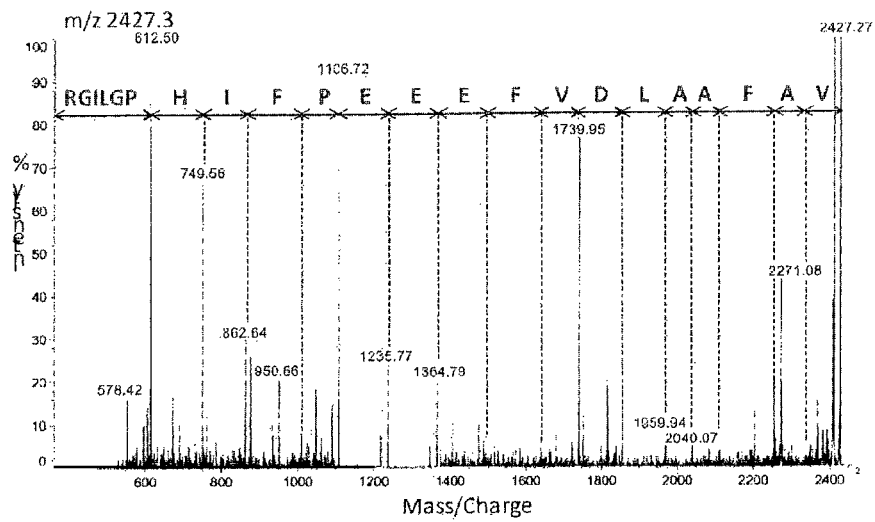

FIG. 14

```
         10        20        30        40        50        60        70        80        90
ATGAAAAAGCCTCAGGTTCCTTATACTTGGAAGAATAAAGGAATCCTTGCCGAATACGTTTCATTCCAAACTAAGTTTGAATGCATTCGC
 M  K  K  P  Q  V  L  I  L  G  R  I  K  E  S  L  P  E  Y  V  S  F  Q  T  K  F  E  C  I  R 100       110       120       130       140       150       160       170       180
TATACTGCATCTTCAGTAGATCAGCTAATCAAGGACTTCTCATCTAGTTTACGTAATATACAGGCTATATATGGTAACTGGGGAGGACTC
 Y  T  A  S  S  V  D  Q  L  I  K  D  F  S  S  S  L  R  N  I  Q  A  I  Y  G  N  W  G  G  L 190       200       210       220       230       240       250       260       270
GCCTCATTTGGTGGCTTCAAAGGCAAGTTATTGGAGGCAGCACCTCGTAGTTTAAAAATTATTGCAATTTGTCAGGTTGGCTATGATGAG
 A  S  F  G  G  F  K  G  K  L  L  E  A  A  P  R  S  L  K  I  I  A  I  C  Q  V  G  Y  D  E 280       290       300       310       320       330       340       350       360
TTTGATTTAGCCGCGATGAAAGAACGTGGAATTATTTTAACCAATGTCCCTACTCCATTGGCATTTGAAGCAGTTGCAGACTTGGTTTTG
 F  D  L  A  A  M  K  E  R  G  I  I  L  T  N  V  P  T  P  L  A  F  E  A  V  A  D  L  V  L 370       380       390       400       410       420       430       440       450
TACAATACGTTGATGGCATTTAGAAATTTCAAACTTTACCAGAATAATATGAGCCCTACCCTTAATAACACCAACCTTTTTAAGAAATCA
 Y  N  T  L  M  A  F  R  N  F  K  L  Y  E  N  N  M  S  P  T  L  N  N  T  N  L  L  R  N  S 460       470       480       490       500       510       520       530       540
TTGGTCAATGGTCAGTTTGATCAACAAACAGGAAAATGCATCGTCCCTCCTATAGTGGGATGTGCCTTTCCCACTCTGTGTGAGAGA
 L  V  N  G  Q  F  D  Q  E  T  G  K  C  I  V  P  P  I  V  G  C  A  F  A  D  S  V  C  E  R 550       560       570       580       590       600       610       620       630
GAAAACTTATCCCCAAGGGGTCATAATGCTGTTATAATACGATTTGGAAGAATTGGAAAGTTGGCAGCGCAACGCTTAAATGCAATTGGC
 E  N  L  S  P  R  G  H  N  A  V  I  I  G  F  G  R  I  G  K  L  A  A  Q  R  L  N  A  I  G 640       650       660       670       680       690       700       710       720
ATGAATATTCATTATGTCAAAAGAACCCAGTGTTCTCCAGAGGTGGAACAGGAACTCTCTTTCCTGTTACTTACCACAAGTCAATTGAA
 M  N  I  H  Y  V  K  R  T  Q  C  S  P  E  V  E  Q  E  L  S  F  P  V  T  Y  H  K  S  I  E 730       740       750       760       770       780       790       800       810
CAAGCTGGCCGCATAGCTGACTTGTTGGTTATTTGCTGTCCTGGAACACCGTCCACTAAACATTTGATCAATTCTGATACTTTGGACAAA
 E  A  G  R  I  A  D  L  L  V  I  C  C  P  G  T  P  S  T  K  H  L  I  N  S  D  T  L  D  K 820       830       840       850       860       870       880       890       900
ATGGAGAAGCAAATTAGAATTATTAATATTGGACGTGGTACAGTTATTGATGAAAATGCGTTAGTATGTGGATTAAAATCTGACAAAGTT
 M  E  K  Q  I  R  I  I  N  I  G  R  G  T  V  I  D  E  N  A  L  V  C  G  L  K  S  D  K  V 910       920       930       940       950       960       970       980       990
GCCTTTGCTGCTTTGGATGTGTTTGAAGAAGAACCTTTTATACATCCAGGTTTAATCGGTAGGCAAGATGTACATTTAACTCCACATATT
 A  F  A  A  L  D  V  F  E  E  E  P  F  I  H  P  G  L  I  G  R  Q  D  V  H  L  T  P  H  I 1000      1010      1020      1030      1040      1050      1060      1070      1080
GGTTCATCTACAAGTGAGCTTTTTAACTACACTGCAAAGCAAGCTATGCAAAATATTTCTACGGCTTTGTATAACACAAACGAAGAAATG
 G  S  S  T  S  E  L  F  N  Y  T  A  K  Q  A  M  Q  N  I  S  T  A  L  Y  N  T  N  E  E  M 1090      1100      1110      1120      1130      1140      1150      1160      1170
AATCTTGTAGTTTGAGCTTATATCCAAATTACTTTATTTGTATTTTAATCATAATGTTTCATTTTTTATAAAAAAAAAAAAAAAAAA
 N  L  V  V  *
```

FIG. 15
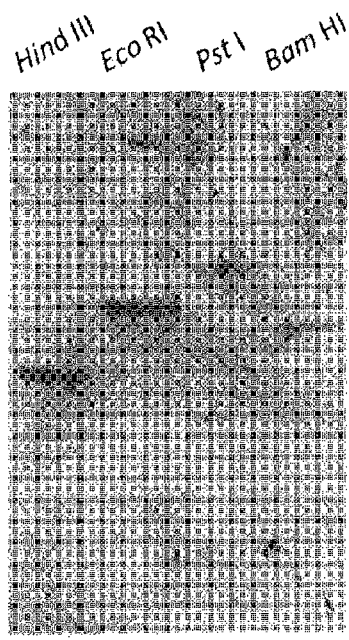
FIG. 16
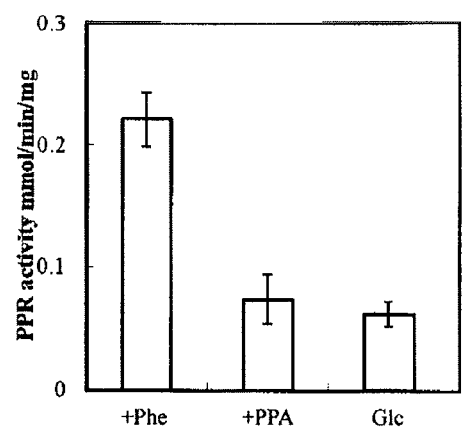 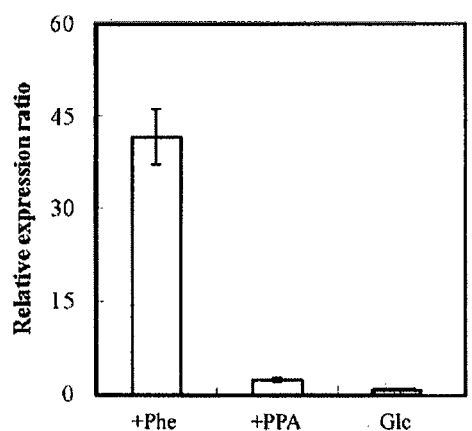

FIG. 18

```
            : ::          :                              .  .      .  :.
WfPPR  -MKKPQVLILGRIKESLPEYVSFQTKFECIRYTASSVDQLIKDFSSSLRNIQAIYGNWGGLASFGGFKGKLLEAAPRSLK   79
CdHDH  MTIKQKVLFLE--KPNVEDLKQFEAKFDCIYYTLSTLEQLLIDFQTSLQDVEAIYCGWNGFGMFGGFRGKVLAHAPQSLR   78
EcGXR  --MKFSVILYK----ALPDDLLQRLQEHFTVHQVANLSPQTVEQNAAIFAEAEGLLGSN-----ENVNAALLEKMPK-LR   68
SsHPPR -MEAIGVLMMC----PMSTYLEQELDKRFKLPRYWTQPAQRDFLALQAESIRAVVGNSN-----AGADAELIDALPK-LE   69
LpDLDH ----MKIIAYA-----VRDDERPFFDTWMKENPDVEVKLVPELLTEDNVDLAKGFDGADVYQQKDYTAEVLNKLADEGVK   71

:  .**  *  .*:       :  :  :  :.*         : :*:  :    :    *.       :  :
WfPPR  IIAICQVGYDEFDLAAMKERGIILTNVPTPLAFEAVADLVLYNTLMAFRNFKLYENNMSPTLN-NTNLLRNSLVNGQFDQ  158
CdHDH  IVATCSVGYDGFDIERMSERNIVLTNVPSPLAFEAVADLALYNAINSFRNFKLYAENLSSNQYGHSGVSRTSMLHGNFPDQ 158
EcGXR  ATSTISVGYDNFDVDALTARKILLMHTPT-VLTETVADTLMALVLSTARRVVRVAERVK--------------AGEWTA  132
SsHPPR IVSSPSVGLDKVDLIKCEEKGVRVTNTPD-VLTDDVADLAIGLILAVLRRICECDKYVR---------------RGANK- 132
LpDLDH NISLRNVSVDMLDVPTVKARGLNISNVPA-YSPNAIAELSVTQLMQLLRQTPLFNKKLA----------------KQDF  133

.                 .                : :  *:*                 :.  :
WfPPR  RTGKCIVPPIVGCAFADSVCERENLSPRGHNAVIIGFGRIGKLAAQRLNA-IGMNIHYVKRTQCSPEVEQELSFPVTYHK  237
CdHDH  SSGKAIVEPVVGHTYGYACCKRDNLSPRGHNAVIVGPGHIGELIGRRLAC-IGMNVHYVKRTRLSESQEKSLGYEVTYHE  237
EcGXR  SIGPDWYG--------------TDVHHKTLGIVGMGRIGMALAQRAHFGFNMPILYNARRHHKEARERFN----ARYC   192
SsHPPR -FGDFKLT--------------TKFSGKRVGIIGLGRIGLAVAERAKA-FDCPISYFSRSKKPNTNYTY--------YG  187
LpDLDH RWAPDIAK--------------BLNTMTVGVIGTGRIGRAAIDIFKG-FGAKVIGYDVYRNAELEKEG-----MYVD  190

:        :*. :    *     ..  *:;. : .    : : **   :*. *:  , ...:  *,**.:* *.
WfPPR  SIEEAGRIADLLVICCCPGTPSTKHLINSDTLDKMEKQIRIINIGHGTVIDENALVCGLKSDKVAFAALDVFEESPF----  313
CdHDH  SLEETKDIADLIIACPGTPSTRHMINKQLINSMGKPFRIINIGHGFVIDEDALVGGGLKSGKVLFAGLDVFENSPT----  313
EcGXR  DLDTLLQESDFVCLILPLTDETHHLFGAEQFAKMKSSAIFINAGHGPVVDENALIAALQKGEIHAAGLDVFEQSPLS---  269
SsHPPR SVVELASNSDILVVACPLTPETTHIINREVIDALGFKGVLINIGHGPHVDEPELVSALVEGRLGGAGLDVFENSPE----  263
LpDLDH TLDELYAQADVITLHVPALKDNYHMLNADAFSKMKDGAYILNFARGTLIDSEDLIKALDSGKVAGAALDTYEYETKIFNK  270

: *:.  :* **  .         .          :                :
WfPPR  ---------IHPGLIGRQDVHLTPHIGESTSELFNYTAKQAMQNISTALYNTNEEMNLVV----  364
CdHDH  ---------IHPGLLGRDDVVLTPHIGSGIAENYRFIALTSMRNIETILRGYDEKINRVN----  364
EcGXR  ---------VDSPLLSMAHVVAVPHIGSATHETRYGMAACAVDNLIDALQGKVEKNCVNPHVAD 324
SsHPPR ---------VPEKLFGLENVVLLPHVGSGTVETRKVMADLVGNLEAHFSGKPLLTFVV-----  313
LpDLDH DLEGQTIDDKVFMNLFNRDNVLITPHTAFYTETAVHNMVHVSMNSNKQFIETGKADTQVKFD--- 332
```

FIG. 19

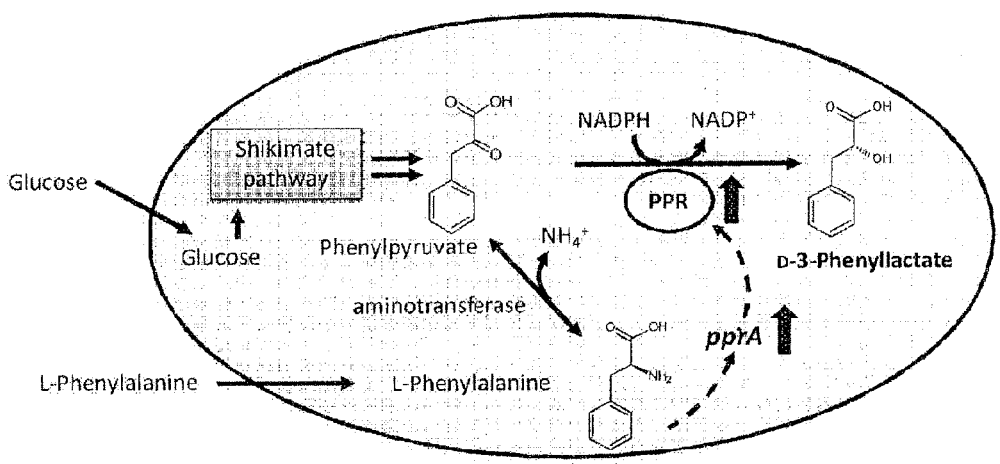

```
                        SEQUENCE LISTING

<160> NUMBER OF SEQ ID NOS: 30

<210> SEQ ID NO 1
<211> LENGTH: 12
<212> TYPE: PRT
<213> ORGANISM: Wickerhamia fluorescens

<400> SEQUENCE: 1

Met Lys Lys Pro Gln Val Leu Ile Leu Gly Arg Ile
1               5                   10

<210> SEQ ID NO 2
<211> LENGTH: 19
<212> TYPE: PRT
<213> ORGANISM: Wickerhamia fluorescens

<400> SEQUENCE: 2

Asn Ile Gln Ala Ile Tyr Gly Asn Trp Gly Gly Leu Ala Ser Phe Gly
1               5                   10                  15

Gly Phe Lys

<210> SEQ ID NO 3
<211> LENGTH: 22
<212> TYPE: PRT
<213> ORGANISM: Wickerhamia fluorescens

<400> SEQUENCE: 3

Val Ala Phe Ala Ala Leu Asp Val Phe Glu Glu Pro Phe Ile His
1               5                   10                  15

Pro Gly Leu Ile Gly Arg
            20

<210> SEQ ID NO 4
<211> LENGTH: 364
<212> TYPE: PRT
<213> ORGANISM: Wickerhamia fluorescens

<400> SEQUENCE: 4

Met Lys Lys Pro Gln Val Leu Ile Leu Gly Arg Ile Lys Glu Ser Leu
1               5                   10                  15
```

| | | | | | | | | | | | | |
|---|---|---|---|---|---|---|---|---|---|---|---|---|
|Pro|Glu|Tyr|Val|Ser|Phe|Gln|Thr|Lys|Phe|Glu|Cys|Ile|Arg|Tyr|Thr|
| | |20| | | |25| | | |30| | | | | |

```
Pro Glu Tyr Val Ser Phe Gln Thr Lys Phe Glu Cys Ile Arg Tyr Thr
             20              25              30

Ala Ser Ser Val Asp Gln Leu Ile Lys Asp Phe Ser Ser Leu Arg
         35              40              45

Asn Ile Gln Ala Ile Tyr Gly Asn Trp Gly Gly Leu Ala Ser Phe Gly
 50              55              60

Gly Phe Lys Gly Lys Leu Leu Glu Ala Ala Pro Arg Ser Leu Lys Ile
65              70              75              80

Ile Ala Ile Cys Gln Val Gly Tyr Asp Glu Phe Asp Leu Ala Ala Met
             85              90              95

Lys Glu Arg Gly Ile Ile Leu Thr Asn Val Pro Thr Pro Leu Ala Phe
         100             105             110

Glu Ala Val Ala Asp Leu Val Leu Tyr Asn Thr Leu Met Ala Phe Arg
         115             120             125

Asn Phe Lys Leu Tyr Glu Asn Asn Met Ser Pro Thr Leu Asn Asn Thr
130             135             140

Asn Leu Leu Arg Asn Ser Leu Val Asn Gly Gln Phe Asp Gln Glu Thr
145             150             155             160

Gly Lys Cys Ile Val Pro Pro Ile Val Gly Cys Ala Phe Ala Asp Ser
             165             170             175

Val Cys Glu Arg Glu Asn Leu Ser Pro Arg Gly His Asn Ala Val Ile
         180             185             190

Ile Gly Phe Gly Arg Ile Gly Lys Leu Ala Ala Gln Arg Leu Asn Ala
         195             200             205

Ile Gly Met Asn Ile His Tyr Val Lys Arg Thr Gln Cys Ser Pro Glu
         210             215             220

Val Glu Gln Glu Leu Ser Phe Pro Val Thr Tyr His Lys Ser Ile Glu
225             230             235             240

Glu Ala Gly Arg Ile Ala Asp Leu Leu Val Ile Cys Cys Pro Gly Thr
             245             250             255

Pro Ser Thr Lys His Leu Ile Asn Ser Asp Thr Leu Asp Lys Met Glu
         260             265             270

Lys Gln Ile Arg Ile Ile Asn Ile Gly Arg Gly Thr Val Ile Asp Glu
         275             280             285

Asn Ala Leu Val Cys Gly Leu Lys Ser Asp Lys Val Ala Phe Ala Ala
         290             295             300

Leu Asp Val Phe Glu Glu Pro Phe Ile His Pro Gly Leu Ile Gly
305             310             315             320

Arg Gln Asp Val His Leu Thr Pro His Ile Gly Ser Thr Ser Glu
             325             330             335

Leu Phe Asn Tyr Thr Ala Lys Gln Ala Met Gln Asn Ile Ser Thr Ala
         340             345             350

Leu Tyr Asn Thr Asn Glu Glu Met Asn Leu Val Val
         355             360
```

<210> SEQ ID NO 5
<211> LENGTH: 1095
<212> TYPE: DNA
<213> ORGANISM: Wickerhamia fluorescens
<220> FEATURE:
<221> NAME/KEY: CDS
<222> LOCATION: (1)..(1095)

<400> SEQUENCE: 5

```
atg aaa aag cct cag gtc ctt ata ctt gga aga ata aag gaa tcc ttg    48
Met Lys Lys Pro Gln Val Leu Ile Leu Gly Arg Ile Lys Glu Ser Leu
```

```
                                                        -continued
1               5                    10                   15
ccc gaa tac gtt tca ttc caa act aag ttt gaa tgc att cgc tat act      96
Pro Glu Tyr Val Ser Phe Gln Thr Lys Phe Glu Cys Ile Arg Tyr Thr
             20                   25                  30 gca tct tca gta gat cag cta atc aag gac ttc tca tct agt tta cgt     144
Ala Ser Ser Val Asp Gln Leu Ile Lys Asp Phe Ser Ser Ser Leu Arg
         35                   40                  45 aat ata cag gct ata tat ggt aac tgg gga gga ctc gcc tca ttt ggt     192
Asn Ile Gln Ala Ile Tyr Gly Asn Trp Gly Gly Leu Ala Ser Phe Gly
50                   55                  60 ggc ttc aaa ggc aag tta ttg gag gca gca cct cgt agt tta aaa att     240
Gly Phe Lys Gly Lys Leu Leu Glu Ala Ala Pro Arg Ser Leu Lys Ile
65                   70                  75                  80 att gca att tgt cag gtt ggg tat gat gag ttt gat tta gcc gcg atg     288
Ile Ala Ile Cys Gln Val Gly Tyr Asp Glu Phe Asp Leu Ala Ala Met
                 85                  90                  95 aaa gaa cgt gga att att tta acc aat gtc cct act cca ttg gca ttt     336
Lys Glu Arg Gly Ile Ile Leu Thr Asn Val Pro Thr Pro Leu Ala Phe
             100                  105                 110 gaa gca gtt gca gac ttg gtt ttg tac aat acg ttg atg gca ttt aga     384
Glu Ala Val Ala Asp Leu Val Leu Tyr Asn Thr Leu Met Ala Phe Arg
         115                  120                 125 aat ttc aaa ctt tac gag aat aat atg agc cct acc ctt aat aac acc     432
Asn Phe Lys Leu Tyr Glu Asn Asn Met Ser Pro Thr Leu Asn Asn Thr
130                  135                 140 aac ctt tta aga aat tca ttg gtc aat ggt cag ttt gat caa gaa aca     480
Asn Leu Leu Arg Asn Ser Leu Val Asn Gly Gln Phe Asp Gln Glu Thr
145                  150                 155                 160 gga aaa tgc atc gtc cct cct ata gtg gga tgt gcc ttt gcc gac tct     528
Gly Lys Cys Ile Val Pro Pro Ile Val Gly Cys Ala Phe Ala Asp Ser
                 165                 170                 175 gtg tgt gag aga gaa aac tta tcc cca agg ggt cat aat gct gtt ata     576
Val Cys Glu Arg Glu Asn Leu Ser Pro Arg Gly His Asn Ala Val Ile
             180                 185                 190 ata gga ttt gga aga att gga aag ttg gca gcg caa cgc tta aat gca     624
Ile Gly Phe Gly Arg Ile Gly Lys Leu Ala Ala Gln Arg Leu Asn Ala
         195                 200                 205 att ggc atg aat att cat tat gtc aaa aga acc cag tgt tct cca gag     672
Ile Gly Met Asn Ile His Tyr Val Lys Arg Thr Gln Cys Ser Pro Glu
210                 215                 220 gtg gaa cag gaa ctc tct ttt cct gtt act tac cac aag tca att gaa     720
Val Glu Gln Glu Leu Ser Phe Pro Val Thr Tyr His Lys Ser Ile Glu
225                 230                 235                 240 gaa gct ggc cgc ata gct gac ttg ttg gtt att tgc tgt cct gga aca     768
Glu Ala Gly Arg Ile Ala Asp Leu Leu Val Ile Cys Cys Pro Gly Thr
                 245                 250                 255 ccg tcc act aaa cat ttg atc aat tct gat act ttg gac aaa atg gag     816
Pro Ser Thr Lys His Leu Ile Asn Ser Asp Thr Leu Asp Lys Met Glu
             260                 265                 270 aag caa att aga att att aat att gga cgt ggt aca gtt att gat gaa     864
Lys Gln Ile Arg Ile Ile Asn Ile Gly Arg Gly Thr Val Ile Asp Glu
         275                 280                 285 aat gcg tta gta tgt gga tta aaa tct gac aaa gtt gcc ttt gct gct     912
Asn Ala Leu Val Cys Gly Leu Lys Ser Asp Lys Val Ala Phe Ala Ala
290                 295                 300 ttg gat gtg ttt gaa gaa gaa cct ttt ata cat cca ggt tta atc ggt     960
Leu Asp Val Phe Glu Glu Glu Pro Phe Ile His Pro Gly Leu Ile Gly
305                 310                 315                 320 agg caa gat gta cat tta act cca cat att ggt tca tct aca agt gag    1008
Arg Gln Asp Val His Leu Thr Pro His Ile Gly Ser Ser Thr Ser Glu
```

```
Arg Gln Asp Val His Leu Thr Pro His Ile Gly Ser Ser Thr Ser Glu
            325                 330                 335 ctt ttt aac tac act gca aag caa gct atg caa aat att tct acg gct    1056
Leu Phe Asn Tyr Thr Ala Lys Gln Ala Met Gln Asn Ile Ser Thr Ala
        340                 345                 350 ttg tat aac aca aac gaa gaa atg aat ctt gta gtt tga                1095
Leu Tyr Asn Thr Asn Glu Glu Met Asn Leu Val Val
        355                 360
```

```
<210> SEQ ID NO 6
<211> LENGTH: 20
<212> TYPE: DNA
<213> ORGANISM: Wickerhamia fluorescens
<220> FEATURE:
<223> OTHER INFORMATION: conserved-1

<400> SEQUENCE: 6
ataggatttg gaagaattgg                                                 20

<210> SEQ ID NO 7
<211> LENGTH: 20
<212> TYPE: DNA
<213> ORGANISM: Wickerhamia fluorescens
<220> FEATURE:
<223> OTHER INFORMATION: conserved-2

<400> SEQUENCE: 7
attaatattg gacgtggtac                                                 20

<210> SEQ ID NO 8
<211> LENGTH: 20
<212> TYPE: DNA
<213> ORGANISM: Wickerhamia fluorescens
<220> FEATURE:
<223> OTHER INFORMATION: specific-1

<400> SEQUENCE: 8
aataacacca accttttaag                                                 20

<210> SEQ ID NO 9
<211> LENGTH: 584
<212> TYPE: DNA
<213> ORGANISM: Wickerhamia fluorescens
<220> FEATURE:
<223> OTHER INFORMATION: TK1(FERM P-22048); rDNA-D1/D2

<400> SEQUENCE: 9
gcatatcaat aagcggagga aaagaaacca acagggattg cctcagtaac ggcgagtgaa     60
gcggcaaaag ctcaaatttg aaatctggta gtttcactat ccgaattgta atttgaagag    120
ataactttgg aattggctct tgtctatgtt ccttggaaca ggacgtcaca gagggtgaga    180
atcccgtgcg atgagatgac caattctatg taaagtattc tcgacgagtc gagttgtttg    240
ggaatgcagc tctaagtggg tggtaaattc catctaaagc taaatattgg cgagagaccg    300
atagcgaaca agtacagtga tggaaagatg aaaagaactt gaaaagaga gtgaaaaagt     360 acgtgaaatt gttgaaaggg aagggcttga gatcagactt ggtattgatt ttatctttac    420
tgggccagca tcggtttgta cggtgagata agacttattg gaaagtagct catctttttg    480
agtgttatag cctttagtga tgtcaccagt atagaccgag gactgcgatt ttatatcaag    540
gatgttggca taatgatctt aagccgcccg tcttgaaacg gacc                     584

<210> SEQ ID NO 10
```

```
<211> LENGTH: 17
<212> TYPE: DNA
<213> ORGANISM: Artificial sequence
<220> FEATURE:
<223> OTHER INFORMATION: primer NP
<220> FEATURE:
<221> NAME/KEY: misc_feature
<222> LOCATION: (12)..(12)
<223> OTHER INFORMATION: n is a, c, g, or t

<400> SEQUENCE: 10
atgaaraarc cncaggt                                                      17

<210> SEQ ID NO 11
<211> LENGTH: 20
<212> TYPE: DNA
<213> ORGANISM: Artificial sequence
<220> FEATURE:
<223> OTHER INFORMATION: Oligo dT

<400> SEQUENCE: 11
tttttttttt tttttttttt                                                   20

<210> SEQ ID NO 12
<211> LENGTH: 20
<212> TYPE: DNA
<213> ORGANISM: Artificial sequence
<220> FEATURE:
<223> OTHER INFORMATION: primer 2427P
<220> FEATURE:
<221> NAME/KEY: misc_feature
<222> LOCATION: (15)..(15)
<223> OTHER INFORMATION: n is a, c, g, or t

<400> SEQUENCE: 12
ggytcytcyt craanacrtt                                                   20

<210> SEQ ID NO 13
<211> LENGTH: 23
<212> TYPE: DNA
<213> ORGANISM: Artificial sequence
<220> FEATURE:
<223> OTHER INFORMATION: primer GSP1

<400> SEQUENCE: 13
tgaaaatgcg ttagtatgtg gat                                               23

<210> SEQ ID NO 14
<211> LENGTH: 23
<212> TYPE: DNA
<213> ORGANISM: Artificial sequence
<220> FEATURE:
<223> OTHER INFORMATION: primer GSP2

<400> SEQUENCE: 14
tgcctttgct gctttgaatg tat                                               23

<210> SEQ ID NO 15
<211> LENGTH: 17
<212> TYPE: DNA
<213> ORGANISM: Artificial sequence
<220> FEATURE:
<223> OTHER INFORMATION: primer GSP

<400> SEQUENCE: 15
aactacgagg tgctgcc                                                      17
```

```
<210> SEQ ID NO 16
<211> LENGTH: 25
<212> TYPE: DNA
<213> ORGANISM: Artificial sequence
<220> FEATURE:
<223> OTHER INFORMATION: primer GSP nest

<400> SEQUENCE: 16
gtcctcccca gttaccatat atagc                                           25

<210> SEQ ID NO 17
<211> LENGTH: 21
<212> TYPE: DNA
<213> ORGANISM: Artificial sequence
<220> FEATURE:
<223> OTHER INFORMATION: pprART F

<400> SEQUENCE: 17
atttagccgc gatgaaagaa c                                               21

<210> SEQ ID NO 18
<211> LENGTH: 17
<212> TYPE: DNA
<213> ORGANISM: Artificial sequence
<220> FEATURE:
<223> OTHER INFORMATION: pprART R

<400> SEQUENCE: 18
tcggcaaagg cacatcc                                                    17

<210> SEQ ID NO 19
<211> LENGTH: 22
<212> TYPE: DNA
<213> ORGANISM: Artificial sequence
<220> FEATURE:
<223> OTHER INFORMATION: primer 18SRT F

<400> SEQUENCE: 19
accaggtcca gacacaataa gg                                              22

<210> SEQ ID NO 20
<211> LENGTH: 21
<212> TYPE: DNA
<213> ORGANISM: Artificial sequence
<220> FEATURE:
<223> OTHER INFORMATION: primer 18SRT R

<400> SEQUENCE: 20
aagcagacaa atcactccac c                                               21

<210> SEQ ID NO 21
<211> LENGTH: 24
<212> TYPE: DNA
<213> ORGANISM: Artificial sequence
<220> FEATURE:
<223> OTHER INFORMATION: primer Nde-PPR

<400> SEQUENCE: 21
gggtttcata tgaaaaagcc tcag                                            24

<210> SEQ ID NO 22
<211> LENGTH: 21
<212> TYPE: DNA
<213> ORGANISM: Artificial sequence
<220> FEATURE:
<223> OTHER INFORMATION: primer Xho-PPR
```

-continued

```
<400> SEQUENCE: 22
ccgctcgaga actacaagat t                                          21

<210> SEQ ID NO 23
<211> LENGTH: 1122
<212> TYPE: DNA
<213> ORGANISM: Artificial sequence
<220> FEATURE:
<223> OTHER INFORMATION: tryA gene from Escherichia coli BW2952
<220> FEATURE:
<221> NAME/KEY: CDS
<222> LOCATION: (1)..(1122)

<400> SEQUENCE: 23 atg gtt gct gaa ttg acc gca tta cgc gat caa att gat gaa gtc gat      48
Met Val Ala Glu Leu Thr Ala Leu Arg Asp Gln Ile Asp Glu Val Asp
1               5                   10                  15 aaa gcg ctg ctg aat tta tta gcg aag cgt ctg gaa ctg gtt gct gaa      96
Lys Ala Leu Leu Asn Leu Leu Ala Lys Arg Leu Glu Leu Val Ala Glu
            20                  25                  30 gtg ggc gag gtg aaa agc cgc ttt gga ctg cct att tat gtt ccg gag     144
Val Gly Glu Val Lys Ser Arg Phe Gly Leu Pro Ile Tyr Val Pro Glu
        35                  40                  45 cgc gag gca tct atg ttg gcc tcg cgt cgt gca gag gcg gaa gct ctg     192
Arg Glu Ala Ser Met Leu Ala Ser Arg Arg Ala Glu Ala Glu Ala Leu
    50                  55                  60 ggt gta ccg cca gat ctg att gag gat gtt ttg cgt cgg gtg atg cgt     240
Gly Val Pro Pro Asp Leu Ile Glu Asp Val Leu Arg Arg Val Met Arg
65                  70                  75                  80 gaa tct tac tcc agt gaa aac gac aaa gga ttt aaa aca ctt tgt ccg     288
Glu Ser Tyr Ser Ser Glu Asn Asp Lys Gly Phe Lys Thr Leu Cys Pro
                85                  90                  95 tca ctg cgt ccg gtg gtt atc gtc ggt ggt ggc ggt cag atg gga cgc     336
Ser Leu Arg Pro Val Val Ile Val Gly Gly Gly Gly Gln Met Gly Arg
            100                 105                 110 ctg ttc gag aag atg ctg acc ctc tcg ggt tat cag gtg cgg att ctg     384
Leu Phe Glu Lys Met Leu Thr Leu Ser Gly Tyr Gln Val Arg Ile Leu
        115                 120                 125 gag caa cat gac tgg gat cga gcg gct gat att gtt gcc gat gcc gga     432
Glu Gln His Asp Trp Asp Arg Ala Ala Asp Ile Val Ala Asp Ala Gly
    130                 135                 140 atg gtg att gtt agt gtg cca atc cac gtt act gag caa gtt att ggc     480
Met Val Ile Val Ser Val Pro Ile His Val Thr Glu Gln Val Ile Gly
145                 150                 155                 160 aaa tta ccg cct tta ccg aaa gat tgt att ctg gtc gat ctg gca tca     528
Lys Leu Pro Pro Leu Pro Lys Asp Cys Ile Leu Val Asp Leu Ala Ser
                165                 170                 175 gtg aaa aat ggg cca tta cag gcc atg ctg gtg gcg cat gat ggt ccg     576
Val Lys Asn Gly Pro Leu Gln Ala Met Leu Val Ala His Asp Gly Pro
            180                 185                 190 gtg ctg ggg cta cac ccg atg ttc ggt ccg gac agc ggt agc ctg gca     624
Val Leu Gly Leu His Pro Met Phe Gly Pro Asp Ser Gly Ser Leu Ala
        195                 200                 205 aag caa gtt gtg gtc tgg tgt gat gga cgt aaa ccg gaa gca tac caa     672
Lys Gln Val Val Val Trp Cys Asp Gly Arg Lys Pro Glu Ala Tyr Gln
    210                 215                 220 tgg ttt ctg gag caa att cag gtc tgg ggc gct cgg ctg cat cgt att     720
Trp Phe Leu Glu Gln Ile Gln Val Trp Gly Ala Arg Leu His Arg Ile
225                 230                 235                 240 agc gcc gtc gag cac gat cag aat atg gcg ttt att cag gca ctg cgc     768
Ser Ala Val Glu His Asp Gln Asn Met Ala Phe Ile Gln Ala Leu Arg
```

```
                         245                     250                     255
cac ttt gct att ttt gct tac ggg ctg cac ctg gca gaa gaa aat gtt        816
His Phe Ala Ile Phe Ala Tyr Gly Leu His Leu Ala Glu Glu Asn Val
            260                     265                     270 cag ctt gag caa ctt ctg gcg ctc tct tcg ccg att tac cgc ctt gag        864
Gln Leu Glu Gln Leu Leu Ala Leu Ser Ser Pro Ile Tyr Arg Leu Glu
                275                     280                     285 ctg gcg atg gtc ggg cga ctg ttt gct cag gat ccg cag ctt tat gcc        912
Leu Ala Met Val Gly Arg Leu Phe Ala Gln Asp Pro Gln Leu Tyr Ala
        290                     295                     300 gac atc att atg tcg tca gag cgt aat ctg gcg tta atc aaa cgt tac        960
Asp Ile Ile Met Ser Ser Glu Arg Asn Leu Ala Leu Ile Lys Arg Tyr
305                     310                     315                 320 tat aag cgt ttc ggc gag gcg att gag ttg ctg gag cag ggc gat aag       1008
Tyr Lys Arg Phe Gly Glu Ala Ile Glu Leu Leu Glu Gln Gly Asp Lys
                325                     330                     335 cag gcg ttt att gac agt ttc cgc aag gtg gag cac tgg ttc ggc gat       1056
Gln Ala Phe Ile Asp Ser Phe Arg Lys Val Glu His Trp Phe Gly Asp
            340                     345                     350 tac gca cag cgt ttt cag agt gaa agc cgc gtg tta ttg cgt cag gcg       1104
Tyr Ala Gln Arg Phe Gln Ser Glu Ser Arg Val Leu Leu Arg Gln Ala
        355                     360                     365 aat gac aat cgc cag taa                                               1122
Asn Asp Asn Arg Gln
    370
```

<210> SEQ ID NO 24
<211> LENGTH: 1122
<212> TYPE: DNA
<213> ORGANISM: Artificial sequence
<220> FEATURE:
<223> OTHER INFORMATION: tryA gene from Escherichia coli BW2952
<220> FEATURE:
<221> NAME/KEY: CDS
<222> LOCATION: (1)..(1122)

<400> SEQUENCE: 24

```
atg gtt gct gaa ttg acc gca tta cgc gat caa att gat gaa gtc gat         48
Met Val Ala Glu Leu Thr Ala Leu Arg Asp Gln Ile Asp Glu Val Asp
1               5                   10                  15 aaa gcg ctg ctg aat tta tta gcg aag cgt ctg gaa ctg gtt gct gaa         96
Lys Ala Leu Leu Asn Leu Leu Ala Lys Arg Leu Glu Leu Val Ala Glu
            20                  25                  30 gtg ggc gag gtg aaa agc cgc ttt gga ctg cct att tat gtt ccg gag        144
Val Gly Glu Val Lys Ser Arg Phe Gly Leu Pro Ile Tyr Val Pro Glu
        35                  40                  45 cgc gag gca tct atg ttg gcc tcg cgt cgt gca gag gcg gaa gct ctg        192
Arg Glu Ala Ser Met Leu Ala Ser Arg Arg Ala Glu Ala Glu Ala Leu
    50                  55                  60 ggt gta ccg cca gat ctg att gag gat gtt ttg cgt cgg gtg atg cgt        240
Gly Val Pro Pro Asp Leu Ile Glu Asp Val Leu Arg Arg Val Met Arg
65                  70                  75                  80 gaa tct tac tcc agt gaa aac gac aaa gga ttt aaa aca ctt tgt ccg        288
Glu Ser Tyr Ser Ser Glu Asn Asp Lys Gly Phe Lys Thr Leu Cys Pro
                85                  90                  95 tca ctg cgt ccg gtg gtt atc gtc ggt ggt ggc ggt cag atg gga cgc        336
Ser Leu Arg Pro Val Val Ile Val Gly Gly Gly Gly Gln Met Gly Arg
            100                 105                 110 ctg ttc gag aag atg ctg acc ctc tcg ggt tat cag gtg cgg att ctg        384
Leu Phe Glu Lys Met Leu Thr Leu Ser Gly Tyr Gln Val Arg Ile Leu
        115                 120                 125
```

| | | | | | | | | | | | | | | | | |
|---|---|---|---|---|---|---|---|---|---|---|---|---|---|---|---|---|
| gag | caa | cat | gac | tgg | gat | cga | gcg | gct | gat | att | gtt | gcc | gat | gcc | gga | 432 |
| Glu | Gln | His | Asp | Trp | Asp | Arg | Ala | Ala | Asp | Ile | Val | Ala | Asp | Ala | Gly | |
| 130 | | | | 135 | | | | | 140 | | | | | | | |
| atg | gtg | att | gtt | agt | gtg | cca | atc | cac | gtt | act | gag | caa | gtt | att | ggc | 480 |
| Met | Val | Ile | Val | Ser | Val | Pro | Ile | His | Val | Thr | Glu | Gln | Val | Ile | Gly | |
| 145 | | | | | 150 | | | | | 155 | | | | | 160 | |
| aaa | tta | ccg | cct | tta | ccg | aaa | gat | tgt | att | ctg | gtc | gat | ctg | gca | tca | 528 |
| Lys | Leu | Pro | Pro | Leu | Pro | Lys | Asp | Cys | Ile | Leu | Val | Asp | Leu | Ala | Ser | |
| | | | | 165 | | | | | 170 | | | | | 175 | | |
| gtg | aaa | aat | ggg | cca | tta | cag | gcc | atg | ctg | gtg | gcg | cat | gat | ggt | ccg | 576 |
| Val | Lys | Asn | Gly | Pro | Leu | Gln | Ala | Met | Leu | Val | Ala | His | Asp | Gly | Pro | |
| | | | 180 | | | | | 185 | | | | | 190 | | | |
| gtg | ctg | ggg | cta | cac | ccg | atg | ttc | ggt | ccg | gac | agc | ggt | agc | ctg | gca | 624 |
| Val | Leu | Gly | Leu | His | Pro | Met | Phe | Gly | Pro | Asp | Ser | Gly | Ser | Leu | Ala | |
| | | | | 195 | | | | | 200 | | | | | 205 | | |
| aag | caa | gtt | gtg | gtc | tgg | tgt | gat | gga | cgt | aaa | ccg | gaa | gca | tac | caa | 672 |
| Lys | Gln | Val | Val | Val | Trp | Cys | Asp | Gly | Arg | Lys | Pro | Glu | Ala | Tyr | Gln | |
| 210 | | | | | 215 | | | | | 220 | | | | | | |
| tgg | ttt | ctg | gag | caa | att | cag | gtc | tgg | ggc | gct | cgg | ctg | cat | cgt | att | 720 |
| Trp | Phe | Leu | Glu | Gln | Ile | Gln | Val | Trp | Gly | Ala | Arg | Leu | His | Arg | Ile | |
| 225 | | | | 230 | | | | | 235 | | | | | 240 | | |
| agc | gcc | gtc | gag | cac | gat | cag | aat | atg | gcg | ttt | att | cag | gca | ctg | cgc | 768 |
| Ser | Ala | Val | Glu | His | Asp | Gln | Asn | Met | Ala | Phe | Ile | Gln | Ala | Leu | Arg | |
| | | | | 245 | | | | | 250 | | | | | 255 | | |
| cac | ttt | gct | act | ttt | gct | tac | ggg | ctg | cac | ctg | gca | gaa | gaa | aat | gtt | 816 |
| His | Phe | Ala | Thr | Phe | Ala | Tyr | Gly | Leu | His | Leu | Ala | Glu | Glu | Asn | Val | |
| | | | 260 | | | | | 265 | | | | | 270 | | | |
| cag | ctt | gag | caa | ctt | ctg | gcg | ctc | tct | tcg | ccg | att | tac | cgc | ctt | gag | 864 |
| Gln | Leu | Glu | Gln | Leu | Leu | Ala | Leu | Ser | Ser | Pro | Ile | Tyr | Arg | Leu | Glu | |
| | | 275 | | | | | 280 | | | | | 285 | | | | |
| ctg | gcg | atg | gtc | ggg | cga | ctg | ttt | gct | cag | gat | ccg | cag | ctt | tat | gcc | 912 |
| Leu | Ala | Met | Val | Gly | Arg | Leu | Phe | Ala | Gln | Asp | Pro | Gln | Leu | Tyr | Ala | |
| | 290 | | | | | 295 | | | | | 300 | | | | | |
| gac | atc | att | atg | tcg | tca | gag | cgt | aat | ctg | gcg | tta | atc | aaa | cgt | tac | 960 |
| Asp | Ile | Ile | Met | Ser | Ser | Glu | Arg | Asn | Leu | Ala | Leu | Ile | Lys | Arg | Tyr | |
| 305 | | | | | 310 | | | | | 315 | | | | | 320 | |
| tat | aag | cgt | ttc | ggc | gag | gcg | att | gag | ttg | ctg | gag | cag | ggc | gat | aag | 1008 |
| Tyr | Lys | Arg | Phe | Gly | Glu | Ala | Ile | Glu | Leu | Leu | Glu | Gln | Gly | Asp | Lys | |
| | | | | 325 | | | | | 330 | | | | | 335 | | |
| cag | gcg | ttt | att | gac | agt | ttc | cgc | aag | gtg | gag | cac | tgg | ttc | ggc | gat | 1056 |
| Gln | Ala | Phe | Ile | Asp | Ser | Phe | Arg | Lys | Val | Glu | His | Trp | Phe | Gly | Asp | |
| | | | 340 | | | | | 345 | | | | | 350 | | | |
| tac | gca | cag | cgt | ttt | cag | agt | gaa | agc | cgc | gtg | tta | ttg | cgt | cag | gcg | 1104 |
| Tyr | Ala | Gln | Arg | Phe | Gln | Ser | Glu | Ser | Arg | Val | Leu | Leu | Arg | Gln | Ala | |
| | | 355 | | | | | 360 | | | | | 365 | | | | |
| aat | gac | aat | cgc | cag | taa | | | | | | | | | | | 1122 |
| Asn | Asp | Asn | Arg | Gln | | | | | | | | | | | | |
| | 370 | | | | | | | | | | | | | | | |

<210> SEQ ID NO 25
<211> LENGTH: 1169
<212> TYPE: DNA
<213> ORGANISM: Wickerhamia fluorescens TK1
<220> FEATURE:
<223> OTHER INFORMATION: PPR-gene
<220> FEATURE:
<221> NAME/KEY: CDS
<222> LOCATION: (1)..(1092)

<400> SEQUENCE: 25

| | | | | | | | | | | | | | | | | |
|---|---|---|---|---|---|---|---|---|---|---|---|---|---|---|---|---|
| atg | aaa | aag | cct | cag | gtc | ctt | ata | ctt | gga | aga | ata | aag | gaa | tcc | ttg | 48 |
| Met | Lys | Lys | Pro | Gln | Val | Leu | Ile | Leu | Gly | Arg | Ile | Lys | Glu | Ser | Leu | |

```
  1             5                  10                  15
ccc gaa tac gtt tca ttc caa act aag ttt gaa tgc att cgc tat act      96
Pro Glu Tyr Val Ser Phe Gln Thr Lys Phe Glu Cys Ile Arg Tyr Thr
             20                  25                  30 gca tct tca gta gat cag cta atc aag gac ttc tca tct agt tta cgt     144
Ala Ser Ser Val Asp Gln Leu Ile Lys Asp Phe Ser Ser Ser Leu Arg
         35                  40                  45 aat ata cag gct ata tat ggt aac tgg gga gga ctc gcc tca ttt ggt     192
Asn Ile Gln Ala Ile Tyr Gly Asn Trp Gly Gly Leu Ala Ser Phe Gly
     50                  55                  60 ggc ttc aaa ggc aag tta ttg gag gca gca cct cgt agt tta aaa att     240
Gly Phe Lys Gly Lys Leu Leu Glu Ala Ala Pro Arg Ser Leu Lys Ile
 65                  70                  75                  80 att gca att tgt cag gtt ggg tat gat gag ttt gat tta gcc gcg atg     288
Ile Ala Ile Cys Gln Val Gly Tyr Asp Glu Phe Asp Leu Ala Ala Met
                 85                  90                  95 aaa gaa cgt gga att att tta acc aat gtc cct act cca ttg gca ttt     336
Lys Glu Arg Gly Ile Ile Leu Thr Asn Val Pro Thr Pro Leu Ala Phe
             100                 105                 110 gaa gca gtt gca gac ttg gtt ttg tac aat acg ttg atg gca ttt aga     384
Glu Ala Val Ala Asp Leu Val Leu Tyr Asn Thr Leu Met Ala Phe Arg
         115                 120                 125 aat ttc aaa ctt tac gag aat aat atg agc cct acc ctt aat aac acc     432
Asn Phe Lys Leu Tyr Glu Asn Asn Met Ser Pro Thr Leu Asn Asn Thr
     130                 135                 140 aac ctt tta aga aat tca ttg gtc aat ggt cag ttt gat caa gaa aca     480
Asn Leu Leu Arg Asn Ser Leu Val Asn Gly Gln Phe Asp Gln Glu Thr
145                 150                 155                 160 gga aaa tgc atc gtc cct cct ata gtg gga tgt gcc ttt gcc gac tct     528
Gly Lys Cys Ile Val Pro Pro Ile Val Gly Cys Ala Phe Ala Asp Ser
                 165                 170                 175 gtg tgt gag aga gaa aac tta tcc cca agg ggt cat aat gct gtt ata     576
Val Cys Glu Arg Glu Asn Leu Ser Pro Arg Gly His Asn Ala Val Ile
             180                 185                 190 ata gga ttt gga aga att gga aag ttg gca gcg caa cgc tta aat gca     624
Ile Gly Phe Gly Arg Ile Gly Lys Leu Ala Ala Gln Arg Leu Asn Ala
         195                 200                 205 att ggc atg aat att cat tat gtc aaa aga acc cag tgt tct cca gag     672
Ile Gly Met Asn Ile His Tyr Val Lys Arg Thr Gln Cys Ser Pro Glu
     210                 215                 220 gtg gaa cag gaa ctc tct ttt cct gtt act tac cac aag tca att gaa     720
Val Glu Gln Glu Leu Ser Phe Pro Val Thr Tyr His Lys Ser Ile Glu
225                 230                 235                 240 gaa gct ggc cgc ata gct gac ttg ttg gtt att tgc tgt cct gga aca     768
Glu Ala Gly Arg Ile Ala Asp Leu Leu Val Ile Cys Cys Pro Gly Thr
                 245                 250                 255 ccg tcc act aaa cat ttg atc aat tct gat act ttg gac aaa atg gag     816
Pro Ser Thr Lys His Leu Ile Asn Ser Asp Thr Leu Asp Lys Met Glu
             260                 265                 270 aag caa att aga att att aat att gga cgt ggc aca gtt att gat gaa     864
Lys Gln Ile Arg Ile Ile Asn Ile Gly Arg Gly Thr Val Ile Asp Glu
         275                 280                 285 aat gcg tta gta tgt gga tta aaa tct gac aaa gtt gcc ttt gct gct     912
Asn Ala Leu Val Cys Gly Leu Lys Ser Asp Lys Val Ala Phe Ala Ala
     290                 295                 300 ttg gat gtg ttt gaa gaa gaa cct ttt ata cat cca ggt tta atc ggt     960
Leu Asp Val Phe Glu Glu Glu Pro Phe Ile His Pro Gly Leu Ile Gly
305                 310                 315                 320 agg caa gat gta cat tta act cca cat att ggt tca tct aca agt gag    1008
```

```
Arg Gln Asp Val His Leu Thr Pro His Ile Gly Ser Ser Thr Ser Glu
            325                 330                 335
```

```
ctt ttt aac tac act gca aag caa gct atg caa aat att tct acg gct    1056
Leu Phe Asn Tyr Thr Ala Lys Gln Ala Met Gln Asn Ile Ser Thr Ala
            340                 345                 350
```

```
ttg tat aac aca aac gaa gaa atg aat ctt gta gtt tgagcttata          1102
Leu Tyr Asn Thr Asn Glu Glu Met Asn Leu Val Val
            355                 360
```

```
tccaaattac tttatttgta ttttaatcat aatgttttca ttttttataaa aaaaaaaaa   1162
```

```
aaaaaaa                                                             1169
```

<210> SEQ ID NO 26
<211> LENGTH: 364
<212> TYPE: PRT
<213> ORGANISM: Wickerhamia fluorescens TK1
<220> FEATURE:
<223> OTHER INFORMATION: PPR

<400> SEQUENCE: 26

```
Met Lys Lys Pro Gln Val Leu Ile Leu Gly Arg Ile Lys Glu Ser Leu
1               5                   10                  15

Pro Glu Tyr Val Ser Phe Gln Thr Lys Phe Glu Cys Ile Arg Tyr Thr
            20                  25                  30

Ala Ser Ser Val Asp Gln Leu Ile Lys Asp Phe Ser Ser Ser Leu Arg
        35                  40                  45

Asn Ile Gln Ala Ile Tyr Gly Asn Trp Gly Gly Leu Ala Ser Phe Gly
    50                  55                  60

Gly Phe Lys Gly Lys Leu Leu Glu Ala Ala Pro Arg Ser Leu Lys Ile
65                  70                  75                  80

Ile Ala Ile Cys Gln Val Gly Tyr Asp Glu Phe Asp Leu Ala Ala Met
                85                  90                  95

Lys Glu Arg Gly Ile Ile Leu Thr Asn Val Pro Thr Pro Leu Ala Phe
            100                 105                 110

Glu Ala Val Ala Asp Leu Val Leu Tyr Asn Thr Leu Met Ala Phe Arg
        115                 120                 125

Asn Phe Lys Leu Tyr Glu Asn Asn Met Ser Pro Thr Leu Asn Asn Thr
    130                 135                 140

Asn Leu Leu Arg Asn Ser Leu Val Asn Gly Gln Phe Asp Gln Glu Thr
145                 150                 155                 160

Gly Lys Cys Ile Val Pro Pro Ile Val Gly Cys Ala Phe Ala Asp Ser
                165                 170                 175

Val Cys Glu Arg Glu Asn Leu Ser Pro Arg Gly His Asn Ala Val Ile
            180                 185                 190

Ile Gly Phe Gly Arg Ile Gly Lys Leu Ala Ala Gln Arg Leu Asn Ala
        195                 200                 205

Ile Gly Met Asn Ile His Tyr Val Lys Arg Thr Gln Cys Ser Pro Glu
    210                 215                 220

Val Glu Gln Glu Leu Ser Phe Pro Val Thr Tyr His Lys Ser Ile Glu
225                 230                 235                 240

Glu Ala Gly Arg Ile Ala Asp Leu Leu Val Ile Cys Cys Pro Gly Thr
                245                 250                 255

Pro Ser Thr Lys His Leu Ile Asn Ser Asp Thr Leu Asp Lys Met Glu
            260                 265                 270

Lys Gln Ile Arg Ile Ile Asn Ile Gly Arg Gly Thr Val Ile Asp Glu
        275                 280                 285
```

```
Asn Ala Leu Val Cys Gly Leu Lys Ser Asp Lys Val Ala Phe Ala Ala
    290                 295                 300

Leu Asp Val Phe Glu Glu Pro Phe Ile His Pro Gly Leu Ile Gly
305                 310                 315                 320

Arg Gln Asp Val His Leu Thr Pro His Ile Gly Ser Ser Thr Ser Glu
                    325                 330                 335

Leu Phe Asn Tyr Thr Ala Lys Gln Ala Met Gln Asn Ile Ser Thr Ala
                340                 345                 350

Leu Tyr Asn Thr Asn Glu Glu Met Asn Leu Val Val
                355                 360

<210> SEQ ID NO 27
<211> LENGTH: 364
<212> TYPE: PRT
<213> ORGANISM: Candida dubliniensis
<220> FEATURE:
<223> OTHER INFORMATION: PPR-related protein

<400> SEQUENCE: 27

Met Thr Ile Lys Gln Lys Val Leu Phe Leu Glu Lys Pro Asn Val Glu
1               5                   10                  15

Asp Leu Lys Gln Phe Glu Ala Lys Phe Asp Cys Ile Tyr Tyr Thr Leu
                20                  25                  30

Ser Thr Leu Glu Gln Leu Leu Ile Asp Phe Gln Thr Ser Leu Gln Asp
            35                  40                  45

Val Glu Ala Ile Tyr Cys Gly Trp Asn Gly Phe Gly Met Phe Gly Gly
        50                  55                  60

Phe Arg Gly Lys Val Leu Ala His Ala Pro Gln Ser Leu Arg Ile Val
65                  70                  75                  80

Ala Thr Cys Ser Val Gly Tyr Asp Gly Phe Asp Ile Glu Arg Met Ser
                85                  90                  95

Glu Arg Asn Ile Val Leu Thr Asn Val Pro Ser Pro Leu Ala Phe Glu
                100                 105                 110

Ala Val Ala Asp Leu Ala Leu Tyr Asn Ala Ile Asn Ser Phe Arg Asn
            115                 120                 125

Phe Lys Leu Tyr Ala Glu Asn Leu Ser Ser Asn Gln Tyr Gly His Ser
        130                 135                 140

Gly Val Ser Arg Thr Ser Met Leu His Gly Asn Phe Asp Gln Ser Ser
145                 150                 155                 160

Gly Lys Ala Ile Val Glu Pro Val Val Gly His Thr Tyr Gly Tyr Ala
                165                 170                 175

Cys Cys Lys Arg Asp Asn Leu Ser Pro Arg Gly His Asn Ala Val Ile
                180                 185                 190

Val Gly Phe Gly His Ile Gly Glu Leu Ile Gly Arg Arg Leu Ala Cys
            195                 200                 205

Ile Gly Met Asn Val His Tyr Val Lys Arg Thr Arg Leu Ser Glu Ser
        210                 215                 220

Gln Glu Lys Ser Leu Gly Tyr Glu Val Thr Tyr His Glu Ser Leu Glu
225                 230                 235                 240

Glu Thr Lys Asp Ile Ala Asp Leu Ile Ile Ala Cys Pro Gly Thr
                245                 250                 255

Pro Ser Thr Arg His Met Ile Asn Lys Gln Leu Ile Asn Ser Met Gly
                260                 265                 270

Lys Pro Phe Arg Ile Ile Asn Ile Gly Arg Gly Phe Val Ile Asp Glu
            275                 280                 285
```

```
Asp Ala Leu Val Gly Gly Leu Lys Ser Gly Lys Val Leu Phe Ala Gly
    290                 295                 300

Leu Asp Val Phe Glu Asn Glu Pro Thr Ile His Pro Gly Leu Leu Gly
305                 310                 315                 320

Arg Asp Asp Val Val Leu Thr Pro His Ile Gly Ser Gly Ile Ala Glu
                325                 330                 335

Asn Tyr Arg Phe Thr Ala Leu Thr Ser Met Arg Asn Ile Glu Thr Ile
                340                 345                 350

Leu Arg Gly Tyr Asp Glu Glu Ile Asn Arg Val Asn
                355                 360

<210> SEQ ID NO 28
<211> LENGTH: 324
<212> TYPE: PRT
<213> ORGANISM: Escherichia coli
<220> FEATURE:
<223> OTHER INFORMATION: PPR-related protein

<400> SEQUENCE: 28

Met Lys Pro Ser Val Ile Leu Tyr Lys Ala Leu Pro Asp Asp Leu Leu
1               5                   10                  15

Gln Arg Leu Gln Glu His Phe Thr Val His Gln Val Ala Asn Leu Ser
                20                  25                  30

Pro Gln Thr Val Glu Gln Asn Ala Ala Ile Phe Ala Glu Ala Glu Gly
            35                  40                  45

Leu Leu Gly Ser Asn Glu Asn Val Asn Ala Ala Leu Leu Glu Lys Met
50                  55                  60

Pro Lys Leu Arg Ala Thr Ser Thr Ile Ser Val Gly Tyr Asp Asn Phe
65                  70                  75                  80

Asp Val Asp Ala Leu Thr Ala Arg Lys Ile Leu Leu Met His Thr Pro
                85                  90                  95

Thr Val Leu Thr Glu Thr Val Ala Asp Thr Leu Met Ala Leu Val Leu
            100                 105                 110

Ser Thr Ala Arg Arg Val Val Glu Val Ala Glu Arg Val Lys Ala Gly
            115                 120                 125

Glu Trp Thr Ala Ser Ile Gly Pro Asp Trp Tyr Gly Thr Asp Val His
130                 135                 140

His Lys Thr Leu Gly Ile Val Gly Met Gly Arg Ile Gly Met Ala Leu
145                 150                 155                 160

Ala Gln Arg Ala His Phe Gly Phe Asn Met Pro Ile Leu Tyr Asn Ala
                165                 170                 175

Arg Arg His His Lys Glu Ala Glu Glu Arg Phe Asn Ala Arg Tyr Cys
                180                 185                 190

Asp Leu Asp Thr Leu Leu Gln Glu Ser Asp Phe Val Cys Leu Ile Leu
                195                 200                 205

Pro Leu Thr Asp Glu Thr His His Leu Phe Gly Ala Glu Gln Phe Ala
            210                 215                 220

Lys Met Lys Ser Ser Ala Ile Phe Ile Asn Ala Gly Arg Gly Pro Val
225                 230                 235                 240

Val Asp Glu Asn Ala Leu Ile Ala Ala Leu Gln Lys Gly Glu Ile His
                245                 250                 255

Ala Ala Gly Leu Asp Val Phe Glu Gln Glu Pro Leu Ser Val Asp Ser
            260                 265                 270

Pro Leu Leu Ser Met Ala Asn Val Val Ala Val Pro His Ile Gly Ser
            275                 280                 285
```

```
Ala Thr His Glu Thr Arg Tyr Gly Met Ala Ala Cys Ala Val Asp Asn
    290                 295                 300

Leu Ile Asp Ala Leu Gln Gly Lys Val Glu Lys Asn Cys Val Asn Pro
305                 310                 315                 320

His Val Ala Asp

<210> SEQ ID NO 29
<211> LENGTH: 313
<212> TYPE: PRT
<213> ORGANISM: Solenostemon scutellarioides
<220> FEATURE:
<223> OTHER INFORMATION: PPR-related protein

<400> SEQUENCE: 29

Met Glu Ala Ile Gly Val Leu Met Met Cys Pro Met Ser Thr Tyr Leu
1               5                   10                  15

Glu Gln Glu Leu Asp Lys Arg Phe Lys Leu Phe Arg Tyr Trp Thr Gln
                20                  25                  30

Pro Ala Gln Arg Asp Phe Leu Ala Leu Gln Ala Glu Ser Ile Arg Ala
            35                  40                  45

Val Val Gly Asn Ser Asn Ala Gly Ala Asp Ala Glu Leu Ile Asp Ala
        50                  55                  60

Leu Pro Lys Leu Glu Ile Val Ser Ser Phe Ser Val Gly Leu Asp Lys
65                  70                  75                  80

Val Asp Leu Ile Lys Cys Glu Glu Lys Gly Val Arg Val Thr Asn Thr
                85                  90                  95

Pro Asp Val Leu Thr Asp Asp Val Ala Asp Leu Ala Ile Gly Leu Ile
            100                 105                 110

Leu Ala Val Leu Arg Arg Ile Cys Glu Cys Asp Lys Tyr Val Arg Arg
        115                 120                 125

Gly Ala Trp Lys Phe Gly Asp Phe Lys Leu Thr Thr Lys Phe Ser Gly
    130                 135                 140

Lys Arg Val Gly Ile Ile Gly Leu Gly Arg Ile Gly Leu Ala Val Ala
145                 150                 155                 160

Glu Arg Ala Glu Ala Phe Asp Cys Pro Ile Ser Tyr Phe Ser Arg Ser
                165                 170                 175

Lys Lys Pro Asn Thr Asn Tyr Thr Tyr Tyr Gly Ser Val Val Glu Leu
            180                 185                 190

Ala Ser Asn Ser Asp Ile Leu Val Val Ala Cys Pro Leu Thr Pro Glu
        195                 200                 205

Thr Thr His Ile Ile Asn Arg Glu Val Ile Asp Ala Leu Gly Pro Lys
    210                 215                 220

Gly Val Leu Ile Asn Ile Gly Arg Gly Pro His Val Asp Glu Pro Glu
225                 230                 235                 240

Leu Val Ser Ala Leu Val Glu Gly Arg Leu Gly Gly Ala Gly Leu Asp
                245                 250                 255

Val Phe Glu Arg Glu Pro Glu Val Pro Glu Lys Leu Phe Gly Leu Glu
            260                 265                 270

Asn Val Val Leu Leu Pro His Val Gly Ser Gly Thr Val Glu Thr Arg
        275                 280                 285

Lys Val Met Ala Asp Leu Val Val Gly Asn Leu Glu Ala His Phe Ser
    290                 295                 300

Gly Lys Pro Leu Leu Thr Pro Val Val
305                 310
```

```
<210> SEQ ID NO 30
<211> LENGTH: 332
<212> TYPE: PRT
<213> ORGANISM: Lactobacillus plantarum
<220> FEATURE:
<223> OTHER INFORMATION: PPR-related protein

<400> SEQUENCE: 30
```

| | | | | | | | | | | | | | | | |
|---|---|---|---|---|---|---|---|---|---|---|---|---|---|---|---|
| Met | Lys | Ile | Ile | Ala | Tyr | Ala | Val | Arg | Asp | Asp | Glu | Arg | Pro | Phe | Phe |
| 1 | | | | 5 | | | | | 10 | | | | | 15 | |
| Asp | Thr | Trp | Met | Lys | Glu | Asn | Pro | Asp | Val | Glu | Val | Lys | Leu | Val | Pro |
| | | | 20 | | | | | 25 | | | | | 30 | | |
| Glu | Leu | Leu | Thr | Glu | Asp | Asn | Val | Asp | Leu | Ala | Lys | Gly | Phe | Asp | Gly |
| | | 35 | | | | | 40 | | | | | 45 | | | |
| Ala | Asp | Val | Tyr | Gln | Gln | Lys | Asp | Tyr | Thr | Ala | Glu | Val | Leu | Asn | Lys |
| | 50 | | | | | 55 | | | | | 60 | | | | |
| Leu | Ala | Asp | Glu | Gly | Val | Lys | Asn | Ile | Ser | Leu | Arg | Asn | Val | Gly | Val |
| 65 | | | | | 70 | | | | | 75 | | | | | 80 |
| Asp | Asn | Leu | Asp | Val | Pro | Thr | Val | Lys | Ala | Arg | Gly | Leu | Asn | Ile | Ser |
| | | | | 85 | | | | | 90 | | | | | 95 | |
| Asn | Val | Pro | Ala | Tyr | Ser | Pro | Asn | Ala | Ile | Ala | Glu | Leu | Ser | Val | Thr |
| | | | 100 | | | | | 105 | | | | | 110 | | |
| Gln | Leu | Met | Gln | Leu | Leu | Arg | Gln | Thr | Pro | Met | Phe | Asn | Lys | Lys | Leu |
| | | 115 | | | | | 120 | | | | | 125 | | | |
| Ala | Lys | Gln | Asp | Phe | Arg | Trp | Ala | Pro | Asp | Ile | Ala | Lys | Glu | Leu | Asn |
| | 130 | | | | | 135 | | | | | 140 | | | | |
| Thr | Met | Thr | Val | Gly | Val | Ile | Gly | Thr | Gly | Arg | Ile | Gly | Arg | Ala | Ala |
| 145 | | | | | 150 | | | | | 155 | | | | | 160 |
| Ile | Asp | Ile | Phe | Lys | Gly | Phe | Gly | Ala | Lys | Val | Ile | Gly | Tyr | Asp | Val |
| | | | | 165 | | | | | 170 | | | | | 175 | |
| Tyr | Arg | Asn | Ala | Glu | Leu | Glu | Lys | Glu | Gly | Met | Tyr | Val | Asp | Thr | Leu |
| | | | 180 | | | | | 185 | | | | | 190 | | |
| Asp | Glu | Leu | Tyr | Ala | Gln | Ala | Asp | Val | Ile | Thr | Leu | His | Val | Pro | Ala |
| | | 195 | | | | | 200 | | | | | 205 | | | |
| Leu | Lys | Asp | Asn | Tyr | His | Met | Leu | Asn | Ala | Asp | Ala | Phe | Ser | Lys | Met |
| | 210 | | | | | 215 | | | | | 220 | | | | |
| Lys | Asp | Gly | Ala | Tyr | Ile | Leu | Asn | Phe | Ala | Arg | Gly | Thr | Leu | Ile | Asp |
| 225 | | | | | 230 | | | | | 235 | | | | | 240 |
| Ser | Glu | Asp | Leu | Ile | Lys | Ala | Leu | Asp | Ser | Gly | Lys | Val | Ala | Gly | Ala |
| | | | | 245 | | | | | 250 | | | | | 255 | |
| Ala | Leu | Val | Thr | Tyr | Glu | Tyr | Glu | Thr | Lys | Ile | Phe | Asn | Lys | Asp | Leu |
| | | | 260 | | | | | 265 | | | | | 270 | | |
| Glu | Gly | Gln | Thr | Ile | Asp | Asp | Lys | Val | Phe | Met | Asn | Leu | Phe | Asn | Arg |
| | | 275 | | | | | 280 | | | | | 285 | | | |
| Asp | Asn | Val | Leu | Ile | Thr | Pro | His | Thr | Ala | Phe | Tyr | Thr | Glu | Thr | Ala |
| | 290 | | | | | 295 | | | | | 300 | | | | |
| Val | His | Asn | Met | Val | His | Val | Ser | Met | Asn | Ser | Asn | Lys | Gln | Phe | Ile |
| 305 | | | | | 310 | | | | | 315 | | | | | 320 |
| Glu | Thr | Gly | Lys | Ala | Asp | Thr | Gln | Val | Lys | Phe | Asp | | | | |
| | | | | 325 | | | | | 330 | | | | | | |

PHENYLPYRUVATE REDUCTASE AND METHOD FOR MANUFACTURING OPTICALLY-ACTIVE PHENYLLACTIC ACID AND 4-HYDROXYL-PHENYLLACTIC ACID USING SAME ENZYME

SEQUENCE LISTING SUBMISSION VIA EFS-WEB

A computer readable text file, entitled "102771-5001_SequenceListing.txt," created on or about 25 Jul. 2013, with a file size of about 25 kb contains the sequence listing for this application and is hereby incorporated by reference in its entirety.

TECHNICAL FIELD

The present invention relates to phenylpyruvate reductase, a gene coding for the same, and a method for manufacturing optically active phenyllactate and optically active 4-hydroxyphenyllactate using same.

BACKGROUND ART

Both 3-phenyllactate and 4-hydroxyphenyllactate are antibacterial agents isolated from lactobacilli (Non-patent References 1-4).

3-phenyllactate has a wide spectrum of antibacterial activity, not just against *Aspergillus ochraceus, Penicillium roqueforti, Penicillium citrinium*, and other molds (Non-patent Reference 5), but also against *Listeria monocytogenes, Staphylococcus aureus, Escherichia coli* O157, and other such harmful gram-negative and positive bacteria (Non-patent References 1, 2, 5-7). This wide spectrum of antibacterial activity suggests the possibility of utilizing 3-phenyllactate as a food additive. It is moreover a useful compound that can be utilized in other applications such as pharmaceuticals, agricultural chemicals and intermediates thereof, aromatic biopolymer plastics, liquid crystals, and other such functional materials, biocompatible (medical) materials, and the like.

Because both 4-hydroxyphenyllactate and 3-phenyllactate are similarly derived from lactobacilli, this suggests not only the possibility of utilization as a food additive, but the potential to serve as an antibacterial additive for other applications, as well as potential in pharmaceuticals, agricultural chemicals, or intermediates thereof.

With regard to methods for the manufacture of these compounds, numerous attempts at manufacturing optically active 3-phenyllactate have been reported (Patent Reference 1), but from an environment impact and cost standpoint, a new method of synthesis that does not use such chemical substances would be preferable. Furthermore, no techniques have been devised to date for large-scale production of high purity 4-hydroxyphenyllactate. Currently, test reagents derived through organic chemical synthesis and principally racemic products, i.e., mixtures of D- and L-isomers, are marketed in small quantities, but a synthesis method affording higher efficiency of generation would be preferable.

One potential means for solving these problems would be a method for synthesis of optically active 3-phenyllactate or 4-hydroxyphenyllactate by microbial culture or with enzymes, to produce the desired compound in large quantities without the use of catalysts, organic solvents, and other such chemicals.

Various lactobacilli are known to be 3-phenyllactate-producing bacteria (Non-patent References 5, 9-11), including the *Asmomycota Geotrichum candidum* (Non-patent Reference 2) and the propionic acid-producing bacteria *Propionibacterium freudenreichii* (Non-patent Reference 8).

However, with regard to research on the enzyme molecular level conducted in relation to production of 3-phenyllactate, only purification of D,L-lactate dehydrogenase from *Lactobacillus*. sp SK007 has been reported, in 2008 (Non-patent Reference 12). Moreover, there are only two examples to date of cloning the genes of enzymes exhibiting enzyme activity on phenylpyruvate, which is predicted to be a precursor of 3-phenyllactate: recombinant D,L-lactate dehydrogenase derived from *Lactobacillus plantarum* SK002 (Non-patent Reference 13), and recombinant glyoxylate reductase/hydroxypyruvate reductase derived from *Rhizobium etli* CFN 42 (Non-patent Reference 16). It is unclear how these would contribute to production of 3-phenyllactate.

Moreover, while Patent References 2 and 3 report optically active 3-phenyllactate-producing bacteria, these are undesirable mixtures of R and S isomers.

In Patent Reference 4, it is reported that an enzyme produced by the filamentous bacteria *Mycelia sterilia* (FERM BP-2671), a PF1022 substance-producing bacteria, acts on phenylpyruvate so as to reduce it, converting it to (R)-2-hydroxy-3-phenylpropionic acid.

However, there is currently no efficient way to obtain high-purity optically active 3-phenyllactate.

As noted above, a manufacturing method whereby it would be possible to obtain high-purity optically active 3-phenyllactate and 4-hydroxyphenyllactate in large quantities has yet to be devised, and there is an urgent need to develop one.

PRIOR ART REFERENCES

Patent References

Patent Reference 1: Japanese Laid-Open Patent Application 2003-192633
Patent Reference 2: Japanese Laid-Open Patent Application 9-37792
Patent Reference 3: Japanese Laid-Open Patent Application 2000-300284
Patent Reference 4: International Publication 2001/81563

Non-Patent References

Non-Patent Reference 1: Layermicocca, P.; Valerio, F.; Evidente, A.; Lazzaroni, S.; Corsetti, A.; Gobetti, M., Appl. Environ. Microbiol., 2000 66 4084-4090
Non-Patent Reference 2: Dieuleveux, V.; Van Der Pyl, D.; Chataud, J.; Gueguen, M., Appl. Environ. Microbiol., 1998 64 800-803
Non-Patent Reference 3: Paola La et al., "Purification and characterization of novel antifungal compounds from the sourdough *Lactobacillus plantarum* strain 21B", Applied Environmental Microbiology (2000), 66(9), 4084-4090
Non-Patent Reference 4: Wanmeng Mu et al., "Production of 4-hydroxyphenyllactic acid by *Lactobacillus* sp. SK007" fermentation Journal of Bioscience and Bioengineering (2010), 109(4) 369-371
Non-Patent Reference 5: Ohhira, I., Kuwaki, S., Morita, H., Suzuki, T., Tomita, S., Hisamatsu, S., Sonoki, S., Shinoda, S., Biocontrol Sci. 2004 9 77-81
Non-Patent Reference 6: Dieuleveux, V.; Gueguen, M., J. Food Prot. 1998, 61 1281-1285
Non-Patent Reference 7: Dieuleveux, V.; Lemarinier, S., Gueguen, M., Int. J. Food Microbiol. 1998 40 177-183
Non-Patent Reference 8: Thierry, A.; Maillard, M., 2002 82 17-32

Non-Patent Reference 9: Strom, K.; Sjogren, J.; Broberg, A.; Schnurer, Appl. Environ. Microbiol. 2002 68 4322-4327

Non-Patent Reference 10: Magnusson, J.; Strom, K.; Roos, S.; Sjogren, J.; Schnurer, Microbiol. Lett. 2003 219 129-135

Non-Patent Reference 11: Valerio, F.; Layermicocca, P.; Pascale, M.; Visconti, A., Microbiol. Lett. 2004 233 289-295

Non-Patent Reference 12: Li, X., Pan., Mu, W. & Zhang, T. (2008)., Journal of Agricultural and Food Chemistry 56 7 2392-399

Non-Patent Reference 13: Jianghua, J.; Wanmeng, M.; Tao, Z.; Bo.; Appl. Biochem. Biotechnol. 2009 (in press)

Non-Patent Reference 14: Ishikura, Y.; Tsuzuki, S.; Takahashi, O.; Tokuda, C.; Nakanishi, R.; Shinoda, T., Taguchi, H., J. Biochem. 2005 138, 741-749

SUMMARY OF THE INVENTION

Problems to be Solved by the Invention

In view of the above problems and the current situation, the purpose of the present invention is to provide phenylpyruvate reductase for efficiently obtaining high-purity, optically active 3-phenyllactate and 4-hydroxyphenyllactate, a gene coding for the same, and a synthesis method for optically active 3-phenyllactate and 4-hydroxyphenyllactate using these.

Means Used to Solve the Above-Mentioned Problems

As the result of repeated trial and error, not just with known lactobacilli, but with a wide range of other microorganisms as well, the inventors discovered a novel yeast that produces a large quantity of optically active phenyllactate from glucose. It was discovered that the large quantity of optically active phenyllactate is due to the yeast having a novel and unique phenylpyruvate reductase (hereinafter "PPR") that, particularly when phenylpyruvate is used the substrate, exhibits high affinity and acts in such a way as to form optically active phenyllactate exclusively; and moreover that the PPR is a novel enzyme. It was further discovered that the gene coding for the distinctive PPR (hereinafter ppr gene) could be cloned, and this transformant used to manufacture the distinctive novel PPR through genetic engineering. It was further discovered that optically active phenyllactate can be obtained from glucose, using this transformant.

The inventors further discovered that the PPR of the present invention has affinity for 4-hydroxyphenylpyruvate as well, and when 4-hydroxyphenylpyruvate is the substrate, can selectively produce high-purity, optically active 4-hydroxyphenyllactate, specifically, high-purity D-4-hydroxyphenyllactate, therefrom. It was moreover discovered that a manufacturing method whereby high-purity, optically active 4-hydroxyphenyllactate can be produced in large quantities using D-glucose, which is inexpensive and consistently easy to procure, as a starting material (substrate), could be devised.

The PPR of the present invention is a novel enzyme having only 24% identity to the enzyme disclosed in Patent Reference 1, and having only about 40% identity to enzymes known in the past. Moreover, as will be shown in the examples presented below, the PPR of the present invention belongs to none of the existing HPPR and GRHPR families, and forms a novel family. Moreover, the PPR of the present invention exhibits enzyme activity several-fold higher than that of prior PPR, and has high industrial applicability. It is moreover clear that the novel yeast of the present invention, which produces this distinctive enzyme, and produces optically active phenyllactate from glucose, is an important genetic asset.

Specifically, the present invention relates to the following invention.

(1) A polynucleotide coding for phenylpyruvate reductase for producing D-phenyllactate from a substrate of phenylpyruvate, the polynucleotide being selected from the group consisting of:

(a) a polynucleotide comprising a base sequence shown by SEQ ID NO: 5;

(b) a polynucleotide hybridized under stringent conditions with a polynucleotide comprising a base sequence shown by SEQ ID NO: 5;

(c) a polynucleotide comprising a base sequence having at least 60% identity to a polynucleotide comprising a base sequence shown by SEQ ID NO: 5;

(d) a polynucleotide containing a base sequence shown by SEQ ID NO: 6, 7, or 8;

(e) a polynucleotide coding for an amino acid sequence shown by SEQ ID NO: 4;

(f) a polynucleotide coding for an amino acid sequence in which one or several amino acids are lost, substituted, or added, within an amino acid sequence shown by SEQ ID NO: 4; and (g) a polynucleotide coding for an amino acid sequence having at least 60% identity to an amino acid sequence shown by SEQ ID NO: 4.

(2) Phenylpyruvate reductase for producing D-phenyllactate from a substrate of phenylpyruvate, wherein the phenylpyruvate reductase contains any of:

(a) an amino acid sequence shown by SEQ ID NO: 4;

(b) an amino acid sequence in which one or several amino acids are lost, substituted, or added, within an amino acid sequence shown by SEQ ID NO: 4; and (c) an amino acid sequence having at least 60% identity to an amino acid sequence shown by SEQ ID NO: 4.

(3) A recombinant vector containing the nucleotide of (1).

(4) A transformant containing the recombinant vector of (3).

(5) The transformant of (4) wherein the host is a microorganism.

(6) The transformant of (5) wherein the microorganism is coliform bacteria or a phenylalanine- or tyrosine-producing recombinant microorganism.

(7) A method for manufacturing D-phenyllactate or D-4-hydroxyphenyllactate, characterized by the use of phenylpyruvate reductase comprising the proteins of (a), (b), or (c) below, to produce and recover D-phenyllactate or D-4-hydroxyphenyllactate from a substrate of phenylpyruvate:

(a) a protein comprising an amino acid sequence shown by SEQ ID NO: 4;

(b) a protein comprising an amino acid sequence in which one or several amino acids are lost, substituted, or added, within an amino acid sequence shown by SEQ ID NO: 4; and (c) a protein comprising an amino acid sequence having at least 60% identity to an amino acid sequence shown by SEQ ID NO: 4.

(8) The method for manufacturing D-phenyllactate or D-4-hydroxyphenyllactate of (7), characterized in that the reaction conditions for the phenylpyruvate reductase are a reaction temperature of 20-40° C. and pH of 6-7.

(9) A method for manufacturing D-phenyllactate or D-4-hydroxyphenyllactate, characterized by culturing using a microorganism containing genes that code for phenylpyruvate reductase comprising the proteins of (a), (b), or (c)

below, and production and recovery of D-phenyllactate or D-4-hydroxyphenyllactate from a microorganism substrate:

(a) a protein comprising an amino acid sequence shown by SEQ ID NO: 4;

(b) a protein comprising an amino acid sequence in which one or several amino acids are lost, substituted, or added, within an amino acid sequence shown by SEQ ID NO: 4; and (c) a protein comprising an amino acid sequence having at least 60% identity to an amino acid sequence shown by SEQ ID NO: 4.

(10) The method for manufacturing D-phenyllactate or D-4-hydroxyphenyllactate of (9), characterized in that the microorganism is a *Wickerhamia* yeast or mutant strain having same as the parent strain, or the transformant of (4) or (5).

(11) The method for manufacturing D-phenyllactate or D-4-hydroxyphenyllactate of (9), characterized in that the microorganism substrate is one or more substrates selected from D-glucose, L-phenylalanine, L-tyrosine, phenylpyruvate, and 4-hydroxyphenylpyruvate.

(12) The method for manufacturing D-phenyllactate or D-4-hydroxyphenyllactate of (10), wherein the *Wickerhamia* yeast is *Wickerhamia fluorescens*.

(13) A microorganism designated as *Wickerhamia fluorescens* TK1 (FERM AP-22048).

Advantages of the Invention

With the present invention, it is possible to efficiently obtain highly pure optically active 3-phenyllactate and 4-hydroxyphenyllactate.

BRIEF DESCRIPTION OF THE DRAWINGS

FIG. 15 "Southern blot analysis of total DNA using pprA as a probe" Shows southern hybridization, using a DNA fragment containing the pprA gene sequence, of total DNA of *W. fluorescens* TK1 strain treated with restriction enzymes (Hind III, Eco RI, Pst I, Bam HI). Total DNA from the *W. fluorescens* TK1 strain was digested with the restriction enzymes Hind III, Eco RI, Pst I, and Bam HI, electrophoresed, blotted onto a Zeta-Probe™ Blotting Membrane (Bio Rad), and subjected to hybridization using the probe.

FIG. 16 "Effect of phenylalanine on PPR activity and gene expression" Shows PPR activity and gene expression of the ppr gene (pprA gene) during culture of the *W. fluorescens* TK1 strain in GPMM medium (+Phe), GPAMM medium (+PPA), and MM medium (Glc). (A) Specific activities of PPR in cell-free extracts of the *W. fluorescens* TK1 strain cultured at 30° C. for 10 hours. Cells were cultured in MM medium containing 56 mM glucose (Glc), 56 mM glucose+5 mM phenylalanine (+Phe), or 56 mM glucose+5 mM phenylpyruvate (+PPA). (B) Quantitative PCR of pprA transcript. *W. fluorescens* NRRLYB-4819 was cultured as described above. Bars represent relative expression rates determined by real-time PCR.

FIG. 18 "Multiple alignments of deduced amino acid sequences of PPR derived from the *W. fluorescens* TK1 strain and PPR derived from other microorganisms" Shows results of alignment analysis using amino acid sequences of the PPR enzyme derived from the *W. fluorescens* TK1 strain and enzymes from other microorganisms (DLDH, GRHPR, HPPR). Protein primary structures are aligned using the CLUSTALX. Sequences are PPR-related proteins of *C. dublinensis* (Accession No. XP_002418129), *E. coli* (P37666), *S. scutellarioide* (Q65CJ7), and *L. plantarum* (BAA14352). Asterisks represent identical amino acids. Dots and colons represent conserved amino acids with substitutions. Dashes represent computer-generated gaps. An open box indicates the conserved sequence for the NAD-binding motif.

FIG. 19 Shows biosysthesis pathway of D-3-phenyllactate in the *W. fluorescens* TK1 strain.

BEST MODE FOR CARRYING OUT THE INVENTION

Figure 1:
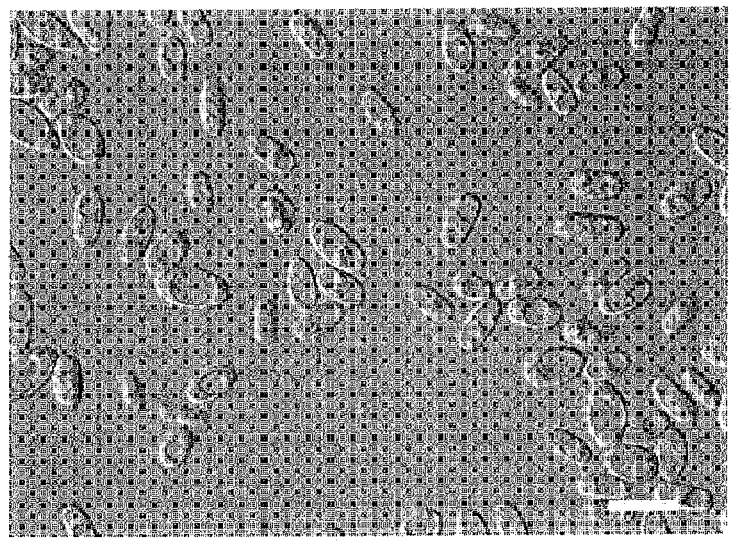
FIG. 1 Optical microscopic image of the *Wickerhamia fluorescens* TK1 strain.

1. Phenylpyruvate reductase of the present invention
    (1) Enzymological characteristics of PPR of the present invention
    (2) Amino acid sequence of PPR of the present invention and gene coding for same
    (3) Method of acquisition of PPR of the present invention
2. Method for manufacturing optically active 3-phenyllactate
    (1) Method for manufacturing optically active phenyllactate with the PPR of the present invention
    (2) Method for manufacturing optically active 3-phenyllactate with microorganisms having a gene coding for the PPR of the present invention
3. Method for manufacturing optically active 4-hydroxyphenyllactate
    (1) Method for manufacturing optically active 4-hydroxyphenyllactate with the PPR of the present invention
    (2) Method for manufacturing optically active 4-hydroxyphenyllactate with microorganism having a gene coding for the PPR of the present invention 1. Phenylpyruvate Reductase of the Present Invention The phenylpyruvate reductase of the present invention is a novel enzyme having the following enzymological characteristics and amino acid sequence, and a gene coding for the same. The PPR is suitably one forming a homodimer.

Highly pure D-phenyllactate or D-4-hydroxyphenyllactate can be obtained with the PPR of the present invention. Because it is possible to directly produce optically active phenyllactate or 4-hydroxyphenyllactate, separation and purification processes as with conventional organic compounds, which involve respectively separating mixtures containing substantially equal amounts of the D isomer and the L isomer, or eliminating one or the other of these, can be avoided, thereby improving the efficiency of operation and facilitating high purity. Due to the ease with which high-purity, optically active phenyllactate and hydroxyphenyllactate are obtained, the compound would be easy to utilize in various applications, and particularly in technical fields requiring high purity, such as pharmaceuticals, food additives, agricultural chemicals, and the like.

(1) Enzymological Characteristics (Action)

The PPR of the present invention acts on a substrate of phenylpyruvate and 4-hydroxyphenylpyruvate, to which has high affinity, to produce optically active phenyllactate (D-3-phenyllactate) and 4-hydroxyphenyllactate (D-4-hydroxyphenyllactate). In enantioselective terms, it is suitable to produce D-3-phenyllactate and D-4-hydroxyphenyllactate.

(Scheme 1)

[Formula 1]

Phenylpyruvate → D-3-Phenyllactate
(NADPH → NADP$^+$)

(Scheme 2)

4-hydroxyphenylpyruvate → 4-hydroxyphenyllactate

The substrate is not limited to phenylpyruvate and hydroxypyruvate; besides these, reduction of glyoxylate is preferable as well. Of these, the $k_{cat}/K_m$ value is highest when the phenylpyruvate is selected as the substrate.

It is possible to utilize NADH and NADPH as coenzymes, and specificity with respect to NADPH is high.

It is preferable for the enzyme to be one such that the $k_{cat}/K_m$ value (specificity constant) in phenylpyruvate and NADPH is 300-500 s$^{-1}$mM$^{-1}$ (Km value 0.40±0.07 mM), but there is no particular limitation as to the specificity constant. The specificity constant, $k_{cat}/K_m$ value, shows the efficiency with which an enzyme converts a substrate to a product.

The following methodology can be cited for the measurement conditions at this time. Using 50 mM phosphate buffer (pH 6.5), 2 mM phenylpyruvate, and 0.1 mM NADPH as the enzyme reaction solution, the enzyme is added, and reaction is brought at a temperature of 25° C., using an infrared/visible light spectrophotometer (340 nm) for quantification. The molar absorption coefficient for absorption of the 340 nm wavelength by NADPH is 6.2 mM$^{-1}$·cm$^{-1}$.

In preferred practice, optically active phenyllactate (D-3-phenyllactate) will be produced from 1 mole of the phenylpyruvate substrate and 1 mole of the NADPH coenzyme.

The molar ratio of D-3-phenyllactate and L-3-phenyllactate at this time is preferably 100-90:0-10, more preferably 100-95:0-5, and still more preferably 100-98:0-2. Furthermore, it is suitable for the optical purity of the D-3-phenyllactate (optically active phenyllactate) to be 99% or above.

The reaction is preferably an irreversible reaction. Herein, an irreversible reaction refers to failure for an enzyme reaction to occur, or no detectable phenylpyruvate, in the case where a combination of D-3-phenyllactate, L-3-phenyllactate, NAD$^+$, and NADP$^+$ is the substrate.

(Substrate)

One or more starting materials (substrate) are selected from 4-hydroxyphenylpyruvate, 3-phenylpyruvate, glyoxylate, and hydroxypyruvate, and a reduction reaction is catalyzed. It is preferable to avoid the use of pyruvic acid and oxazaloacetic acid as substrates.

(Optimal Reaction pH)

After preparing Tris-HCl buffer (pH 7-8) and phosphate buffer (pH 5-7) into buffers of each of several pH (25° C.), enzyme activity was determined under the measurement conditions described above under (Action), except for pH. High activity was exhibited at pH 6-7, particularly pH 6.5-7.

(Reaction Temperature)

At pH 6.5, satisfactory phenylpyruvate reductase reactions are exhibited at 20-40° C.

(Molecular Mass)

Measured by SDS-polyacrylamide gel electrophoresis (by a method such as Lammli), the PPR of the present invention exhibits molecular mass of 30,000-50,000 Da, particularly molecular mass of 40,000 Da.

In measurements by gel filtration, molecular mass of 70,000-90,000, and particularly molecular mass of 80,000, is exhibited.

For measurement analysis by gel filtration in this instance, the enzyme is run through a Superose gel filtration column (Superose 6 10/300) equilibrated in advance with elution buffer (10% glycerol, 1 mM dithiothreitol (DTT, 20 mM phosphate buffer, 0.15 mM NaCl pH 7), and eluted with elution buffer in an amount one-fold the column capacity.

For the standard protein, bovine serum albumen (m.w. 67,000), chymotrypsinogen (m.w. 25,000), α-amylase (m.w. 45,000), and β-amylase (m.w. 200,000) were used.

(Effects of Metal Ions and Inhibitors)

2) Effects of Metal Ions and Inhibitors

PPR activity is strongly inhibited (about 90-100% inhibited) by one or more species of metal ions selected from $Cu^{2+}$, $Zn^{2+}$, $Fe^{2+}$, $WO^{2-}$, and $Hg^{2+}$, moderately inhibited (about 30-40% inhibited) by one or more species of metal ions selected from $Ni^{2+}$ and $Co^{2+}$, and substantially uninhibited or completely uninhibited (about 15-0% inhibited) by one or more species of metal ions selected from Mn, $Mg^{2+}$, $Ca^{2+}$, and $Mo^{2+}$.

PPR activity is not excessively inhibited (about 30-50% inhibited) by one or more inhibitors selected from Tween 80™ and 2-mercaptoethanol, and substantially uninhibited (about 10-20% inhibited) by one or more inhibitors selected from TritonX-100 and ethylenediaminetetraacetate (EDTA).

Enzyme activity was determined under the measurement conditions described above under (Action), except for the addition of metal ions and inhibitors, in amounts of 1 mM of each substance.

(Partial Amino Acid Sequence)

The PPR of the present invention is suitably one having a partial amino acid sequence in at least the following N-terminal amino acid sequence and/or internal amino acid sequences. In this partial amino acid sequence, one or several amino acids may be substituted, lost, or inserted.

(Partial Amino Acid Sequence: N-Terminal Amino Acid Sequence)

Sequence of amino acid residues at N-terminal side: the sequence MKKPQVLILGRI of 12 amino acid residues at N-terminal side (SEQ ID NO: 1)

The sequence of amino acid residues at N-terminal side may be obtained by known methods (Edman, P. (1950) Acta Chem. Scand. 4: 283-293). As one example, the enzyme is electrophoresed by SDS-polyacrylamide gel electrophoresis, and after electrically moving the enzyme bands to a polyvinylidene fluoride (PVDR) film or the like, the determination is made through analysis by a protein sequencer.

(Partial Amino Acid Sequence: Internal Amino Acid Sequences)

Sequence of amino acid residues of trypsin-digested polypeptide: the sequence NIQAIYGNWGGLASFGGFK of 19 amino acid residues (SEQ ID NO: 2) and the sequence VAFAALDVFEEEPFIHPGLIGR of 22 amino acid residues (SEQ ID NO: 3).

Trypsin-digested peptide may be obtained by known methods (Shimizu, M. et al., (2009) Proteomics 9, 7-19). As one example, it may be obtained from the PPR of the present invention, refined through SDS-PAGE electrophoresis, by cutting out from the gel, followed by in-gel digestion with trypsin (temperature 36-38° C., pH 8-9, 4-18 hours). Alternatively, the process may be performed with a commercially available trypsin-digested peptide kit (Trypsin Profile IGD Kit: in-gel digestion kit (SIGMA-ALDORICH) or the like).

(2) Amino Acid Sequence of PPR of the Present Invention and Gene Coding for Same (Base Sequence)

The PPR of the present invention includes the following proteins (a), (b), and (c).

(a) A protein comprising an amino acid sequence shown by SEQ ID NO: 4.

(b) A protein comprising an amino acid sequence in which one or several amino acids are substituted, lost, or added, within an amino acid sequence shown by SEQ ID NO: 4, having phenylpyruvate reductase activity, and having high affinity for phenylpyruvate.

(c) A protein comprising an amino acid sequence having at least 60% identity to an amino acid sequence shown by SEQ ID NO: 4, having phenylpyruvate reductase activity, and having high affinity for phenylpyruvate.

As a result of comparisons for identity of the amino acid sequence of the PPR of the present invention shown by SEQ ID NO: 4, and the amino acid sequences of known phenylpyruvate reductases, identity with any of the known phenylpyruvate reductases was found to be extremely low (approximately 20°-500), suggesting that the PPR of the present invention is a novel enzyme, and forms a new group of enzymes. The ppr gene of the present invention includes a gene coding for the PPR of the present invention, and is therefore a novel gene.

In the present invention, identity of amino acid sequences and base sequences can be calculated by known algorithms such as the Lipman-Person method (Science, 227, 1435 (1985)), and sequences can be compared by these as well. Specifically, identity can be calculated by using a maximum matching program or search homology function of a search homology program from the genetic information processing software Genetyx-ver 8.1 (software developer: Genetyx Corp.). For example, it can be calculated by performing the analysis with the unit size to compare (ktup) set at 2.

Moreover, in the present invention, the transcription start region is the region containing the promoter and the transcription start point, and the ribosome binding region is a section equivalent to a Shine-Dalgarno (SD) sequence (Proc. Natl. Acad. Sci. USA 74, 5463 (1974)) which, together with the start codon, forms the translation start control region.

Herein, an amino acid sequence in which one or several amino acids are substituted, lost, or added, within an amino acid sequence shown by SEQ ID NO: 4, means an amino acid sequence respectively functionally equivalent to SEQ ID NO: 4, and refers to a sequence in which one or several (preferably 1 to 6, more preferably 1 to 3) amino acids are substituted, lost, or added, and that necessarily has phenylpyruvate reductase activity, and retains high affinity for phenylpyruvate. Addition is used in a sense that includes addition of one or several (preferably 1 to 6, more preferably 1 to 3) amino acids to either terminal.

The functionally equivalent amino acid may be any enzyme having at least phenylpyruvate reductase activity and 4-hydroxyphenylpyruvate reductase activity, and may further have additional properties. Furthermore, one having high affinity to phenylpyruvate is suitable. Moreover, one having substantially identical functionality to the proteins coded for by the ppr gene shown by SEQ ID NO: 5, specifically, the functionality of the PPR of the present invention discussed above, is suitable.

Herein, having phenylpyruvate reductase activity and 4-hydroxyphenylpyruvate reductase activity refers to the ability to transform phenylpyruvate and 4-hydroxyphenylpyruvate into D-3-phenyllactate and D-4-hydroxyphenyllactate, respectively, as in schemes 1 and 2 mentioned above. As to the extent of activity thereof, there is no particular limitation regarding the level of functionality provided that this functionality is expressed, that is, there is no limitation to be commensurate with that of the protein shown by SEQ ID NO: 4, and it may be higher or lower as well.

As additional properties, there may be cited the property of superior stability as compared with a protein comprising the amino acid sequence shown by SEQ ID NO: 4, the property of a different, or wider range of, reaction temperatures and/or pH, and the like.

An amino acid sequence having at least 60%, preferably at least 65%, more preferably at least 70%, more preferably at least 75%, more preferably at least 80%, more preferably at least 85%, still more preferably at least 90%, still more preferably at least 95%, and especially preferably at least 98%, identity to the amino acid sequence shown by SEQ ID NO: 4 is suitable.

As will be shown in examples following, a novel enzyme group was discovered through discovery of the PPR of the present invention, and it is therefore predicted that any enzyme functionally equivalent to a protein comprising the amino acid sequence shown by SEQ ID NO: 4, meaning having at least phenylpyruvate reductase activity and high affinity to phenylpyruvate as described above, and moreover having identity therewith within a range of at least about 60%, will be included in this novel enzyme group. Generally, most proteins exhibiting homology of 60% or above have specificity to similar enzymes, and it is thought that those exhibiting such a degree of homology would be included in the same enzyme group.

The ppr gene of the present invention is a gene that codes for a protein comprising the amino acid sequence shown by SEQ ID NO: 4, or for a protein comprising an amino acid sequence functionally equivalent to this amino acid sequence, and contains the following polynucleotides (a) to (d). Of these, those of (a) to (d) following are preferred.

(a) A polynucleotide comprising a base sequence shown by SEQ ID NO: 5.

(b) A polynucleotide hybridized under stringent conditions with a polynucleotide comprising a base sequence shown by SEQ ID NO: 5, and coding for a protein having phenylpyruvate reductase activity.

(c) A polynucleotide comprising a base sequence having at least 60% identity to a base sequence shown by SEQ ID NO: 5, and coding for a protein having phenylpyruvate reductase activity and having high affinity to phenylpyruvate.

(d) A polynucleotide containing a base sequence shown by SEQ ID NO: 6, 7, or 8, and coding for a protein having phenylpyruvate reductase activity and having high affinity to phenylpyruvate.

A base acid sequence having at least 65%, more preferably at least 70%, more preferably at least 75%, more preferably at least 80%, more preferably at least 85%, still more preferably at least 90%, still more preferably at least 95%, and especially preferably at least 98%, identity to the base sequence shown by SEQ ID NO: 5 is suitable.

Specifically, the ppr gene of the present invention includes genes comprising polypeptides which are polypeptides (DNA or the like) shown by the base sequence by SEQ ID NO: 5, and having undergone partial change in the base sequence through treatment with a mutation agent, random mutation, spontaneous mutations in specific regions, losses, insertions, or the like, and the mutated DNA hybridized under stringent conditions with DNA shown by the base of SEQ ID NO: 5, and which code for a protein having phenylpyruvate reductase activity. For example, there can be cited base sequences in which one or several (for example, 2 or 3) of the base sequences have been substituted, lost, or added. Addition is used in a sense that includes addition to either terminal. Here, "one or several" means 1 to 6, preferably 1 to 3.

Herein, "stringent conditions" refers to conditions disclosed, for example, in Molecular Cloning: A Laboratory Manual, $2^{nd}$ edition (Sambrook et al., 1989). Specifically, there may be cited conditions such as hybridization, together with a probe, in a solution containing 6×SSC (1×SSC formulation: 0.15 sodium chloride, 0.015 M sodium citrate, pH 7.0), 0.5% SDS, 5×Denhart's, and 100 mg/mL herring sperm DNA, at a constant temperature of 65° C. for 8-16 hours.

The genes shown in (b) to (d) have, for example, greater expression of mRNA as compared to the gene shown in (a), higher stability of the mRNA, and additional properties such as better stability of the translated proteins, and the like.

One or more regions, either a transcription start region, a translation start control region, or a secretion signal region, may be bound upstream of these genes in (a) to (d).

In the present invention, a transcription start region is a region containing a promoter and a transcription start point, and a ribosome binding region is a region equivalent to a Shine-Dalgarno (SD) sequence (Proc. Natl. Acad. Sci. USA 74, 5463 (1974)) which, together with the start codon, forms the translation start control region.

In the present invention, upstream or downstream of a gene refers not to the position relative to the replication start point; rather, upstream indicates a region continuous with the 5' side of the targeted gene or region, whereas downstream indicates a region continuous with the 3' side of the targeted gene or region.

(3) Method of Acquisition of PPR (Phenylpyruvate Reductase) of the Present Invention (i) It is possible for the PPR of the present invention to be produced or acquired from *Wickerhamia* yeasts or mutant strains thereof, genes that code for PPR, or a transformant (preferably a microorganism) in which a fragment thereof has been inserted.

There are no particular limitations as to the *Wickerhamia* yeast, provided it is a ascomycetous yeast having a gene that codes for the PPR enzyme discussed above, and any one having functionality for producing D-3-phenyllactate from phenylpyruvate and/or functionality for producing optically active phenyllactate (D-3-phenyllactate) from D-glucose via phenylpyruvate would be suitable.

As such yeasts, there may be cited, for example, *Wickerhamia fluorescens* and fungi having comparable mycological properties and physiological properties.

Furthermore, there may be cited the *W. fluorescens* TK1 (FERM AP-22048) strain (hereinafter also referred to as the "TK1 yeast"), equivalent fungi thereof, and mutant strains thereof. Mutant strains can be obtained by known methods involving treating a wild strain of TK1 yeast with ultraviolet, ionizing radiation, nitrous acid, nitrosoguanidine, ethyl methane sulfonate, or the like. Mutants also include mutant strains of wild strains in which further mutations are induced.

The mycological properties and physiological properties of the aforementioned *W. fluorescens* TK1 (FERM AP-22048) strain are shown below.

(a) 26S rDNA-D1/D2 Base Sequence

Base sequence shown by SEQ ID NO: 9.

(b) Morphological Characteristics

Shape: lemon-shaped, egg-shaped, eggplant-shaped

Mode of propagation: propagation occurs through bipolar budding, with broad budding regions, and formation of pseudohypha.

Spore formation: sports-cap-shaped ascospores are formed inside an ascus (c) Physiological/Biochemical Qualities Fermentation: D-glucose (+), saccharose (+), D-galactose (W), maltose (−)

Carbon source utilization: D-glucose (+), saccharose (+), D-galactose (+), maltose (−), inositol (−)

Nitrogen source utilization: nitrate (−)

40 specimens of the aforementioned TK1 yeast were collected from soil and water from the environs within Tsukuba City, Tsukuba Prefecture, Japan in November of 2007. After dilution as appropriate, these were applied onto YPD agar medium (see Example 1 below). After culture for 2-4 days at 28° C., the colonies which appeared were diluted as appropriate, then inoculated into fresh YPD agar medium, repeating the process to purify and separate strains.

One platinum loop of each separated strain was inoculated into liquid MM medium with D-glucose added (see Table 1), and cultured from 2 days to 4 days at 28° C. A culture supernatant of each strain was acquired using known procedures, measuring optically active phenyllactate in the culture supernatant by known measurement methods (for example, ODS liquid chromatography analysis, gas chromatography analysis, and the like), and picking out those with good production levels of optically active phenyllactate, to obtain the present TK1 strain collected from soil.

Further, from the mycological properties and physiological properties, the present strain was presumed to belong to *W. fluorescens*, and the present strain was named the *W. fluorescens* TK1 strain. The aforedescribed novel microorganism represented by this *Wickerhamia fluorescens* TK1 strain was deposited on 13 Dec. 2010 with the Patent Organism Depositary (IPOD) of the National Institute of Advanced Industrial Science and Technology (Central 6, Tsukuba Center, 1-1-1 Higashi, Tsukuba, Ibaraki 305-8566), as *Wickerhamia fluorescens* TK1 (FERM AP-22048).

To produce the PPR of the present invention from the TK1 yeast, it is inoculated into a typical medium for yeast culture, and cultured at an appropriate temperature. Production of the PPR yeast of the present invention from the culture broth can be carried out in accordance with the usual methods. Specifically, the culture broth can be centrifugally separated to remove the cells, followed by concentration and recovery from the cell-free extract using known yeast separation and purification methods. As examples, there can be cited gel filtration chromatography, ultrafiltration membranes, and other filtration methods, or methods of enzyme precipitation with ammonium sulfate, and the like.

While it is possible for the PPR of the present invention to be obtained from the natural world in the above fashion, the gene thereof can be cloned from the chromosomal DNA of the microorganisms discussed above (ideally, ascomycota), and PPR produced and recovered in large quantities.

There can be adopted methods of production of the PPR of the present invention in which a method for cloning the ppr gene; for example, a method involving linkage to a DNA vector which can stably amplify the gene in question, or introduction onto chromosomal DNA that can sustain the gene, or the like, to stably amplify the DNA that codes for the PPR of the present invention, and to further introduce the gene into a host that is able to stably and efficiently express it.

The ppr gene of the present invention may be acquired by known procedures (for example, see Sambrook, J., Fritch, E. F., and Maniatis, T. (1989) in Molecular Cloning: A Laboratory Manual, Vol. 2, Cold Spring Harbor Laboratory Press, Cold Spring Harbor, N.Y.). As one example, genomic DNA is extracted from a PPR-producing strain, and cut with an appropriate restriction enzyme, followed by preparation of a library comprising the genomic DNA of the PPR-producing strain, using a fuzzy vector. Alternatively, total RNA is extracted from a PPR-producing strain, and after preparation of cDNA corresponding to the mRNA in a reverse transcription enzyme reaction with oligo dT as the primer, preparation of a library comprising the genomic DNA of the PPR-producing strain, using a fuzzy vector.

On the basis of N-terminal amino acid sequences or internal amino acid sequences like those above, an appropriate primer is synthesized, and used to carry out a polymerase chain reaction (PCR) with PPR-producing strain-derived genomic DNA or cDNA as the template, to amplify the DNA fragment of the ppr gene. Using this DNA fragment as a probe, the genomic library or cDNA library is screened. In this way it is possible to isolate all regions of the ppr gene or those regions necessary for expression. After having determined the base sequence of the DNA fragments, it is possible to then introduce suitable restriction enzyme cutting sites by a procedure such as PCR, upstream of the translation start codon and downstream of the translation stop codon, and to obtain a gene fragment containing a polypeptide comprising only the ppr gene of the present invention.

(Recombinant Vector and Method of Preparation)

According to the present invention, it is possible to apply a recombinant vector containing a polypeptide or ppr gene that codes for PPR. In so doing, it is possible to obtain a transformant, which transformant can be used to manufacture PPR by genetic engineering, through culturing or the like.

The procedures and methods for constructing the recombinant vector of the present invention can be ones commonly used in the field of genetic engineering (Sambrook, J., Fritch, E. F., and Maniatis, T. (1989) in Molecular Cloning: A Laboratory Manual, Vol. 2, Cold Spring Harbor Laboratory Press, Cold Spring Harbor, N.Y.).

As vectors that can be used in the present invention, there can be cited those inserted into host chromosomal DNA, or those in which a vector having a self-replicatable or autonomously-replicatable sequence is present in plasmid form within a host cell. As plasmid vectors, there may cited, for example, in the case of a coliform bacteria host, pUC18, pBR322 (Takara Bio), or the like, or in the case of *corynebacterium*, pK4 or the like. The number of copies of a gene present in the host cell can be one or several copies.

It is possible for the recombinant vector of the present invention to be prepared, for example, by operational linkage, respectively, of a promoter (control region) upstream, and of a terminator downstream, of the polynucleotide sequence that codes for PPR, or in some cases, by operational linkage to a gene marker and/or other control sequence.

It is possible for linkage of promoters and terminators to the gene of the present invention, and insertion of an expression unit into a vector, to be carried out by known methods (Sambrook, J., Fritch, E. F., and Maniatis, T. (1989) in Molecular Cloning: A Laboratory Manual, Vol. 2, Cold Spring Harbor Laboratory Press, Cold Spring Harbor, N.Y.).

There are no particular limitations as to promoters and terminators used in the present invention. For example, control sequences of genes for glycolic enzymes such as 3-phosphoglycerate kinase, glutaraldehyde-3-phosphate dehydrogenase, and the like; control sequences of genes for amino acid synthesizing enzymes such as tryptophan synthetase and the like; control sequences of genes for hydrolytic enzymes such as amylase, protease, lipase, cellulase, and the like; or control sequences of genes for oxidoreductase enzymes such as nitrate reductase, orotidine-5'-phosphate dehydratase, alcohol dehydratase, and the like. A control sequence refers to a polypeptide which can exhibit a desired functionality in a control region.

The gene of the present invention may also be expressed as a fusion protein linked to an alien gene that codes a transcription region of another protein.

Introduction of a gene marker into the recombinant vector can be performed, for example, by introducing appropriate restriction enzyme cutting sites into the control sequence by PCR method, introducing this into a plasmid vector, and then linking a selection marker gene, such as a drug-resistance gene and/or an auxotrophy-compensating gene.

It is possible to select the selection marker gene as appropriate depending on the transformant selection method; for example, a gene that codes for drug resistance, or a gene that compensates for auxotrophy, can be used.

As drug-resistance genes, there can be cited genes resistant to drugs such as distamycin, benomyl, oligomycin, hygromycin, G418, bleomycin, phosphinothricin, ampicillin, kanamycin, and the like.

As genes that compensate for auxotrophy, there can be cited the argB gene, the pyr4 gene, the trpC gene, the TRP1 gene, the niaD gene, the LEU2 gene, the URA3 gene, and the like.

(Transformants into which the Recombinant Vector of the Present Invention has been Introduced)

According to the present invention, a recombinant vector obtained in the above-described manner is used to transform a host (preferably a microorganism), to obtain a transformant.

There are no particular limitations as to the host used, provided it is serviceable as a host for gene recombination, and preferably a microorganism. As hosts that can be used, there can be cited, for example, any microorganisms such as bacteriomycota, mycota, and the like, of which the use of coliform bacteria, *corynebacterium*, lactobacilli, actinomycetes, yeasts, or filamentous bacteria, and specifically microorganisms belonging to the *Escheria, Pseudomonas, Flavobacterium, Bacillus, Serratia, Corynebacterium, Brevibacterium, Agrobacterium, Acetobacter, Gluconobacter, Lactobacillus, Streptococcus*, or *Streptomyces* genus, or mutant strains thereof, is suitable. From the standpoint of ease of recombination, coliform bacteria or mutant strains thereof are more preferred.

At this time, the microorganisms are suitably recombinant microorganisms having undergone mutations, such as substitutions, insertions, losses, or inactivation of genes, so as to readily produce optically active phenyllactate or 4-hydroxyphenyllactate. Phenylalanine-producing cells (phenylalanine-producing recombinant microorganisms) and tyrosine-producing cells (tyrosine-producing recombinant microorganisms would be suitable as the recombinant microorganism.

As procedures for giving rise to mutations of genes such as those mentioned above, there may be cited, for example, the recombinant PCR process (PCR Technology, Stockton press (1989); site-specific mutagenesis (Kramer, W. and Frits, H., J. Methods in Enzymology, 154, 350 (1987); a double cross process using DNA fragments prepared by the SOE (splicing by overlap extension)-PCR process (Gene, 77, 61, (1987)); methods of treatment with chemical agents (N-methyl-N'-nitrosoguanidine, nitrous acid, or the like); methods of chemical synthesis of the target genes, and the like.

The phenylalanine-producing cells may be microorganisms whose genes have undergone mutation by known techniques, so as to be able to produce L-phenylalanine in large quantities (and preferably producing large quantities of L-phenylalanine from a substrate of D-glucose). As such phenylalanine-producing recombinant microorganisms there may be cited *Escherichia* microorganisms that have lost the tryR gene and the tryA gene through transformation by a recombinant vector containing DNA coding for prephenic acid dehydrogenase and 3-deoxy-D-arabinohep tulosonate-7-phosphate synthase released from feedback inhibition, and the like.

As more specific microorganisms, there may be cited, for example, the ATCC31882 strain, the ATCC3188 strain 3, the ATCC31884 strain (American Type Culture Collection allotment), the AJ12740 strain (FERM P-12999), the AJ12741 strain (FERM T-13000) (Japanese Laid-Open Patent Application 1993-344881), and other such phenylalanine-producing recombinant coliform bacteria; *Corynebacteirum glutamicum* and the like may be cited as yet another phenylalanine-producing recombinant microorganism.

The tyrosine-producing cells are suitably microorganisms whose genes have undergone mutation by known techniques, so as to be able to produce L-tyrosine in large quantities (and preferably producing large quantities of L-tyrosine from a substrate of D-glucose). As examples of such tyrosine-producing recombinant microorganisms there may be cited recombinant coliform bacteria obtained by insertion of the tyrA gene (SEQ ID NO: 24: YP_002927556) into phenylalanine-producing bacteria (for example, *E. coli* ATCC31882 (procured by the ATCC)) by known procedures; *Escherichia* microorganisms having L-tyrosine producing ability, and retaining mutant type prephenic acid dehydrogenase released from feedback inhibition, and the like (for example, see Japanese Laid-Open Patent Application 2006-311833 and Japanese Laid-Open Patent Application 2007-325592).

It is possible for the transformant (microorganism) of the present invention to be obtained by introduction of a recombinant vector for gene expression prepared as described above, and introduced into the aforementioned host by the usual methods.

As introduction methods, there may be cited an electrophoration process, an ethylene glycol process, an *agrobacterium* process, a competent process, a lithium acetate process, a calcium chloride process, and the like, suitably selected according to the host cells used.

Current knowledge about optical isomerism of phenyllactate produced by known phenylpyruvate reductase is very limited. It has been reported that the produced phenyllactate is racemic. Due to these circumstances, it is considered difficult to obtain optically active phenyllactate in high concentration, specifically, highly purified optically active phenyllactate, on a commercial scale.

Under these circumstances, it is possible for the PPR of the present invention to produce optically active phenyllactate of very high purity, with little or substantially no possibility of physiological activity differing between enantiomers. Moreover, because the reaction is irreversible, the optically active phenyllactate may accumulate in high concentration, which is advantageous from the aspect of efficient recovery. Furthermore, because the PPR of the present invention has high affinity for phenylpyruvate, a wide range of other substrates, i.e., 4-hydroxyphenylpyruvate, glyoxylate, or hydroxypyruvate, may be used as well.

The $k_{cat}/K_m$ value of the PPR of the present invention is several ten-fold higher than the $k_{cat}/K_m$ value of known phenylpyruvate reductase, and therefore it is possible for the PPR of the present invention to produce large quantities of optically active phenyllactate.

Furthermore, with the PPR of the present invention, it is possible for the enzyme to be produced in large quantities by a transformant employing a gene coding for the same, and it is further possible to produce large quantities of optically active phenyllactate on a commercial scale using the PPR so obtained.

(2. Method for Manufacturing Optically Active 3-phenyllactate)

The method for manufacturing optically active 3-phenyllactate according to the present invention has at least a manufacturing process in which D-3-phenyllactate can be produced from phenylpyruvate (enzyme reaction system: see Scheme 1 cited earlier).

Furthermore, a method having a manufacturing process in which phenylpyruvate is produced from a starting material such as D-glucose or L-phenylalanine is suitable for the purposes of low production cost and ease of procurement.

There are no particular limitations as to the manufacturing process by which phenylpyruvate is produced from D-glucose, and organic synthesis processes or fermentation processes (biosynthesis reactions) may be cited. The Shikimate pathway may be cited, for example.

There are no particular limitations as to the manufacturing process for producing L-phenylalanine from D-glucose, and known procedures, for example those disclosed in Japanese Laid-Open Patent Application 5-344811 or U.S. Pat. No. 4,681,852 may be cited. As the manufacturing process for producing phenylpyruvate from L-phenylalanine, there may be cited an enzyme reaction system employing an amino group transfer enzyme such as an aminotransferase or the like.

At this time, the manufacturing process by which phenylpyruvate can be produced from a starting material such as D-glucose or L-phenylalanine (for example, a reaction system by a fermentation process by enzymes, microorganisms, or the like) may be included in the method for manufacturing optically active 3-phenyllactate of the present invention.

Specifically, employing the PPR of the present invention and/or the microorganism of the present invention, optically active 3-phenyllactate is produced from a substrate, and the optically active 3-phenyllactate is recovered.

At this time, a medium containing at least the PPR enzyme of the present invention, for example, a culture broth in which the microorganism of the present invention has been cultured, a culture broth from which the microorganism has been removed, a ruptured microorganism solution, a cell-free extract from which ruptured material has been removed, or the like, may be employed. The medium may contain a series of enzyme groups for a Shikimate pathway reaction (specifically, 7-phospho-2-dehydro-3-deoxyarabinoheptonate aldolase, 3-dehydroquinate synthase, 3-dehydroquinate dehydratase, shikimate dehydrogenase, shikimate kinase, 3-phosphoshikimate-1-carboxylvinyl transferase (5-enolpyruvylshikimate-3-phosphate synthase, chorismate synthase, chorismate mutase, and the like), as well as phenylalanine synthesis enzyme groups (in specific terms, prephenate dehydrogenase, tyrosine aminotransferase, and the like).

As coenzymes, those employing NADPH and/or NADH are suitable, of which NADPH is preferred due to the elevated yield of optically active phenyllactate.

There is no particular limitation as to the format of the reaction in the method for manufacturing optically active 3-phenyllactate of the present invention; a batch process or continuous flow process may be carried out.

The PPR of the present invention or the microorganism of the present invention may be immobilized. The procedure for immobilization is not particularly limited and may be any of the known procedures, for example, carrier binding processes involving immobilization of a microorganism/enzyme on a water-insoluble carrier through physical adsorption, ionic binding, or organic bonding; crosslinking processes for crosslinking immobilization with a reagent having a divalent functional group, such as glutaraldehyde; or an inclusion process for confining the microorganism/enzyme in a gel having a network structure, or in a semipermeable membrane.

Moreover, the solvent employed for the reaction may be either a polar or non-polar solvent, with water or a water-soluble solvent being preferred, and 90 to 100 mass % of water being especially preferred. Herein, the water-soluble organic solvent is preferably one that readily dissolves compounds that have the benzene ring, for example, straight chain or branched chain alcohols or acetone may be cited. As these lower alcohols (those with carbon numbers of 1 to 5 are suitable) there may be cited, for example, methanol, ethanol, propanol, and other such monohydric alcohols, 1,3-butanediol and other such dihydric or polyhydric alcohols. Combinations of these are also acceptable.

(1) Method for Manufacturing Optically Active Phenyllactate with the PPR of the Present Invention Using the PPR of the present invention, it is possible to produce and recover optically active 3-phenyllactate from an enzyme substrate. Optically active 3-phenyllactate may be obtained on a continuous basis through concomitant use of enzymes other than PPR as mentioned previously.

Here, the reason that phenylpyruvate is a suitable enzyme substrate is that it gives a high yield of optically active phenyllactate.

A suitable reaction temperature is preferably 5-50° C., more preferably 10-40° C., and still more preferably 20-40° C.

A suitable reaction time (one turn) is preferably 12 hours to one week, and more preferably 2 to 4 days.

A suitable reaction pH is preferably 5 to 8, more preferably 6 to 7. Adjustment of pH at this time may be performed using known pH adjusters such as phosphate buffer or the like.

(2) Method for Manufacturing Optically Active 3-phenyllactate with a Microorganism Having a Gene Coding for the PPR of the Present Invention A suitable method for manufacturing the optically active phenyllactate of the present invention is one involving culture of a microorganism containing a gene that codes for phenylpyruvate reductase comprising the proteins of (a), (b), or (c) below, and production and recovery of optically active phenyllactate from the microorganism substrate.

(a) A protein comprising an amino acid sequence shown by SEQ ID NO: 5

(b) A protein comprising an amino acid sequence in which one or several amino acids are substituted, lost, or inserted, into an amino acid sequence shown by SEQ ID NO: 5, having phenylpyruvate reductase activity, and having high affinity for phenylpyruvate (c) A protein comprising an amino acid sequence having at least 60% identity to an amino acid sequence shown by SEQ ID NO: 5, having phenylpyruvate reductase activity, and having high affinity for phenylpyruvate Herein, microorganism refers to the wild strain (TK1 strain) mentioned previously, a mutant strain thereof, the aforementioned transformant, or the like, and may be aerobic or anaerobic.

The microorganism substrate at this time is preferably one or more selected from D-glucose, L-phenylalanine, phenylpyruvate, or the like.

In cases in which the microorganism substrate is D-glucose, procurement at low cost is possible, and it is moreover possible to produce optically active phenyllactate in large quantities, making it a suitable substrate. Moreover, the discovery of the ppr gene, by which it is possible to produce large quantities of aromatic compounds, as well as optically active 3-D-phenyllactate, from the simple sugar glucose, is extremely useful industrially. In such cases, a recombinant microorganism obtained by introducing the gene coding for the PPR of the present invention into an L-phenylalanine-producing microorganism is preferred.

In the case of manufacture of optically active phenyllactate by microorganisms, besides the microorganism containing the gene coding for phenylpyruvate reductase as discussed above, microorganisms for producing the aforementioned microorganism substrate, such as microorganisms having genes coding for an enzyme group that synthesizes phenylalanine, or microorganisms having genes coding for an enzyme group series for a shikimate pathway reaction to produce the aforementioned microorganism substrate, may be utilized.

For example, there may be cited pre-culture using microorganisms that produce the microorganism substrate, followed by main culture employing the microorganism of the present invention; culture in which these microorganisms are used simultaneously, and the like.

Suitable media for use in culture of the microorganisms include, in addition to enriched culture media used to grow microorganisms, those containing at least the aforementioned microorganism substrate. At this time, the microorganism substrate is suitably contained in the medium at a concentration of 0.01-20% (mass/volume), more preferably 0.1-3% (mass/volume), and still more preferably 1-2% (mass/volume).

In cases in which the microorganism is, for example, a yeast, the enriched culture medium may be an MM culture medium containing, per 1 L of culture medium, 1-30 g of D-glucose, 0-5 g of a microorganism substrate other than glucose, 5-7 g of $NaNO_3$, 0.4-0.6 g of KCl, 0.4-7 g of $MgSO_4 \cdot 7H_2O$, 1-2 g of $KH_2PO_4$, 1-3 mL of Hutner's trace elements, and distilled water. The Hutner's trace elements are those given in the Examples below. 0-3% of an appropriate yeast extract, or 0-2% of polypeptone, would be acceptable as well.

In cases in which the microorganism is, for example, coliform bacteria, the medium may be an M9 culture medium containing, per 1 L of culture medium, 1-30 g of D-glucose, 0-5 g of a microorganism substrate other than glucose, 5-7 g of $Na_2PO_4$, 2-4 g of $KH_2PO_4$, 9-11 g of NaCl, 5-7 g of $NH_4Cl$, 0.4-7 g of $MgSO_4 \cdot 7H_2O$, 0.02-0.04 g of $CaCl_2 \cdot H_2O$, 0.04-0.05 g of thiamine HCl, 0.2-0.4 g of trypsin, 0.2-0.4 g of tryptophan, 1-3 mL of Hutner's trace elements, and distilled water.

In the case of coliform bacteria, the medium may be a phenyllactate production culture medium containing, per 1 L of culture medium, 1-30 g of D-glucose, 0-5 g of a microorganism substrate other than glucose, 11-13 g of $Na_2PO_4$, 5-7 g of $KH_2PO_4$, 0.4-0.6 g of NaCl, 0.9-1.1 g of $NH_4Cl$, 0.02-0.4 g of $MgSO_4 \cdot 7H_2O$, 0.01-0.02 g of $CaCl_2 \cdot 2H_2O$, 0.01-0.02 g of thiamine HCl, 9-11 g of trypsin, 4-6 g of 5.00 g/L yeast extract, 1-3 mL of trace elements 2, and distilled water.

The Hutner's trace elements and the trace elements 2 are those given in the Examples below (see Table 2 and Table 12).

It would be suitable to further add 9-11 g of trypsin, or 4-5 g of yeast extract.

The culturing conditions may be established appropriately depending on the microorganisms used.

The culture temperature is preferably 5-50° C., more preferably 10-40° C., and still more preferably 20-40° C., as such temperature levels are suitable in terms of good growth of the microorganism and avoiding precipitation of the substrate and product.

The culture time (one turn) is preferably about 0.5 day to 2 weeks, more preferably about one week, and still more preferably about 3 to 0.5 days.

The culture pH is preferably 4 to 9, and more preferably, in the case of yeast, is suitably 6 to 7, or in the case of coliform bacteria is suitably 6 to 8. Adjustment of culture pH may be controlled to within the prescribed range, with an appropriate pH adjuster.

Suitable stirring is preferably carried out at 100-1000 rpm, more preferably 400-600 rpm.

In the case of aerobic culture employing air, suitable air flow is preferably 0.01-1 L/min, more preferably 0.1-0.3 L/min.

Furthermore, the concentration of the aforementioned culture substrate in the culture medium during the culture period is suitably adjusted to one within a prescribed concentration, from the standpoint of efficient production. For example, a 500 g/L D-glucose solution may be added continuously or intermittently, preferably at a rate of 0.1-5 g/L/h, more preferably 1-2 g/L/h.

There are no particular limitations as to the method for recovering 3-D-phenyllactate, and known separation and purification methods may be employed. As means for removing cells, known means such as centrifugal separation, filtration, or the like may be cited. As means for separation/purification of 3-D-phenyllactate, crystallization, ultrafiltration, ion exchange, activated carbon treatment, chromatographic separation, and other known means may be cited.

As a chromatographic separation method, for example, a procedure employing an ODS column chromatograph may be cited. As a crystallization method, a procedure of extraction with an organic solvent and recrystallization may be cited. As one suitable example, extraction with a mixed solvent of methanol and hexane (=2:1-1:2):water (=2:1-1:2 is suitable.

(Method for Manufacturing Optically Active 4-hydroxyphenyllactate)

The method for manufacturing optically active 4-hydroxyphenyllactate (D-4-hydroxyphenyllactate) of the present invention has at least a manufacturing process by which optically active 4-hydroxyphenyllactate can be produced from 4-hydroxyphenylpyruvate (enzyme reaction system: see Scheme 2 cited earlier).

The 4-hydroxyphenylpyruvate substrate is one of the metabolic intermediates of phenylalanine and tyrosine, and therefore the manufacturing process should utilize this metabolic system.

Furthermore, a method having a manufacturing process in which optically active 4-hydroxyphenyllactate is produced from a starting material such as D-glucose or L-tyrosine is suitable for the purposes of low production cost and ease of procurement.

There are no particular limitations as to the manufacturing process by which L-tyrosine is produced from D-glucose, and known procedures such as that disclosed, for example, in Japanese Laid-Open Patent Application 2006-311833 or the like may be cited. As a manufacturing process for producing tyrosine from L-phenylalanine, and then producing 4-hydroxyphenylpyruvate, an enzyme reaction system employing phenylalanine hydroxylase, tyrosine aminotransferase, or the like may be cited. There are no particular limitations as to the manufacturing process by which 4-hydroxyphenylpyruvate is produced from D-glucose, and organic synthesis processes or fermentation processes (synthesis reactions) may be cited. The Shikimate pathway may be cited, for example.

At this time, the manufacturing process by which 4-hydroxyphenylpyruvate can be produced from a starting material such as D-glucose or L-tyrosine (for example, a reaction system by a fermentation process by enzymes, microorganisms, or the like) may be included in the method for manufacturing optically active 4-hydroxyphenyllactate of the present invention discussed previously.

Specifically, employing the biocatalysts mentioned above (enzymes and/or microorganisms are suitable), optically active 4-hydroxyphenyllactate is produced from the substrate, and the optically active 4-hydroxyphenyllactate (D-4-hydroxyphenyllactate is suitable) is recovered.

At this time, a medium containing at least the aforementioned enzyme, for example, a culture broth in which the microorganism of the present invention has been cultured, a culture broth from which the microorganism has been removed, a ruptured microorganism solution, a cell-free extract from which ruptured material has been removed, or the like, may be employed. The medium may contain a series of enzyme groups for a Shikimate pathway reaction (specifically, 7-phospho-2-dehydro-3-deoxyarabinoheptonate aldolase, 3-dehydroquinate synthase, 3-dehydroquinate dehydratase, shikimate dehydrogenase, shikimate kinase, 3-phosphoshikimate-1-carboxylvinyl transferase (5-enolpyruvylshikimate-3-phosphate synthase, chorismate synthase, chorismate mutase, and the like), as well as phenylalanine synthesis enzyme groups (in specific terms, prephenate dehydrogenase, tyrosine aminotransferase, and the like), phenylalanine hydroxylase, and the like.

As coenzymes, those employing NADPH and/or NADH are suitable, of which NADPH is preferred due to the elevated yield of optically active 4-hydroxyphenyllactate.

There is no particular limitation as to the format of the reaction in the method for manufacturing optically active 4-hydroxyphenyllactate of the present invention, and a batch process or continuous flow process may be carried out.

The aforementioned enzyme or the aforementioned microorganism may be immobilized. The procedure for immobilization is not particularly limited and may be any of the known procedures, for example, carrier binding processes involving immobilization of a microorganism/enzyme on a water-insoluble carrier through physical adsorption, ionic binding, or organic bonding; crosslinking processes for crosslinking immobilization with a reagent having a divalent functional group, such as glutaraldehyde; or an inclusion process for confining the microorganism/enzyme in a gel having a network structure, or in a semipermeable membrane.

Moreover, the solvent employed for the reaction may be either a polar or non-polar solvent, with water or a water-soluble solvent being preferred, and 90 to 100 mass % of water being especially preferred. Herein, the water-soluble organic solvent is preferably one that readily dissolves compounds that have the benzene ring, for example, straight chain or branched chain alcohols or acetone may be cited. As these lower alcohols (those with carbon numbers of 1 to 3 are suitable) there may be cited, for example, methanol, ethanol, propanol, and other such monohydric alcohols, 1,3-butanediol and other such dihydric or polyhydric alcohols. Combinations of these are also acceptable.

(1) Method for Manufacturing Optically Active 4-hydroxyphenyllactate with the PPR of the Present Invention Using the PPR of the present invention, it is possible to produce and recover optically active 4-hydroxyphenyllactate from an enzyme substrate. Optically active 4-hydroxyphenyllactate may be obtained on a continuous basis through concomitant use of enzymes other than the PPR of the present invention, as mentioned previously.

Here, the reason that 4-hydroxyphenylpyruvate is a suitable enzyme substrate is that it gives a high yield of optically active 4-hydroxyphenyllactate.

A suitable reaction temperature is preferably 5-50° C., more preferably 10-40° C., and still more preferably 20-40° C.

A suitable reaction time (one turn) is preferably 12 hours to one week, and more preferably 2 to 4 days.

A suitable reaction pH is preferably 5 to 8, more preferably 6 to 7. Adjustment of pH at this time may be performed using known pH adjusters such as phosphate buffer or the like.

(2) Method for Manufacturing Optically Active 4-hydroxyphenyllactate with a Microorganism Having a Gene Coding for the PPR of the Present Invention A suitable method for manufacturing the optically active 4-hydroxyphenyllactate of the present invention is one involving culture of a microorganism containing a gene that codes for the PPR of the present invention, and production and recovery of optically active 4-hydroxyphenyllactate from the microorganism substrate.

Herein, microorganism refers to the wild strain mentioned previously, a mutant strain thereof, or the aforementioned transformant or the like, and may be aerobic or anaerobic. For example, a strain containing a gene that codes for 4-hydroxyphenylpyruvate reductase, a strain containing a gene that codes for the PPR enzyme, an ATCC strain, or the like may be cited.

The microorganism substrate at this time is preferably one or more selected from D-glucose, L-tyrosine, 4-hydroxyphenylpyruvate, or the like. During use of the enzyme of the present invention, it is possible to produce optically active 4-hydroxyphenyllactate by combining other enzymes as well.

In cases in which the microorganism substrate is D-glucose, procurement at low cost is possible, and it is moreover possible to produce optically active 4-hydroxyphenyllactate in large quantities, making it a suitable substrate. Moreover, utilization focused on the ppr gene, by which it is possible to selectively produce, with high purity, large quantities of aromatic compounds, as well as optically active D-4-hydroxyphenyllactate, from the simple sugar glucose, is extremely useful industrially. In such cases, a recombinant microorganism obtained by introducing the gene coding for the aforementioned enzyme into an L-tyrosine-producing microorganism via a vector or the like is preferred.

In the case of manufacture of optically active 4-hydroxyphenyllactate by a microorganism, besides the microorganism containing the gene coding for the aforementioned enzyme as discussed above, microorganisms for producing the aforementioned microorganism substrate, such as microorganisms having genes coding for an enzyme group series for a shikimate pathway reaction to produce the aforementioned microorganism substrate, microorganisms having genes coding for an enzyme group that synthesizes phenylalanine, or a gene coding for phenylalanine hydroxylase, may be utilized.

For example, there may be cited pre-culture using microorganisms that produce the microorganism substrate, followed by main culture employing the microorganism of the present invention; culture in which these microorganisms are used simultaneously, and the like.

Suitable media for use in culture of the microorganisms include, in addition to enriched culture media used to grow microorganisms, those containing at least the aforementioned microorganism substrate. At this time, the microorganism substrate is suitably [contained] in the medium at [a concentration of 0.01-20% (mass/volume), more preferably 0.1-3% (mass/volume), and still more preferably 1-2% (mass/volume).

In cases in which the microorganism is, for example, a yeast, the enriched culture medium may be an MM culture medium containing, per 1 L of culture medium, 1-30 g of D-glucose, 0-5 g of a microorganism substrate other than glucose, 5-7 g of $NaNO_3$, 0.4-0.6 g of KCl, 0.4-7 g of $MgSO_4 \cdot 7H_2O$, 1-2 g of $KH_2PO_4$, 1-3 mL of Hutner's trace elements, and distilled water. The Hutner's trace elements are those given in the Examples below. 0-3% of an appropriate yeast extract, or 0-2% of polypeptone, would be acceptable as well.

In cases in which the microorganism is, for example, coliform bacteria, the medium may be an M9 culture medium containing, per 1 L of culture medium, 1-30 g of D-glucose, 6-24 g of a microorganism substrate other than glucose, 3-12 g of $Na_2PO_4$, 0.5-1 g of $KH_2PO_4$, 0.5-2 g of NaCl, 0.05-0.05 g of $NH_4Cl$, 0.015-0.030 g of $MgSO_4 \cdot 7H_2O$, 0.015-0.050 g of $CaCl_2 \cdot H_2O$, 0.050-0.10 g of thiamine HCl, trypsin, and 1-2 mL of Hutner's trace elements.

A hydroxyphenyllactate production culture medium (phenyllactate production culture medium) containing, per liter of culture medium, 1-30 g of D-glucose, 6-24 g of a microorganism substrate other than glucose, 3-12 g of $Na_2HPO_4$, 0.5-1 g of $KH_2PO_4$, 0.5-1.0 g of NaCl, 0.05-1 g of $NH_4Cl$, 0.015-0.03 g of $MgSO_4 \cdot 7H_2O$, 0.015-0.05 g of $CaCl_2 \cdot 2H_2O$, 1-10 g of thiamine HCl, 0-1.5 g of tryptone, 0.5-5 g of 5.00 g/L yeast extract, 1-3 mL of Trace elements 2, and distilled water may also be cited.

It would be suitable to further add 5-20 g (preferably 9-11 g) of tryptone, or 4-7 g of yeast extract.

The culturing conditions may be established appropriately depending on the microorganisms used.

The culture temperature is preferably 5-50° C., more preferably 10-40° C., and still more preferably 20-40° C., as [such temperature levels] are suitable in terms of good growth of the microorganism and avoiding precipitation of the substrate and product.

The culture time (one turn) is preferably about 0.5 day to 2 weeks, more preferably about one week, and still more preferably about 3 to 5 days.

The culture pH is preferably 4 to 9, and more preferably, in the case of yeast, is suitably 6 to 7, or in the case of coliform bacteria is suitably 6 to 8. Adjustment of culture pH may be controlled to within the prescribed range, with an appropriate pH adjuster.

Suitable stirring is preferably carried out at 100-1000 rpm, more preferably 400-600 rpm.

In the case of aerobic culture employing air, suitable air flow is preferably 0.1-1 L/min, more preferably 0.1-0.3 L/min.

Furthermore, the concentration of the aforementioned culture substrate in the culture medium during the culture period is suitably adjusted to one within a prescribed concentration, from the standpoint of efficient production. For example, a 500 g/L D-glucose solution may be added continuously or intermittently, preferably at a rate of 0.1-5 g/L/h, more preferably 1-2 g/L/h.

pH is close to 6-8.

There are no particular limitations as to the method for recovering the optically active 4-hydroxyphenyllactate obtained by the manufacturing method discussed above, and known separation and purification methods may be employed. As means for removing cells, known means such as centrifugal separation, filtration, or the like may be cited. As means for separation/purification of the optically active 4-hydroxyphenyllactate (D-4-hydroxyphenyllactate), crystallization, ultrafiltration, ion exchange, activated carbon treatment, chromatographic separation, and other known means may be cited.

As a chromatographic separation method, for example, a procedure employing an ODS column chromatograph may be cited.

As a crystallization method, a procedure of extraction with an organic solvent and recrystallization may be cited. As one suitable example, extraction with a mixed solvent of methanol and hexane (=2:1-1:2):water (=2:1-1:2 is suitable. At this time, acidification to a pH of 2-4 with an acid such as hydrochloric acid or the like is preferred.

Employing the manufacturing method of the present invention, highly pure D-4-hydroxyphenyllactate, rather than a racemic form, can be obtained, and the separation and purification process can be simplified, making the present technique suited to commercial production. Moreover, enzymes and microorganisms suited to this can be easily obtained, and in this respect as well the present technique is suited to industrial production.

In terms of high purity, it is advantageous for the proportion of one or the other to be high, preferably 85% or above, more preferably 90% or above, still more preferably 95% or above, and even more preferably 98% or above.

EXAMPLES

The specific examples described below are not limiting of the present invention.

Example 1

Screening of D-3-phenyllactate-Producing Cells and Purification of Phenylpyruvate Reductase (PPR) Produced Thereby (1) Acquisition of TK1 Strain Producing D-3-phenyllactate Specimens were collected from soil and water at several dozen sites in the environs within Tsukuba City, Ibaraki Prefecture, Japan. After dilution as appropriate, these were applied onto YPD agar medium (2% yeast extract, 1% polypeptone, 1% D-glucose, 1 L distilled water). After culture for 2-4 days at 28° C., the colonies which appeared were diluted as appropriate, then inoculated into fresh YPD agar medium, purified, and separated. One platinum loop of each separated strain was inoculated into the minimum medium (hereinafter termed "MM") liquid culture medium shown in Table 1, and cultured for 2 to 4 days under aerobic conditions.

Those having good production of optically active phenyllactate were screened by the following measurement method, determining one strain to be the TK1 strain.

TABLE 1

Minimum medium (1 L distilled water)

| | |
|---|---|
| D-glucose (grape sugar) | 100 mM |
| $NH_4Cl$ | 0.53 g (10 mM) |
| KCl | 0.52 g |
| $MgSO_4 \cdot 7H_2O$ | 0.52 g |
| $KH_2PO_4$ | 1.35 g |
| *(Hutner's) trace element | 2 mL |
| pH | 7.2 |

TABLE 2

*(Hunter's) trace elements

| | |
|---|---|
| $CoCl_2 \cdot 6H_2O$ | 0.16 g |
| $FeSO_4 \cdot 7H_2O$ | 0.50 g |
| $ZnSO_4 \cdot 7H_2O$ | 2.20 g |
| $NaMoO_4 \cdot 2H_2O$ | 0.11 g |
| $MnCl_2 \cdot 4H_2O$ | 0.50 g |
| $CuSO_4 \cdot 5H_2O$ | 0.16 g |
| $H_3BO_3$ | 1.10 g |
| Per liter | |

(Methods for Qualification and Quantification of 3-phenyllactate)

1) Qualification of 3-phenyllactate by Gas Chromatography-Mass Spectrometer (GC/MS)

The specimen was completely suspended in 200 µL of 1% NaOH, 167 µL of methanol, and 34 µL of pyridine. To this was added 20 µL of methyl chlorocarbonate, stirring vigorously to methylate the specimen. After repeating the operation of adding methyl chlorocarbonate and stirring, 400 µL of chloroform was added and stirred. Next, 50 mM of sodium bicarbonate was added, and after stirring, the aqueous layer was removed. The chloroform layer obtained thereby was completely dehydrated by adding 0.1 g of sodium sulfate to the chloroform layer thusly obtained, and the organic acids contained in the solution thusly obtained were measured by GC/MS (GCMS-QP2010 Plus by Shimadzu). Conditions for the GC/MS analysis were as follows.

In the case of analysis of the culture broth, 5 mL of the culture broth was prepared to pH of from 9 to 10 with 1% NaOH, reduced-pressure dried in a centrifugal evaporator, and used as samples.

Analyzer: GC/MS-QP2010 Plus (Shimadzu)
Column: DB-5 (0.32 mm×30 m)
Column temperature: 60° C. (2 min)-8° C./min-180° C. (5 min)-40° C./min-220° C. (5 min)
Interface temperature: 230° C.
Ion source temperature: 250° C.
Carrier gas: He
Flow rate: 30 mL/min 2) Quantification of 3-phenyllactate by High-Performance Liquid Chromatography (HPLC)

Using HPLC, quantification of 3-phenyllactate in samples was performed through analysis under the following conditions.

In the case of analysis of a culture broth, the culture medium supernatant from which cells were removed by filtration, centrifugal separation, or the like is used as the sample.

Analyzer: HP-1100 (Hewlett-Packard)
Column: TSKgel ODS-80Th (4.6×150 mm, Tosoh, Tokyo, Japan)
Column temperature: 28° C.
Flow velocity: 1.0 mL/min
Mobile phase: 20 mm potassium phosphate buffer (pH 2.5): methanol (6:4, v/v)

3) Chiral Analysis Employing HPLC

The optical isomerism of 3-phenyllactate in the sample (enzyme reaction solution) was determined employing HPLC, under the following analysis conditions. In the case of analysis of a culture broth, the culture supernatant from which cells were removed from the culture broth by filtration, centrifugal separation, or the like is used as the sample.

Analyzer: HP-1100 (Hewlett-Packard)
Column: Nucleosil Chiral-1 (Macherey-Nagel)
Column temperature: 60° C.
Flow velocity: 1.2 mL/min
Mobile phase: 0.5 mL $CuSO_4$ (2) Identification of TK1 Strain From a YPD agar medium in which cells were grown in advance, one platinum loop of cells was inoculated into 10 mL of YPD culture medium aliquoted into a test tube with a total capacity of 50 mL, and shake cultured for 2 days at 30° C., 120 rpm.

Cells were harvested from 2.5 mL of a pre-culture broth by centrifugal separation, and the precipitate was washed with physiological saline. This was inoculated into a test tube of total capacity of 50 mL containing 10 mL of an MM culture medium, and shake cultured for 2 days at 30° C., 120 rpm. During culture under anaerobic conditions, the gas phase of the test tube was replaced with nitrogen, and after being stoppered with a butyl rubber stopper, the sample was shake cultured for 6 days at 30° C., 120 rpm.

(Analysis of 26S rDNA-D1/D2 Base Sequence)

Procedures from extraction to cycle sequencing steps were carried out in accordance with the protocols: DNA extraction: (physical rupture and Marmur (1961)); PCR (puReTaq Ready-To-Go PCR beads (Amersham Biosciences, NJ, USA)); cycle sequencing: BigDye Terminator v3.1 Kit (Applied Biosystems, CA, USA); primers used: (NL1 and NL4 (O'Donnell, 1993)); sequencing: (ABI PRISM 3130×1 Genetic Analyzer System Applied Biosystems, CA, USA); homology search and simple phylogenetic analysis: (APORON2.0 Software (Techno Suruga Laboratory Co.)); database: APORON DB-FU3.0 (Techno Suruga Laboratory Co.); international base sequence database: (GeneBank/DDBJ/EMBL).

(Physiological Characteristics Tests)

The test methods were based on Barnett et al. (2000) and Kurtzman & Fell (1998), with culture being performed at 25° C., except for the temperature endurance test. Tests of the physiological characteristics shown in Table 3 were performed. The results are shown in Table 3.

TABLE 3

Cultural and biochemical characteristics of Strain TK1

| Characterisities | | Growth | Characterisities | Growth |
|---|---|---|---|---|
| D-Glucose | A | + | D-Glucuronate | − |
| | F | + | Glycerol | S |

TABLE 3-continued

Cultural and biochemical characteristics of Strain TK1

| Characterisities | | Growth | Characterisities | Growth |
|---|---|---|---|---|
| Maltose | A | − | DL-Lactate | S |
|  | F | − | Erythritol | − |
| Sucrose | A | + | Succinate | L |
|  | F | + | Trehalose | − |
| Galactose | A | + | D-Glucitol | + |
|  | F | W | Ethanol | S |
| Melibiose |  | − | α-Methyl-D-glucoside | − |
| D-mannitol |  | S | Nitrate | − |
| Lactose |  | − | Nitrite | − |
| Inositol |  | − | Ethylamine | S |
| L-Sorbitol |  | − | 35° C. | − |
| Raffinose |  | L | 37° C. | − |
| 2-Keto-D-gluconate |  | S | 0.1% cycloheximide | + |
| D-Glucosamine |  | − | 50% (w/v) D-glucose | + |
| Melezitose |  | − | 60% (w/v) D-glucose | S |
| D-Gluconate |  | S | 10% NaCl | S |
| D-Ribose |  | − | 16% NaCl | − |

A: assimilation;
F: fermentation;
+: positive;
L: delayed positeive;
W: weakly positive;
S: slow positive;
−: negative (Simple Morphological Observation)

Simple morphological observation was performed with an optical microscope (BX, Olympus, Tokyo). Results are shown in FIG. 1. The bar is 5 μm.

(Identification of TK1 Strain)

As a result of a base sequence homology search on the APORON DB-FU employing BLAST (Altschul, S. F. et al., (1990), J. Mol. Biol. 215; 403-410), the 26S rDNA-D1/D2 base sequence of the Strain TK1 strain showed 100% homology with that of NRRL YB-4819, which is the type strain of *Wickerhamia fluorescens*, one species of ascomycetous yeast. In homology searches on international base sequence databases such as GeneBank/DDBJ/EMBL as well, the 26S rDNA-D1/D2 base sequence of the Strain TK1 strain showed 100% homology with that of the NRR YB-4819 strain of *W. fluorescens*.

As a result of simple morphological observation, it was found that the nutritive cells of the Strain TK1 strain are lemon-shaped, egg-shaped, or eggplant-shaped; and that propagation occurs through bipolar budding, with broad budding regions, and formation of pseudohypha (FIG. 1). On the 19$^{th}$ day after initiating culture, it was confirmed that sports cap-shaped ascospores had formed inside an ascus. This morphological observation is consistent with morphological observation of *W. fluorescens* (Kurtzman, C. P., Fell, J. W., The Yeasts: A Taxonomic Study, 4$^{th}$ edition, Elsevier, Amsterdam, Netherlands).

As a result of tests of physiological and biochemical characteristics, the Strain TK1 strain shows sugar fermentation, does not utilize inositol as a carbon source, and does not utilize nitrate as a nitrogen source (Table 3). This is consistent with the features of the genus *Wickerhamia* (Kurtzman, C. P., Fell, J. W., The Yeasts: A Taxonomic Study, 4$^{th}$ edition, Elsevier, Amsterdam, Netherlands).

The above results of tests of physiological characteristics and morphological observation support the results for the 26S rDNA-D1/D2 base sequence. Therefore, the Strain TK1 strain is presumed to belong to *W. fluorescens*, and the strain was named *W. fluorescens* TK1. This novel microorganism was deposited on 13 Dec. 2010 with the Patent Organism Depository (IPOD) of the National Institute of Advanced Industrial Science and Technology (Central 6, Tsukuba Center, 1-1-1 Higashi, Tsukuba, Ibaraki 305-8566), as *Wickerhamia fluorescens* TK1 (FERM AP-22048).

Figure 2:
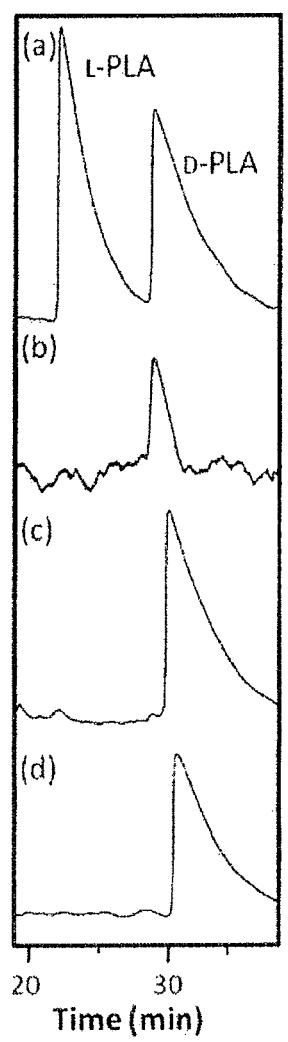
FIG. 2 "HPLC profiles of L-phenyllactate and D-phenyllactate" (a) is a D-3-phenyllactate and L-3-phenyllactate preparation/L-phenyllactate eluted as an initial peak at 22.4 min, and D-phenyllactate eluted at 31.7 min; (b) is the supernatant after MM medium culture of *W. fluorescens* TK1; (c) the supernatant after GPAMM medium culture of *W. fluorescens* TK1; and (d) is a phenylpyruvate substrate treated with an enzyme derived from the main strain.

(3) Optical Isomerism of 3-phenyllactate Produced by the *W. Fluorescens* TK1 Strain The optical isomerism of 3-phenyllactate produced by the *W. fluorescens* TK1 strain was determined. The culture supernatant was subjected to chiral analysis (on a Nucleosil Chiral-1 column) as mentioned above (FIG. 2). As a result, the produced 3-phenyllactate showed identical retention time to D-3-phenyllactate, and gave peaks different than L-3-phenyllactate. It was therefore clear that the *W. fluorescens* TK1 strain produces D-3-phenyllactate in an enantiomer-selective manner.

FIG. 2(a) shows the profiles of D-3-phenyllactate and L-3-phenyllactate preparations, (b) that of the supernatant of MM medium after culture of the present strain, (c) that of the supernatant of GPAMM medium after culture of the present strain, and (d) that of a phenylpyruvate substrate treated with the enzyme obtained from the present strain.

(4) D-3-Phenyllactate Productivity when the *W. Fluorescens* TK1 Strain is Cultured in MM Medium (Minimal Medium)

The *W. fluorescens* TK1 strain, brought to an initial cell concentration of 0.2 (O.D. 600), was shake cultured in MM culture medium for 5 days under aerobic conditions (vaned flask, 100 mL), sampling the medium supernatant over time. As a result, cell propagation entered a stationary phase subsequent to the 24 hour mark after initiating culture. The quantity of D-3-phenyllactate produced continued to increase even after entering the stationary phase, and by the 96$^{th}$ hour after initiating culture, 0.1 mM of D-3-phenyllactate had been produced in the culture medium (FIG. 3).

Figure 3:
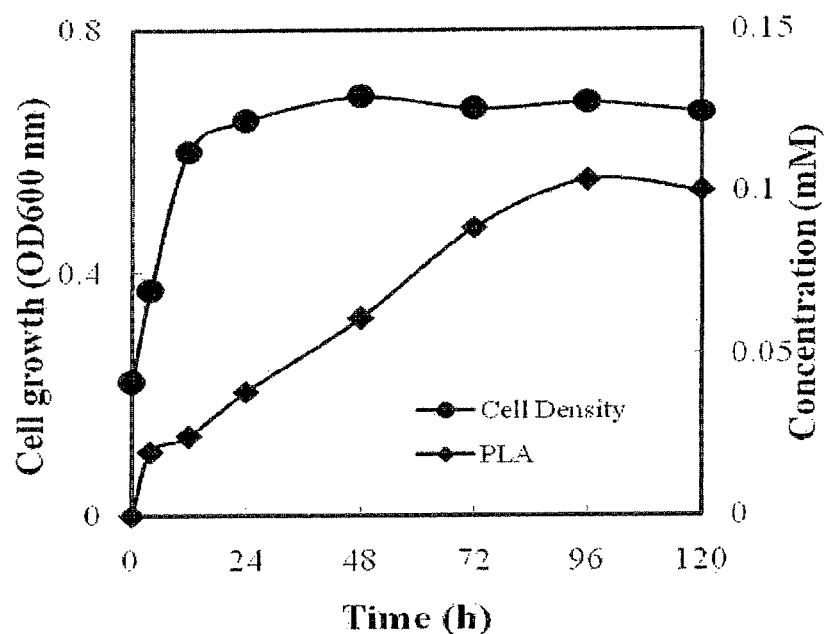
FIG. 3 Shows quantity of cells and produced quantity of optically active phenyllactate during culture of the *W. fluorescens* TK1 strain.
Figure 4:
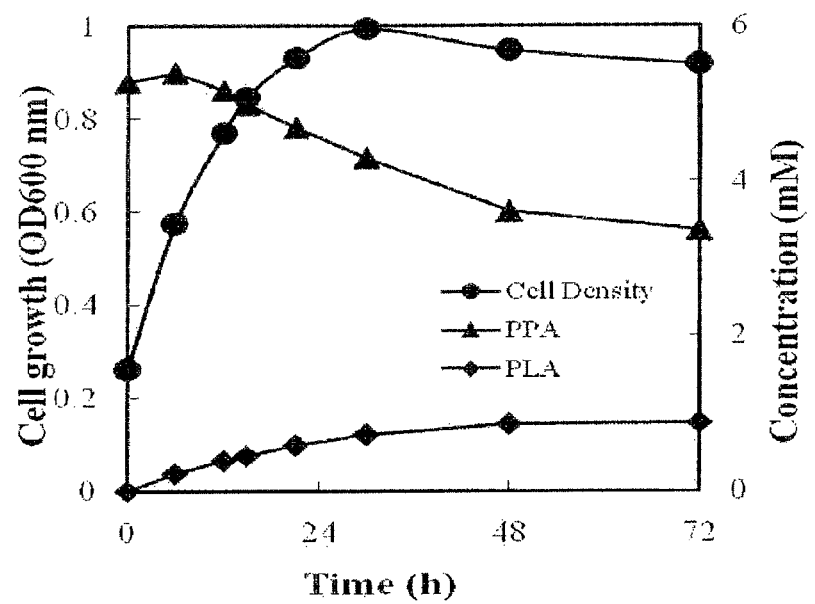
FIG. 4 Shows quantity of cells, produced quantity of optically active phenyllactate (PLA), and produced quantity of phenylpyruvate (PPA) during culture of the *W. fluorescens* TK1 strain.
Figure 5:
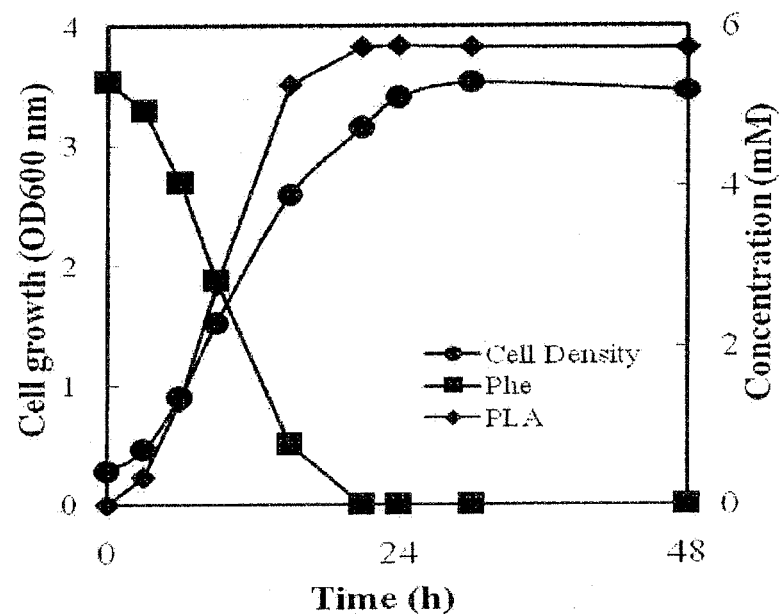
FIG. 5 Shows quantity of cells, produced quantity of optically active phenyllactate (PLA), and produced quantity of L-phenylalanine (Phe) during culture of the *W. fluorescens* TK1 strain.

In FIGS. 3-5, "cell density" shows the quantity of cells, "PLA" shows the D-3-phenyllactate concentration, "PPA" shows the phenylpyruvate concentration, and "Phe" shows L-phenylalanine.

(5) Effect of Phenylalanine and Phenylpyruvic Acid on Production of D-3-phenyllactate The *W. fluorescens* TK1 strain, brought to an initial cell concentration of 0.2 (O.D. 600), was shake cultured under aerobic conditions for 2 days and 3 days, respectively, in a GPAMM culture medium of phenylpyruvic acid added to MM culture medium (Table 4), and in a GPMM culture medium of L-phenylalanine added to MM culture medium (Table 5) (vaned flask, 100 mL), sampling the medium supernatant over time, and measuring the quantity of D-3-phenyllactate produced by the present strain (FIGS. 4 and 5)

TABLE 4

| GPAMM medium | |
|---|---|
| D-Glucose | 10.0 g |
| Phenypyruvic acid | 5.0 mM |
| NaNO$_3$ | 6.0 g |
| KCl | 0.52 g |
| MgSO$_4$•7H$_2$O | 0.52 g |
| KH$_2$PO$_4$ | 1.52 g |
| *Hutner's trace elements | 2 ml |
| per liter (pH 6.5) | |

TABLE 5

| GPMM medium | |
|---|---|
| D-Glucose | 10.0 g |
| L-Phenylalanine | 5.0 mM |

TABLE 5-continued

GPMM medium

| | |
|---|---|
| NaNO$_3$ | 6.0 g |
| KCl | 0.52 g |
| MgSO$_4$·7H$_2$O | 0.52 g |
| KH$_2$PO$_4$ | 1.52 g |
| *Hutner's trace elements per liter (pH 6.5) | 2 ml |

As a result, when L-phenylalanine was added to the culture medium, the quantity of cells of the *W. fluorescens* TK1 strain was 5.1-fold that when none was added, and D-3-phenyllactate production was 57.5-fold. When phenylpyruvic acid was added, the quantity of cells was 1.5-fold, and D-3-phenyllactate production was 8.9-fold.

In a case in which 5 mM of L-phenylalanine was added to the culture medium, L-phenylalanine ceased to be detected after 24 hours of culture, and instead an equal level (5.7 mM) of D-3-phenyllactate had accumulated. This led to the conclusion that the present strain converts L-phenylalanine to D-3-phenyllactate. Specifically, it is thought that the present strain has an enzyme that produces optically active phenyllactate.

Moreover, cell growth was observed in conjunction with the decrease in L-phenylalanine and production of D-3-phenyllactate. When the quantity of cell growth is compared for GPMM culture medium to which L-phenylalanine has been added (FIG. 4), culture employing MM culture medium with no L-phenylalanine added (FIG. 3), and culture employing GPAMM culture medium to which phenylpyruvic acid has been added (FIG. 4), it is greatest in culture employing GPMM culture medium to which L-phenylalanine has been added.

It is thought that this is caused by promotion of cell growth due to utilization of ammonia liberated from the amino groups of L-phenylalanine, as a nitrogen source.

(6) Preparation of Cell-Free Extract Containing Enzyme Produced by the *W. Fluorescens* TK1 Strain For each 1.0 g of wet cell weight, 20 mL of phosphate buffer containing 2.5 g of aluminum oxide, 0.2 mM each of the protease inhibitors phenylmethylsulfonyl fluoride (PMSF) and N-tosyl-L-phenylalanylchlormethyl ketone (TPCK), 10% glycerol and 1 mM of dithiothreitol (DTT) was added, rupturing the cells with a pestle and a mortar. An equal quantity of the same buffer was added to the ruptured cell solution, which was then centrifugally separated at 15000×g. The culture supernatant obtained thereby was taken as a cell-free extract. The above procedure was performed in ice water.

Figure 6:
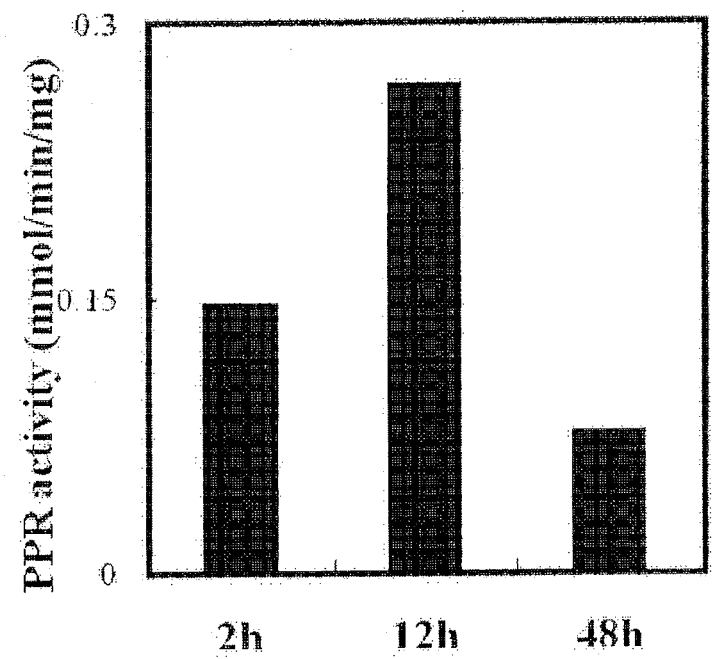
FIG. 6 Shows phenylpyruvate reductase activity at times (2, 12, and 48 hours) during culture of the *W. fluorescens* TK1 strain.

(7) Investigation of Conditions of Recovery of PPR Enzyme from Cell-Free Extract Prior to purifying the PPR enzyme, which is an enzyme that catalyzes reduction of phenylpyruvate to D-3-phenyllactate (phenylpyruvate reductase), the relationship between the duration of culture of the strain during culture, and the PPR activity in the cell-free extract, was investigated. Having prepared cell-free extracts from cells at 4, 12, and 48 hours after initiating culture in a GPMM culture medium, the PRR activity at 12 hour mark during culture was compared with that at the 4 hour mark and the 48 hour mark, and found to be 1.8-fold and 3.4-fold, respectively (see FIG. 6).

Based on the above result, it was decided to use cells cultured for 12 hours, for purification purposes. The fact that the period subsequent to the 12 hour point after initiating culture coincides with the time that 3-phenyllactate is produced suggests the possibility that the PPR enzyme is involved in production of 3-phenyllactate.

(8) Investigation of Optimum pH for PPR Enzyme

Figure 7:
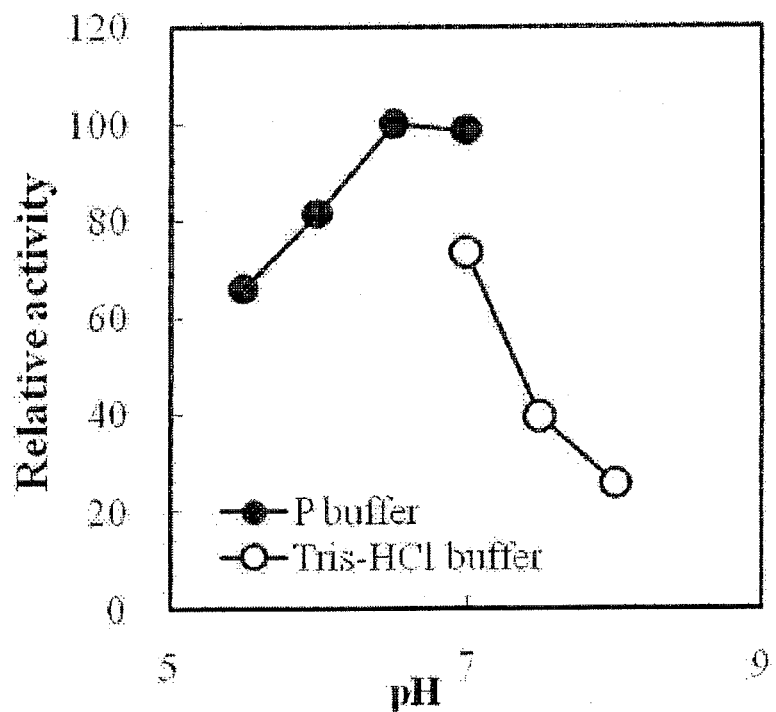
FIG. 7 Shows PPR activity (relative activity) of PPR from the *W. fluorescens* TK1 strain at each of several pH levels (Tris-HCl buffer (pH 7, 7.5, 8), phosphate buffer (pH 5.5, 6, 6.5, 7), assigning a value of 100 to PPR activity at pH 6.5.

PPR activity was measured, employing as the reaction solution buffers of different pH, specifically, Tris-HCl buffer of pH 5.5-8 (pH, 7, 7.5, 8) and phosphate buffer (pH 5.5, 6, 6.5, 7), and the optimum pH for the PPR enzyme reaction was investigated. The highest activity was detected at pH 6.5 (FIG. 7). This indicates that the optimum pH for the PPR enzyme reaction is 6.5, and subsequent activity measurements were performed at pH 6.5.

(9) Preparation of PPR Enzyme Derived from the *W. Fluorescens* TK1 Strain

A cell free extract was prepared as discussed above, and the cell free extract was centrifugally separated for 1 hour at 100,000×g.

Furthermore, as shown below, the centrifugally separated cell free extract was purified through various chromatographic separations on a butyl shepharose column, a 2,5'-ADP-sepharose column, and then a MonoQ HR 5/5 column, to obtain the PPR enzyme.

(Butyl Shepharose Column)

Ammonium sulfate was added to a 20% level to the centrifugally separated cell free extract. A wash buffer (10% glycerol, 1 mM dithiothreitol (DTT), 20 mM phosphate buffer, 20% (NH$_4$)$_2$SO$_4$, pH 7) equivalent to 5-fold the column capacity was flowed through the column to perform equilibration. The prepared sample was run through the column, and elution was performed with a linear ammonium sulfate concentration gradient (20%-0%) to obtain an active fraction.

(2'5'-ADP-Sepharose Column)

The active fraction obtained above was dialyzed overnight with a dialysis buffer (10% glycerol, 1 mM DTT, 20 mM phosphate buffer, pH 7). This sample was run through a 2,5'-ADP-sepharose column equilibrated by flowing a 5-fold quantity of a wash buffer (10% glycerol, 1 mM dithiothreitol (DTT), 20 mM phosphate buffer, pH 7) therethrough. The elution was performed with an elution buffer (10% glycerol, 1 mM DTT, 0.1-1 mL NADP$^+$, 20 mM phosphate buffer, pH 7) to obtain an active fraction.

(MonoQ HR 5/5 Column)

The active fraction obtained above was run through a MonoQ HR 5/5 column (GE Healthcare) equilibrated with an equilibration buffer (10% glycerol, 1 mM DTT, 20 mM phosphate buffer, pH 7) and elution was performed with a linear NaCl concentration gradient (0%-15%).

(Method for Measuring PPR Activity)

For PPR activity measurement, an enzyme reaction solution of 50 mM phosphate buffer (pH 6.5), 2 mM phenylpyruvic acid, and 0.1 mM NADPH was added to the sample (an enzyme solution, cell free extract, or the like) to initiate a reaction. The reaction temperature was 25° C. Activity was quantified through measurement, employing an ultraviolet/visible light spectrophotometer (Beckman-Coulter DU-800), of the decrease in adsorption of the 340 nM wavelength by NADPH generated in association with the reaction. The molar extinction coefficient of absorption of the 340 nM wavelength by NADPH was 6.2 mM$^{-1}$·cm$^{-1}$.

(Method for Measuring Phenylalanine Aminotransferase (PAT) Activity)

For PAT activity measurement, an enzyme reaction solution of 50 mM phosphate buffer (pH 6.5), 10 mM L-phenylalanine, 2.5 mM 2-oxoglutaric acid, and 12.5 μM pridoxal phosphate was added to the sample (an enzyme solution, cell free extract, or the like) to initiate a reaction. The reaction temperature was 37° C. and the reaction time was 30 minutes. The reaction was brought to completion by adding 800 μL of 2 N NaOH. Activity was quantified through measurement of the increase in adsorption of the 320 nM wavelength by phenylpyruvate generated in association with the reaction. The molar extinction coefficient of absorption by phenylpyruvate was 17.5 mM$^{-1}$·cm$^{-1}$ (Whitaker, R. J. et al., J. Biol. Chem. (1982), 257, 3550-3556).

(Quantification of PPR Molecular Mass)

Measurements of PPR molecular mass were performed by gel filtration and/or SDS-PAGE with 12.5% polyacrylamide gel.

When employing the SDS-polyacrylamide gel electrophoresis method, the method of Laemmli et al. was followed.

When employing the gel filtration method, a PPR enzyme sample concentrated with polyethylene glycol 20,000 was run through a Superose 6 10/300 equilibrated beforehand with an elution buffer (10% glycerol, 1 mM DTT, 20 mM phosphate buffer, 0.15 mL NaCl, pH 7), and eluted with an amount of elution buffer equal to the column capacity.

As the standard proteins, bovine serum albumen (M.W. 67,000), chymotrypsinogen (M.W. 25,000), α-amylase (M.W. 45,000), and β-amylase (M.W. 200,000) were employed.

The total amount of protein in a cell free extract prepared from 30 g of cells was 592.2 mg, and total activity of D-3-phenyllactate production was 190.8 μmol/mL. That is, it was confirmed that phenylpyruvate reductase was present in the cell free extract.

As a result of sequential loading of the soluble fraction obtained by centrifugal separation thereof onto butyl sepharose (hydrophobic column), 2'5'-ADP-sepharose (affinity column), and Mono Q HR 5/5 (strong cation exchange column) columns in the manner described above, the specific activity of the PPR enzyme could be concentrated up to 2260-fold, and the PPR enzyme could be purified at 41% yield (Table 6).

Figure 8:
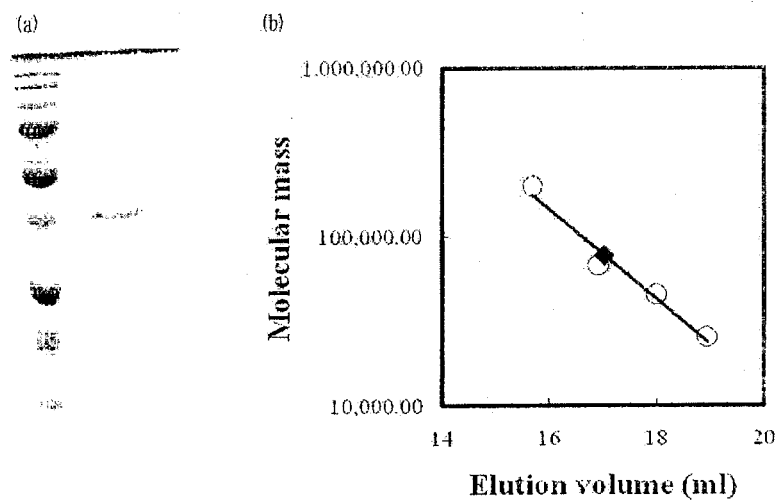
FIG. 8 "PPR molecular mass" (a) shows SDS-PAGE electrophoresis analysis of the enzyme PPR (right side); and (b) shows gel filtration analysis of the enzyme PPR (black trapezoidal shapes).

As a result of subjecting the purified PPR enzyme to SDS-PAGE, a single band was observed, and the molecular mass was 40,000 (FIG. 8). As the molecular mass of the purified PPR enzyme was estimated at 80,000 by the gel filtration method, it became clear that the PPR enzyme forms a homodimer (FIG. 8).

TABLE 6

Purification summary of PPR from *Wickerhamia fluorescens* TK1

| Purification procedure | Total protein (mg) | Total activity (μmol/min) | Specific activity (μmol/min/mg) | Yield (%) | Purification (fold) |
|---|---|---|---|---|---|
| Cell free extract | 592.2 | 190.8 | 0.3 | 100 | 1 |
| 100000 × g supernatant | 514.2 | 233.0 | 0.5 | 122 | 1 |
| Butyl-Sepharose | 23.3 | 193.5 | 8.3 | 101 | 26 |
| 2'5'-ADP Sepharose | 5.4 | 129.0 | 23.8 | 68 | 74 |
| Mono Q HR 5/5 | 0.1 | 77.4 | 727.0 | 41 | 2260 |

(10) Properties of Enzyme Produced by the *W. Fluorescens* TK1 Strain (Enzymological Analysis of PPR)

The PPR enzyme reacts with phenylpyruvate in an NADPH-dependent fashion, producing D-3-phenyllactate, a fact confirmed by the HPLC measurement method discussed above.

As it was confirmed that 2 mM of D-3-phenyllactate is produced from 2 mM of phenylpyruvate and 2 mM of NADPH, the reaction has been shown to have the following stoichiometry.

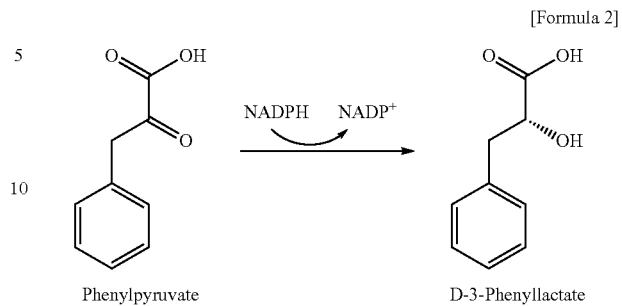

(Scheme 1)

Phenylpyruvate → D-3-Phenyllactate (Scheme 2)

4-hydroxyphenylpyruvate → 4-hydroxyphenyllactate

Due to the failure of an enzyme reaction to arise when a combination of D-3-phenyllactate, L-3-phenyllactate, NAD$^+$, and NADP$^+$ is employed as the substrate, the reaction of the PPR enzyme has been shown to be an irreversible reaction.

When NADPH was utilized as a coenzyme, the PPR enzyme reduced phenylpyruvate, 4-hydroxyphenylpyruvate, glyoxylate, and hydroxypyruvate (Scheme 1 and Scheme 2).

The $k_{cat}/K_m$ value at this time was highest when the substrate was phenylpyruvate, in which case it was 373 s$^{-1}$mM$^{-1}$ (Table 7).

The $k_{cat}/K_m$ value when NADH is the coenzyme was 330 s$^{-1}$mM$^{-1}$, a low value which is 1/31 that when NADPH is the coenzyme (10143 s$^{-1}$mM$^{-1}$). Therefore, while it is possible for either NADH or NAPDH to be used as a coenzyme, specificity to NADPH has been shown to be higher.

TABLE 7

Kinetic properties of PPR

| Variable substrate | Fixed substrate | $K_m$ (mM) | $k_{cat}$ (s$^{-1}$) | $k_{cat}/K_m$ (s$^{-1}$mM$^{-1}$) |
|---|---|---|---|---|
| Phenylpyruvate | NADPH | 0.40 ± 0.07 | 149 ± 12 | 373 |
| Glyoxylate | NADPH | 18.9 ± 5.8 | 18.9 ± 3.4 | 1.00 |
| Hydroxy-pyruvate | NADPH | 3.46 ± 0.83 | 9.14 ± 0.70 | 2.64 |
| Pyruvate | NADPH | ND$^a$ | ND | ND |
| Oxaloacetate | NADPH | ND | ND | ND |
| NADPH | Phenylpyruvate | 0.01 ± 0.00 | 121 ± 2 | 10143 |
| NADH | Phenylpyruvate | 0.10 ± 0.04 | 31.4 ± 7.1 | 330 |

*Not detectable (Effects of Metal Ions and Inhibitors)

Various metal ions and inhibitors were added to the reaction system, to respective final concentrations of 1 mM, and PPR activity was measured. Declines in PPR activity were observed with the metal ions $Cu^{2+}$, $Zn^{2+}$, $Fe^{2+}$, $WO^{2-}$, and $Hg^{2+}$ (Table 8), showing that these inhibit PPR activity.

TABLE 8

Effects of various compounds and detergents on the activity of PPR

| Inhibitor | Relative activity[a] (%) |
|---|---|
| None | 100 |
| $MnCl_2$ | 103 |
| $MgSO_4$ | 92 |
| $CuSO_4$ | 0 |
| $ZnSO_4$ | 9 |
| $FeCl_2$ | 0 |
| $CaCl_2$ | 90 |
| $NiCl_2$ | 63 |
| $Na_2MoO_4$ | 89 |
| $Na_2WO_4$ | 0 |
| $CoCl_2$ | 61 |
| $HgCl_2$ | 0 |
| Tween 80[b] | 52 |
| TritonX-100[b] | 82 |
| EDTA | 84 |
| 2-Mercaptoethanol[b] | 64 |

[a]Final concentration of compounds was 1 mM unless otherwise stated.
[b]Final concentration were 0.5%.

(Properties of D-3-phenyllactate-Producing Strains and of PPR Produced Thereby)

As the result of a search for D-3-phenyllactate-producing strains, the ascomycetous yeast *W. fluorescens* TK1 strain was found to produce 0.1 mM of D-3-phenyllactate in culture supernatant, and it was therefore concluded that screening of a novel D-3-phenyllactate-producing strain had been successful. During culture in similar fashion, but adding L-phenylalanine to the culture medium, D-3-phenyllactate was produced in a production amount of 5.7 mM. *G. candidum*, which has also been reported to produce D-3-phenyllactate, was reported to have produced 3-phenyllactate in an amount of 3.6-6.0 mM when cultured in a TSBYE medium in a jar fermenter (Non-patent Reference 2), while lactobacilli were reported to produce it in an amount of 0.57 mM when an MRS culture medium was employed (J. Biochem. 2005 138, 741-74915)). Moreover, *Lactobacillus* Sp. SK007 produced 5.2 mM of D-3-phenyllactate when 6 mM of the 3-phenyllactate precursor phenylpyruvate was added to the culture medium (Li, X. et al., Biotechnol. Lett. (2007) 29, 593-597), while with *L. plantarum* TMW1.468 or *L. sanfranciscensis* DSM20451, production of 0.04-0.08 mM was observed when 50 mM of phenylalanine was added to the culture medium (Vermuelen, N. et al., J. Agric. Food Chem. (2006), 54, 3832-3839). The above results show that the *W. fluorescens* TK1 strain has the capability to produce relatively high D-3-phenyllactate, without precision control of culture conditions by employing a jar fermenter or the like.

Moreover, the *W. fluorescens* TK1 strain produced D-3-phenyllactate in enantiomer-selective fashion. There are instances in which physiological activity of chemical products or pharmaceuticals differs between enantiomers, of which thalidomide is a representative example. Therefore, for chiral molecules, enantiomer-selective manufacture is needed. Therefore, the fact that the strain produces D-3-phenyllactate at high enantiomer selectivity is thought to have considerable significance in terms of utilizing the compound in pharmaceutical feedstocks and the like.

The PPR activity of the purified cells, when the substrate is phenylpyruvate, is a $k_{cat}/K_m$ value of 373 $s^{-1}mM^{-1}$. This value is a higher value than the molecular activity of any of several reported to date, namely, DLDH from *Lactobacillus pentosus* JCM1558 (Non-patent Reference 15) or *Lactobacillus plantarum* ATCC 8041 (Taguchi, H.; Ohta, T., J. Biol. Chem. (1991) 266, 12588-12594), or GRHPR from *Rhizobium etli* CFN 42 (Fauvart, M., et al., Biochimica et Biophysica Acta 1774 (2007) 1092-1098) (Table 9).

Moreover, D-4-hydroxyphenyllactase dehydrogenase from *Candida maltosa*, an enzyme which acts on a substrate of the only fungus-derived phenylpyruvate purified to date, shows high affinity for phenylpyruvate and 4-hydroxyphenylpyruvate comparable to that of the *W. fluorescens* TK1 strain. However, D-4-hydroxyphenyllactase dehydrogenase requires the cofactor $Mn^{2+}$, and its molecular mass of 250,000-280,000 is very high in comparison to the molecular mass of PPR. Moreover, the PPR enzyme has highest affinity for phenylpyruvate, whereas D-4-hydroxyphenyllactase dehydrogenase has higher affinity for 4-hydroxyphenylpyruvate, so the two are concluded to be different enzymes.

TABLE 9

Substrate specificities for phenylpyruvate of *W. fluorescens* TK1 and other organisms

| Strain | PPA (mM) | $k_{cat}$ ($s^{-1}$) | $k_{cat}/K_m$ ($s^{-1}mM^{-1}$) |
|---|---|---|---|
| *W. fluorescens* TK1 | 0.4 | 149 | 373 |
| *Lactobacillus pentosus* JCM1558 | 0.8 | 40 | 50 |
| *Lactobacillus planarum* SK002 | 20 | 22 | 1.1 |
| *Rhizobium etli* CFN 42 | 0.8 | 0.37 | 0.46 |

Non-patent Reference 15
Taguchi, H.; Ohta, T., J. Biol. Chem. (1991) 266, 12588-12594 Fauvart, M., et al., Biochimica et Biophysica Acta 1774 (2007) 1092-1098

Example 2

Cloning of PPR Gene and Expression in Coliform Bacteria (1) Strain Used

The 3-phenyllactate-producing *W. fluorescens* TK1 strain was employed.

*E. coli* Origami B (DE3) was employed as the host for PPR expression. The *E. coli* JM 109 strain was employed during building of the plasmid.

(2) Culture Method

From a YPD agar medium in which cells were grown in advance, one platinum loop of cells was inoculated into 10 mL of the aforedescribed YPD culture medium aliquoted into a test tube with a total capacity of 50 mL, and shake cultured for 2 days at 30° C., 120 rpm. Cells were harvested from the pre-culture broth by centrifugal separation, and the precipitate was washed with physiological saline. This was inoculated into a vaned flask of total capacity of 500 mL containing 150 mL of GPMM culture medium, and shake cultured for 2 days at 30° C., 120 rpm under anaerobic conditions.

(3) Analysis of N-Terminal Amino Acid Sequence of PPR Enzyme
(Blotting)

Two sheets of filter paper were immersed in solution A (0.3 M Tris, 5% methanol), one sheet was immersed in solution B (25 mM Tris, 5% methanol), and three sheets were immersed in solution C (25 mM Tris, 40 mM 6-aminocaproic acid, 5% methanol), respectively. After the purified PPR underwent electrophoresis by SDS-PAGE, the filter papers immersed in the respective solutions were stacked with gel and electrically transferred to a polyvinylidene difluoride (PVDF) membrane (AE-6665 by ATTO) by a transfer device (HorizeBLOT AE-6670P/N by ATTO).

(Protein Sequencing)

The target band was cut from the dried PVDF membrane, and loaded into an amino acid analyzer (Applied Biosystems Procise 494 cLC).

(4) Determination of Internal Amino Acid Sequence of PPR Enzyme

The PPR enzyme purified through electrophoresis by SDS-PAGE was cut from the gel, and the gel digested with trypsin. The trypsin-digested peptide was subjected to Matrix-Assisted Laser Desorption/Ionization Time-of-Flight (MALDI-TOF/MS) (AXIMA™, AXIMA™-QIT Shimazu), and the amino sequence was determined on the basis of the fragment information obtained thereby.

(5) Preparation of cDNA

W. fluorescens TK1 strain cultured in GPMM medium was suspended in a rupture buffer (500 mM NaCl, 200 mM Tris-HCl (pH 7.5), 10 mM EDTA, 1% SDS), to which were added a half-quantity of glass beads and an equal quantity of phenol/chloroform/isoamyl alcohol (25:24:1) (phenochlo treatment). Stirring by a vortex was followed by centrifugal separation, recovering the supernatant and treating with Dnase. Phenol/chloroform/isoamyl alcohol extraction was repeated twice, and a 2.5-fold quantity of ethanol and a ¹/₁₀-fold quantity of 3 M sodium acetate were added (ethanol precipitation). After centrifugal separation, the precipitate was suspended in 450 µL of RLC (included with the RNeasy™ Plant Mini Kit) and 4.5 µL of 2-mercaptoethanol. Subsequent steps followed the RNeasy™ Plant Mini Kit protocol. The cDNA was synthesized from the prepared RNA and PrimeScript™ Reverse Transcriptase.

(6) Preparation of Total DNA

W. fluorescens TK1 strain cultured overnight in YPD medium was suspended in a rupture buffer (100 mM NaCl, 10 mM Tris-HCl (pH 8.0), 1 mM EDTA, 2% TritonX-100), to which were added a half-quantity of glass beads and an equal quantity of phenol/chloroform/isoamyl alcohol (25:24:1) (phenochlo treatment). Stirring by a vortex was followed by centrifugal separation, and recovery of the supernatant. Phenol/chloroform/isoamyl alcohol extraction was repeated twice, and a 2.5-fold quantity of ethanol and a ¹/₁₀-fold quantity of 3 M sodium acetate were added (ethanol precipitation). After centrifugal separation, the precipitate was washed with 70% ethanol. After discarding the 70% ethanol and drying with an aspirator, the precipitate was suspended in sterile water to which RNase was added.

(7) Cloning (PCR Method)

To a 50 µL PCR reaction system were added 1 µL of the cDNA obtained above (as the template), 5 µL of 10XKOD-Plus-buffer (TOYOBO), 4 µL of 2.5 mM (each) dNTP, primer NP (5'-ATGAARAARCCNCAGGT-3') (SEQ ID NO: 10), Oligo dT (5'-TTTTTTTTTTTTTTTTTTTT-3') (SEQ ID NO: 11), 1 µL of KOD-Plus-DNA Polymerase (TOYOBO), and 2 µL of 25 mM MgS04. After performing treatment of 96° C. 30 s, 50° C. 30 s, 68° C. 3 min on the reaction system 35 times, an elongation reaction at 68° C. 5 min was brought about (primary PCR). 1 µL of PCR product (as the template), 5 µL of 10xEx Taq buffer (TaKaRa), 4 µL of 2.5 mM (each) dNTP, primer NP (SEQ ID NO: 10), primer 2427P (5'-GGYTCYT-CYTCRAANACRTT-3') (SEQ ID NO: 12), and 0.5 µL Ex Taq Polymerase (TaKaRa) were added. After performing treatment of 96° C. 15 s, 56° C. 20 s, 72° C. 1 min 35 times, an elongation reaction at 72° C. 5 min was brought about (secondary PCR).

(Total Length Analysis of PPR Gene)

On the basis of the prepared total RNA, PPF 5'-terminal cDNA was synthesized with the 5' RACE System for Rapid Amplification of cDNA Ends (RACE), Version 2.0 (Invitrogen Co., CA). Using the obtained cDNA as the template, nested PCR was performed with the adaptor oligonucleotide included in the kit, and primers specific to the gene coding for PPR (GSP1 (5'-TGAAAATGCGTTAGTATGTGGAT-3') (SEQ ID NO: 13), GSP2 (5'-TGCCTTTGCTGCTTTGAAT-GTAT-3') (SEQ ID NO: 14)). PCR reaction conditions involved performing treatment of 96° C. 15 s, 56° C. 20 s, 72° C. 1 min 35 times, followed by a 72° C. 5 min elongation reaction. The 200 kp DNA fragment obtained by PCR was recovered by agarose eletrophoresis, and cloned to pGEMT™-T easy (Promega, Madison, Wis.). The DNA sequence of the insert fragment of the plasmid obtained thereby was determined.

For the 3'-terminal, PCR was performed in the same manner as above, with cDNA synthesized by the RACE System for Rapid Amplification of cDNA Ends (Invitrogen Co., CA) as the template, and employing the primer GSP (5'-AACTAC-GAGGTGCTGCC-3') (SEQ ID NO: 13), and the primer GSP nest (5'-GTCCTCCCCAGTTACCATATATAGC-3') (SEQ ID NO: 16. The base sequence of the obtained 270 kb fragment was determined.

(DNA Sequence Analysis)

For sequence analysis of the DNA, a fully automated DNA sequencer (CEQ2000, Beckman Coulter) was employed for the analysis. The method followed the protocol.

(8) Real-Time PCR

The W. fluorescens TK1 strain was cultured for 8 hours at 30° C. in MM culture medium, GPMM culture medium, and GPAMM culture medium, and RNA was prepared from the cells of the cultures obtained thereby. With this as the template, a reverse transcription reaction was performed with the oligo-dT19 primer and Reverse Transcriptase M-MLV (TAKARA BIO, Inc, Japan). The single strand cDNA obtained thereby as the template, employing iQ™ and SYBR™ Green Supermix (Bio-Rad Laboratories Inc., CA), was loaded into the MiniOpticon™ version 3.1 (Bio-Rad Laboratories Inc., CA). The expression level of the pprA gene in the respective cells was represented as a ratio to the expression level of 18S ribosomal RNA.

Expression ratio (pprA)/18SrDNA)= $2^{CT(pprA)-CT(18S\ ribosom)} * C_T$ is the cycle number at which the amplified product accumulated to the point that a detectable fluorescent signal was obtained.

The enzyme pprA (pprART F (5'-ATTTAGCCGCGAT-GAAAGAAC-3') (SEQ ID NO: 17), pprART R (5'-TCG-GCAAAGGCACATCC-3') (SEQ ID NO: 18)) and the 18S ribosome primer (18SRT F (5'-ACCAGGTCCAGACA-CAATAAGG-3') (SEQ ID NO: 19), 18SRT R (5'-AAGCA-GACAAATCACTCCACC-3') (SEQ ID NO: 20) were designed employing the primer 3 primer fabrication software (http://frodo.wi.mit.edu/cgi-bin/primer3/primer3.cgi)

(9) Expression and Purification of Recombinant PPR (rPPR) with Coliform Bacteria (Fabrication of Transformant)

Figure 9:
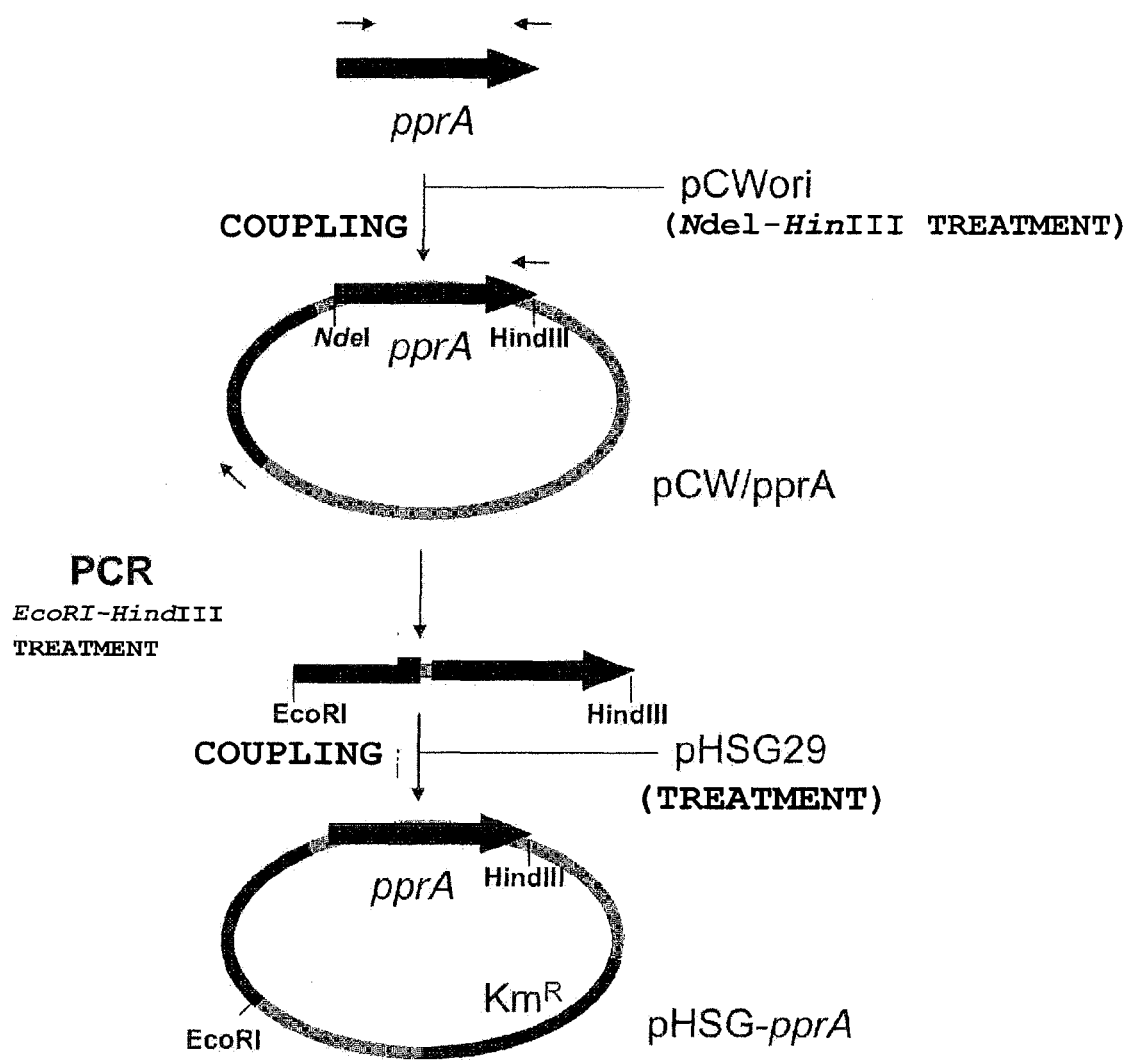
FIG. 9 Shows an example of creation of a plasmid vector containing the ppr gene of the present invention (pprA gene).

Employing single strand cDNA prepared from the RNA of the W. fluorescens TK1 strain, and the primers Nde-PPR (5'-GGGTTTCATATGAAAAAGCCTCAG-3') (SEQ ID NO: 21) and Xho-PPR (5'-CCGCTCGAGAACTACAA-GATT-3') (SEQ ID NO: 22), the cDNA fragment of the pprA gene was amplified through a PCR reaction. A plasmid (pCW-PPR) constructed by linking a fragment obtained through treatment thereof with Nde I, Xho 1 to one from pCWori pre-treated with the same restriction enzymes was introduced into E. coli ATCC31881 (acquired from ATCC) (see FIG. 9 and FIG. 10).

(Induction of Expression)

The recombinant cells obtained thereby were cultured for 12 hours at 37° C. in 10 mL of LB culture medium (LA) containing ampicillin sodium in a final concentration of 100 µg/L. The total quantity was inoculated into 150 mL of LA. After culture for 2 hours at 120 rpm, 37° C., IPTG was added to a final concentration of 1 mM, and the cells were cultured at room temperature for 8 hours, 50 rpm.

(Purification of rPPR)

The cultured cells were harvested, suspended in buffer A (20 mM potassium phosphate (pH 7.0), 10% glycerol, 0.1 mM DTT), and ultrasonically ruptured. The ruptured solution was centrifugally separated for 30 minutes at 15,000 rpm to recover the supernatant (cell free extract). The cell free extract was run through a chelating Sepharose column (Amersham) which beforehand had been induced to adsorb $Ni^{2+}$ and then equilibrated with buffer A containing 300 mM NaCl (buffer C). The fraction eluted by buffer C containing 500 mM imidazole was recovered, dialyzed against buffer A, and employed in the subsequent analysis.

(10) Molecular Descent Analysis (Amino Acid Sequence Alignment)

The National Center for Biotechnology Information (NCBI) database was searched for a sequence having homology with the presumed amino acid sequence of the cloned pprA gene. BLAST was employed at this time. The sequence information obtained thereby was utilized to perform multiple alignment analysis by ClustalW.

(Inference of Phylogenetic Tree)

MEGA 4 was employed for inference of phylogenetic tree. The amino acid sequence employed in creating the phylogenetic tree was acquired from NCBI. Inference of phylogenetic tree was performed by the neighbor joining method, showing estimated bootstrap iterations on the branches.

(11) Determination of N-Terminal Amino Acid Sequence of PPR Enzyme

The purified PPR enzyme (1 µg) was electrophoretically blotted onto a PVDF film, and the amino acid sequence of the N-terminal of the PPR enzyme was analyzed. As a result, the N-terminal amino acid sequence MKKPOVLILGRI of 12 residues of the PPR enzyme was successfully determined (SEQ ID NO: 1).

(12) Acquisition of Internal Amino Acid Sequence of PPR Enzyme

Figure 11:
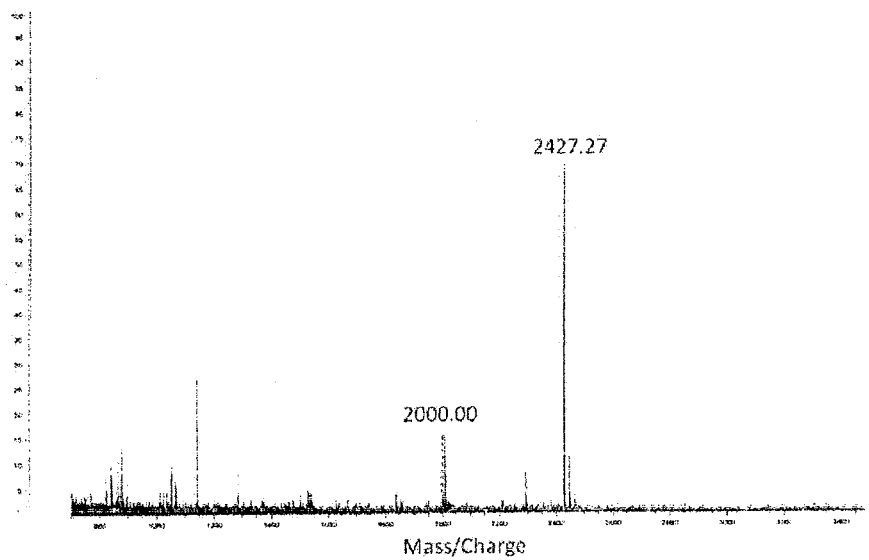
FIG. 11 "MS spectra of MALDI-TOF and MS$^2$ spectra of MALDI-QIT-TOF for one of the trypsin peptide derived from PPR/Positive ion MALDI-TOF mass spectra of PPR derived from *W. fluorescens* NRRLYB-4819" The MS spectra of MALDI-TOF, of internal amino acid sequences of the present invention FIG. 12 "MS spectra of MALDI-TOF and MS$^2$ spectra of MALDI-QIT-TOF for one of the trypsin peptide derived from PPR/MS/MS spectra of mass ion peaks at m/z 2000.0 (a) and 2427.3 (b) shown in panel" MS spectra of MALDI-TOF, of internal amino acid sequences of the present invention. (a) is the amino acid sequence shown by SEQ ID NO: 2; and (b) is the amino acid sequence shown by SEQ ID NO: 3.

After SDS-PAGE, the PPR enzyme was cut from the gel, and in-gel digestion was performed with trypsin. The trypsin-digested peptide obtained thereby was analyzed by MALDI-TOF MS. From among the peptide peaks obtained in the MALDI-TOF MS analysis, two peptides, m/z 2000.00 and m/z 2427.27, were selected, and MALDI-QIT-TOF was employed to perform MS/MS analysis (FIG. 11). De novo sequencing of the amino acid sequence of the trypsin-digested peptide was performed on the basis of the mass fragment peak information obtained thereby, and as a result, the amino acid sequence NIQAIYGNWGGLASFGGFK (SEQ ID NO: 2) of 19 amino acid residues was obtained for the m/z 2000.00 peptide, and the amino acid sequence VAFAALDV-FEEEPFIHPGLIGR (SEQ ID NO: 3) of 22 amino acid residues was obtained for the m/z 2427.27 peptide, respectively (FIG. 12).

(13) Cloning of pprA Gene

Figure 13:
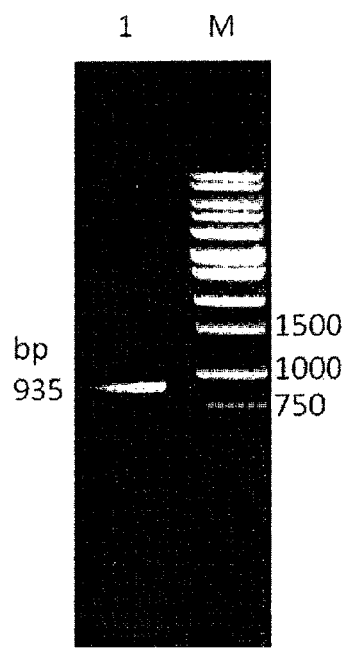
FIG. 13 "Agarose gel electrophoresis of the nested PCR products: Shows agarose gel electrophoresis of 935 bp DNA fragments obtained on the basis of information about N-terminal amino acid sequences (SEQ ID NO: 1) and internal amino acid sequences (SEQ ID NO: 3). 1: PCR products for pprA, M: DNA markers FIG. 14 "Nucleotide sequence of the *W. fluorescens* TK1 PPR gene and its deduced amino acid sequence" Shows the ppr gene derived from the *W. fluorescens* TK1 strain, and the amino acid sequence thereof. Internal amino acid sequences of PPR determined by MALDI-QIT-TOF MS analysis are shown in boxes. Primer NP and Oligo dT positions are shown by arrows. The nested primer 2427P is shown by a dotted line. The termination codon is shown by a star.

The primer NP (SEQ ID NO: 10) and the primer 2427P (SEQ ID NO: 12) were respectively designed on the basis of the information for the N-terminal amino acid sequence (SEQ ID NO: 1) and the internal amino acid sequence m/z 2427.27 (SEQ ID NO: 3). With the cDNA prepared from the *W. fluorescens* TK1 strain as the template, PCR was carried out employing the primer NP (SEQ ID NO: 10) and the primer Oligo dT (SEQ ID NO: 11). Further PCR was then performed with the PCR products as the template, employing the primer NP (SEQ ID NO: 10) and the primer 2427P (SEQ ID NO: 12). As a result, the 935 bp target DNA fragment was amplified (FIG. 13).

Primers were designed on the basis of the amplified DNA sequence, and the base sequences at either terminus of the pprA gene were analyzed by the RACE method. As a result, it was shown that the pprA gene comprises 1,095 bp base pairs coding for 364 residues (FIG. 14: SEQ ID NO 4 and 5). The PPR N-terminal and internal amino acid sequences determined above were discovered within this presumed amino acid sequence. When the sequence amplified by genomic DNA and the sequence amplified by cDNA were compared, it was clear that no intron was present in the pprA gene.

(14) Number of Copies of the pprA Gene on the Chromosome

A Southern blot analysis was performed to ascertain the number of copies of the pprA gene present on the genome of the *W. fluorescens* TK1 strain (FIG. 15). With a DNA fragment containing the sequence of the pprA gene as a probe, Southern hybridization was performed on the total DNA of the *W. fluorescens* TK1 strain treated with restriction enzymes (Hind III, EcoRI, PstI, BamHI). As a result, only a single band was obtained in cases in which the total DNA was treated with any of the restriction enzymes. This shows that only one copy of the pprA gene is present on the genome, and that the purified PPR was expressed by the pprA gene.

(15) Control of Expression of the PPR Enzyme by L-Phenylalanine

The PPR activity of cell free extracts of cells obtained by culturing the *W. fluorescens* TK1 strain in GPMM culture medium (containing D-glucose and L-phenylalanine), GPAMM culture medium (containing D-glucose and phenylpyruvate), and MM culture medium (containing D-glucose), respectively, for 10 hours at 30° C. was measured according to the manner discussed previously (Method for measuring PPR activity). As a result, the PPR activity of the cell free extract of the cells obtained with the GPAMM culture medium to which L-phenylalanine was added was 0.22 µmol/min/mg, which was 3.6-fold higher as compared of the activity observed with culture in the MM culture medium. The level was observed to be 3.0 times higher as compared with that for culture in the GPAMM culture medium to which phenylpyruvate was added (FIG. 16). Employing real-time PCR, the transcription level of the pprA gene by cells obtained through culture of the *W. fluorescens* TK1 strain for 8 hours under comparable conditions was measured. As a result, the transcription level of the pprA gene by cells cultured in the GPMM culture medium to which 5 mM phenylalanine had been added increased 40-fold, as compared with that obtained under conditions employing the MM culture medium, and 18-fold as compared with that obtained under conditions employing the GPAMM culture medium (FIG. 16). The above results show that expression of the pprA gene is induced by phenylalanine.

(16) Expression and Purification of the rPPR Enzyme with Coliform Bacteria (Purification of the rPPR Enzyme)

Figure 17:
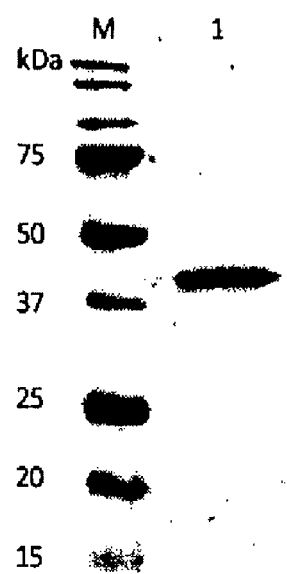
FIG. 17 "SDS-PAGE of purified rPPR (recombinant PPR)" Shows results of SDS-PAGE of the enzyme rPPR produced by coliform bacteria containing the ppr gene. Lane 1: purified rPPR; M: molecular mass standard (Bio-Rad Precision Protein Standard kit). Molecular masses are shown at left.

A plasmid of the cDNA of the pprA gene incorporated into pET21a was introduced into the coliform bacteria Origami B strain. After expression of the PPR enzyme in a form with His attached to the N-terminal, purification was carried out with a chelating Sepharose column (FIG. 17). As a result, a single band was obtained at 40 kDa, showing that the rPPR enzyme was successfully purified.

(Enzymological Properties of rPPR Enzyme)

Figure 10:
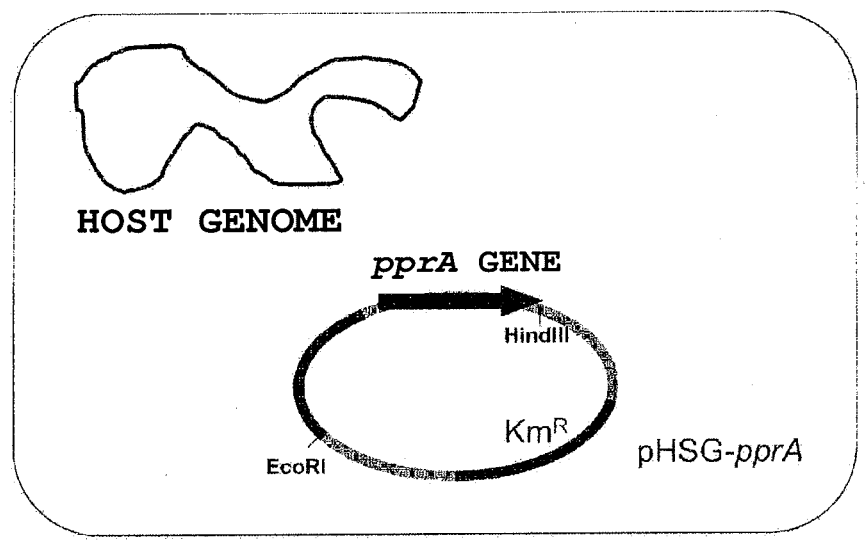
FIG. 10 Shows an example of a transformant containing the ppr gene of the present invention (pprA gene).

Like the PPR enzyme of the *W. fluorescens* TK1 strain, the purified rPPR enzyme is capable of utilizing NADPH as a coenzyme, and of the kcat/Km values observed with phenylpyruvate, 4-hydroxyphenylpyruvate, glyoxalate, and hydroxypyruvate as substrates, the value is highest when phenylpyruvate is the substrate (FIG. 10). No activity is detected with pyruvic acid and oxaloacetic acid substrates (data not shown). This clearly shows that the rPPR enzyme expressed with coliform bacteria has substrate-specificity comparable to that of the PPR enzyme derived from the *W. fluorescens* TK1 strain.

TABLE 10

Kinetic properties of rPPR

| Variable substrate | Fixed substrate | $K_m$ (mM) | $k_{cat}$ (s$^{-1}$) | $k_{cat}/K_m$ (s$^{-1}$mM$^{-1}$) |
|---|---|---|---|---|
| Phenylpyruvate | NADPH | 0.57 ± 0.13 | 177 ± 23 | 313 |
| Glyoxylate | NADPH | 25.2 ± 3.1 | 10.4 ± 0.8 | 0.41 |
| Hydroxy-pyruvate | NADPH | 6.99 ± 2.74 | 6.63 ± 1.04 | 0.95 |
| NADPH | Phenylpyruvate | 0.02 ± 0.07 | 148 ± 19 | 7200 |

(17) Molecular descent analysis of PPR enzyme (Alignment Analysis of PPR Enzyme)

The presumed amino acid sequence of the PPR enzyme shows only 54% homology to the presumed amino acid sequences of genes of unknown function of *Candida dubliniens*, which has the highest homology. Moreover, among amino acid sequences of proteins whose function is known, homology with D-lactate dehydrogenase (DLDH) derived from *L. plantarum* is only 20%, that with recombinant GRHPR from *R. etli* CFN 42 only 25%, and that with hydroxyphenylpyruvate reductase (HPPR) derived from *Solenostemon scutellarioide* only 27%.

Alignment analysis was performed with genes of unknown function of *Candida dubliniens*, DLDH derived from *L. plantarum*, recombinant GRHPR from *R. etli* CFN 42, HPPR derived from *S. scutellarioide*, and the presumed amino acid sequence of the *W. fluorescens* TK1 strain.

NADH/NADPH binding domain was observed at 185-331 in the presumed amino acid sequence of the *W. fluorescens* TK1 strain. Further, the sequence -G-X-G-X-X-G-, thought to be the NADH/NADPH binding motif, was observed in the presumed amino acid sequence of PPR (FIG. 18). Moreover, the 86$^{th}$ valine (V) (V83 in GRHPR) hydrogen-bonding to the oxygen atom of a carboxyl group of a substrate identified as being a substrate binding region in human GRHPR (Booth, M. P. et al., J. Mol. Biol. (2006), 360, 178-189)), the 87$^{th}$ glycine (G) (GRHPR: G274), and the 282$^{nd}$ arginine (R) (GRHPR: G724) hydrogen-bonding to the oxygen atom of a carboxyl group and a carbonyl group of a substrate were conserved in the PPR enzyme. The 329$^{th}$ histidine (H) (GRHPR: H329) residue, which is an acid-base catalyst, and the 311$^{th}$ glutamine (E) (GRHPR: E311) residue, which hydrogen-bonds to the imidazole ring of the H329 residue, are also conserved. As DLDH and GRHPR are enzymes belonging to the D-isomer specific 2-hydroxyacid dehydrogenase superfamily, this suggests that the PPR of the tested strain belongs to the same family.

(Phylogenetic Tree)

Known enzymes belonging to the GRHPR, HPPR, DLDH, formate dehydrogenase (FDH), L-lactate dehydrogenase (LDDH), and malate dehydrogenase (MDH) families, and amino acid sequences of proteins of unknown function that are highly homologous to the PPR enzyme, were screened, and a molecular phylogenic tree was inferred. As a result, PPR was concluded to belong to a different cluster from the LLDH, MDH superfamily, and was classified into D-isomer specific 2-hydroxyacid dehydrogenase superfamily.

In order to perform a more detailed phylogenetic analysis, amino acid sequences of HPPR belonging to the D-isomer specific 2-hydroxyacid dehydrogenase superfamily or enzymes belonging to the GRHPR family, of the PPR enzyme, and of proteins of unknown function showing homology to the PPR enzyme, were selected, and a phylogenetic tree was inferred. As a result, the PPR of the present cells was determined to not belong to the existing HPPR or GRHPR family, but to form a new cluster with proteins of unknown function in the ascomycetous yeasts. By doing so, it became clear that PPR forms a new family belonging to the D-isomer specific 2-hydroxyacid dehydrogenase superfamily. This family is situated nearby the HPPR and GRHPR families on the phylogenetic tree, which correlates with the fact that the PPR enzyme, like the enzymes of the HPPR and GRHPR families, recognized phenylpyruvate, 4-hydroxyphenylpyruvate, glyoxalate, and hydroxypyruvate as substrates.

(Functionality of PPR Enzyme)

In the course of the present research, the novel *W. fluorescens* TK1 strain of ascomycetous yeast capable of producing D-3-phenyllactate and optically active 4-hydroxyphenyllactate was discovered. Furthermore, the PPR enzyme, which participates in the production of D-3-phenyllactate and 4-hydroxyphenyllactate, was purified from the test strain, the gene thereof, namely, the pprA gene, was cloned. There has been no report to date of purification of enzymes directly involved in production of 3-phenyllactate and 4-hydroxyphenyllactate, or of cloning of genes thereof, and the present research is the first example of doing so. Moreover, results of both enzymological analysis and molecular phylogenic analysis of DLDH from lactobacilli, which has been reported to be involved in production of 3-phenyllactate, show that the PPR enzyme is a different enzyme. Based on phylogenic analysis, the PPR enzyme has not been classified into any existing family in the D-isomer specific 2-hydroxyacid dehydrogenase superfamily, but was instead mapped to the same group as proteins of unknown function in ascomycetous yeasts. This suggests that the PPR enzyme is a novel enzyme belonging to the D-isomer specific 2-hydroxyacid dehydrogenase superfamily, the functionality of which has been preserved in the ascomycetous yeasts.

A model of the mechanism for synthesis of D-3-phenyllactate in the *W. fluorescens* TK1 strain, which has become clear in the course of the present research, is shown in FIG. 19. It is thought that, in the case of glucose as the carbon source, phenylpyruvate supplied by the shikimate pathway is reduced by the PPR enzyme, forming D-3-phenyllactate. Moreover, in cases in which phenylalanine is added to the culture medium, phenylalanine is converted to phenylpyruvate through elimination of the amino group by aminotransferase. Furthermore, D-3-phenyllactate is formed reductively from phenylpyruvate by the PPR enzyme, with NADPH as a coenzyme. In the presence of phenylalanine, the expression level of the pprA gene at the transcriptional level is increased. Actually, at the protein level as well, PPR activity increased 3.6-fold, and D-3-phenyllactate production levels increased up to 58-fold, when phenylalanine was added, as compared to when it was not added.

Production of 3-phenyllactate in lactobacilli is thought to represent collateral production, as LDH, which converts pyruvate to lactate, has catalytic action on phenylpyruvate, which is a metabolic intermediate of phenylalanine (Valerio, F. et al., (2004) FEMS Microbiol. Letters, 233, 289-295). However, the PPR enzyme of the test strain does not show LDH activity, and of the 2-keto acids recognized to be substrates, affinity is highest for phenylpyruvate. This shows that the functionality of the PPR enzyme is different from that of LDH from ordinary lactobacilli.

It is moreover clear that the PPR enzyme produces D-4-hydroxyphenyllactate from 4-hydroxyphenylpyruvate.

From this it is understood that, in the test strain, production of 3-phenyllactate and 4-hydroxyphenyllactate is not collateral, but rather represents specific production.

In the present research, expression and purification of recombinant PPR through the utilization of a coliform bacteria pET system was successful.

Moreover, in the present research, purification of a novel PPR enzyme involved in biosynthesis of aromatic compounds, cloning of the gene thereof, and construction of an expression system in a different species were successful. This outcome is considered useful in future fermentation production of aromatic compounds. 3-phenyllactate is an antibacterial substance showing a broad spectrum of antibacterial activity, but at the same time has promise as a potential material for aromatic polymers (Tsuji, H. et al., J. Appl. Polymer Sci., 110, 3954-3962 (2008)). The aromatic polymers include phenol resins, typified by Bakelite, and polyphenylene oxide, and generally have outstanding physical properties such as heat resistance and chemical resistance.

However, the supply of starting materials for these has been primarily petroleum derived, and in our current "reduce/reuse/recycle" society, there is a need for a shift to biomass-derived starting materials. To date, the majority of biopolymers being studied for practical application have been polylactates. Polylactates are obtained through lactide polymerization or direct polymerization of lactic acid starting materials (Yin, M.; Baker, G. L., Macromolecules 1999, 32, 7711). The reason why practical application of polylactates is progressing is that the lactic acid starting material is a key product of metabolism, and there is considerable research into biobased production through lactic acid fermentation by lactobacilli. Once fermentation production techniques for aromatic metabolic products are successfully established, it is thought that a consistent supply of starting materials will be possible, making it possible to manufacture biomass-derived aromatic polymers. The present research, through elucidation of the production mechanism of D-3-phenyllactate, is considered to represent a breakthrough for elucidating the functionality of biopolymers employing D-3-phenyllactate, which had proven difficult to do in the research to date.

Example 3

Building a D-3-phenyllactate Production System (1) Preparation of Phenylalanine-Producing Coliform Bacteria into which the PPR Gene is Introduced The D-3-phenyllactate-producing strain was cultured overnight in LB culture medium (10.0 g/L tryptone, 5.0 g/L yeast extract, 10.0 g/L NaCl). Sterile glycerol was then added at a level of 20% of the entire quantity, and it was kept it at −80° C.

For pre-culture, 5.0 mL of LB culture medium was placed in a test tube, and the culture medium was inoculated with a 1/100-fold quantity of the glycerol preservation solution, followed by shake culture for about 6 hours at 37° C., 120 rpm.

First, a plasmid for the ATCC31882 strain, which is a phenylalanine-producing strain (acquired from ATCC), was prepared in accordance with the procedure discussed previously, and employed to introduce the ppr gene and prepare a transformant novel phenyllactate-producing strain.

(2) Culture of Novel Phenyllactate-Producing Strain

The phenyllactate-producing strain was cultured in 50 mL of a phenyllactate production culture medium (Tables 11 and 12) to which 20 g/L of glucose and 50 mg/L of kanamycin were added, by inoculation of a 1/100-fold quantity of the pre-culture broth discussed above, and shake culture for 24 hours at 37° C., 120 rpm, in a 500 mL-capacity vaned conical flask.

TABLE 11

| Phenyllactate production culture medium composition (pH 6.5) | |
|---|---|
| 12.0 g/L | $Na_2HPO_4$ |
| 6.0 g/L | $KH_2PO_4$ |
| 0.50 g/L | NaCl |
| 1.00 g/L | $NH_4Cl$ |
| 0.30 g/L | $MgSO_4 \cdot 7H_2O$ |
| 0.015 g/L | $CaCl_2 \cdot 2H_2O$ |
| 0.015 g/L | Thiamine HCl |
| 10.0 g/L | Tryptone |
| 5.00 g/L | Yeast extract |
| 2.0 ml/L | trace element 2 solution |

TABLE 12

| Trace element 2 solution | |
|---|---|
| 4.00 g | $ZnSO_4 \cdot 7H_2O$ |
| 1.10 g | $H_3BO_3$ |
| 0.50 g | $MnCl \cdot 4H_2O$ |
| 1.00 g/L | $FeSO_4 \cdot 7H_2O$ |
| 0.16 g/L | $CoCl_2 \cdot 6H_2O$ |
| 0.16 g/L | $CuSO_4 \cdot 5H_2O$ |
| 0.11 g/L | $(NH_4)_6Mo_7O_{24} \cdot 4H_2O$ |
| 5.00 g/L | EDTA (2Na) |
| in 100 ml | distilled water |

Figure 20:
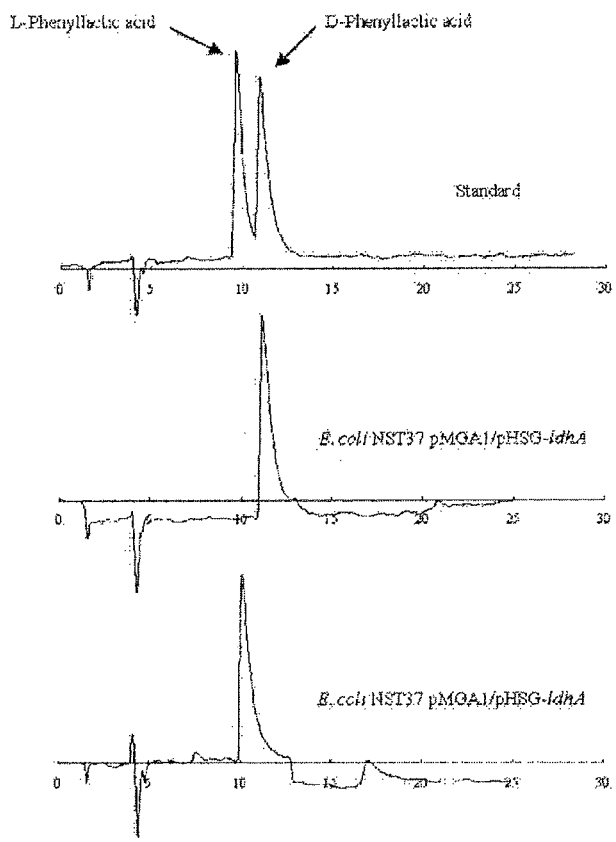
FIG. 20 Shows phenyllactate produced by phenylalanine-producing microorganisms containing the ppr gene.
Figure 21:
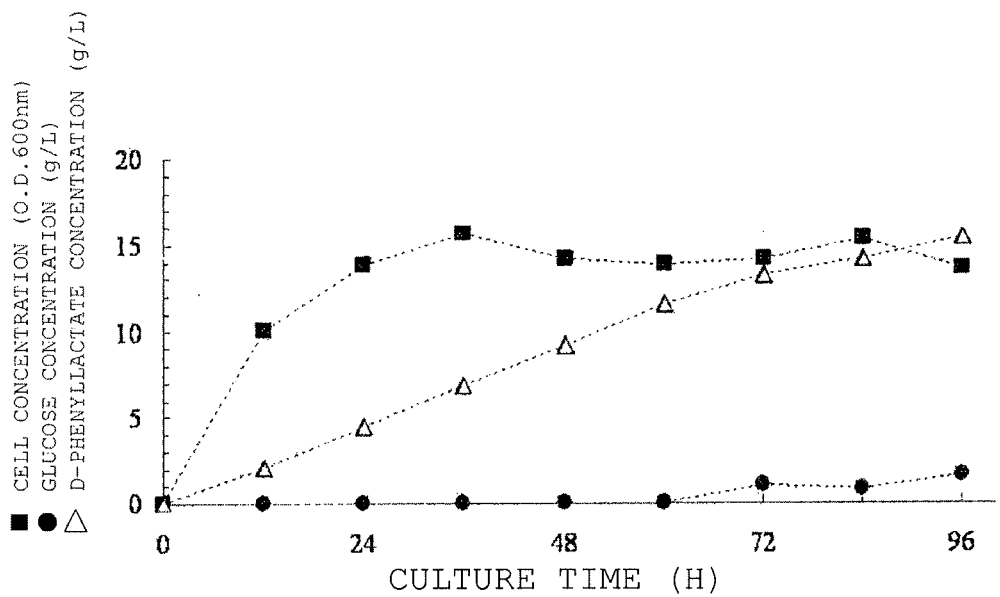
FIG. 21 Shows cell concentration and phenylactate production by phenylalanine-producing microorganism (ATCC31882 strain/pHSGpprA) containing the pprA gene, with D-glucose as the substrate FIG. 22 Shows the expression vector containing the tyrA gene.
Figure 22:
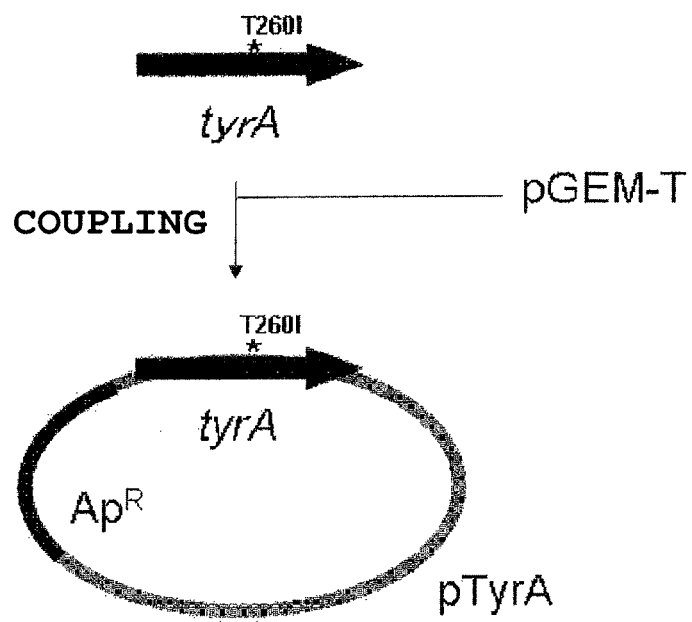

Results are shown in FIG. 20 and Table 13. Quantification of D-3-phenyllactate and L-phenylalanine was performed by HPLC (HEWLETT PACKARD SERIES 1100), employing an RP-18 column (MERCK CORP.).

The optical activity of the phenyllactate was determined by purification of the phenyllactate in the culture medium by a recrystallization process, and running a sample thereof through a NUCLEOSIL Chiral-1 column (MACHEREY-NAGEL CORP.) as described above.

Quantification of D-glucose was performed with a Glucose CII Test Kit (Wako Co. Ltd.)

Through respective introduction of the pprA gene into the phenylalanine-producing strain ATCC31882, a useful strain (ATCC31882/pHSGpprA) respectively producing 99% or more of D-3-phenyllactate was successfully created.

With a view to practical application, production of D-3-phenyllactate was then performed in a jar fermenter, with the ATCC31882 pHSGpprA strain.

400 mL of the aforementioned phenyllactate production culture medium was placed in a 1.0 L-capacity jar fermenter, inoculated with a 1/100-fold quantity of the pre-culture broth discussed above, and cultured for 96 hours at 37° C., 500 rpm under a 0.2 L/min (0.5 vvm) flow of air, and controlling the pH to 7.0 with 5 N NaOh. An appropriate quantity of a defoaming agent was added to stabilize the culture environment.

The D-glucose carbon source was added to the culture medium with a Perista pump, such that the velocity of the 500 g/L glucose solution was 1.50 g/L/h.

The nutrient requirement components L-tyrosine and L-tryptophan were added in advance to the phenyllactate production culture medium in respective amounts of 0.50 g/L, in order to prevent deficiency during prolonged culture.

Ultimately, with culture for 96 hours, 15.5 g/L (10.8% yield vs. sugar) of D-3-phenyllactate was produced. The yield vs. sugar was calculated as the quantity of produced D-3-phenyllactate (g)/total quantity of D-glucose (g).

TABLE 13

| Strain | Cell concentration (O.D.) | Phenyllactate production (g/L) | Phenylalanine production (g/L) | Yield vs. sugar (g-phenyllactate/g-glucose) |
|---|---|---|---|---|
| Escherichia coli K12 | 8.28 | n.d. | 0.30 | |
| ATCC31882 strain | 10.42 | 0.09 | 1.24 | 0.004 |
| ATCC31882/pHSG-pprA | 9.89 | 2.43 | 0.30 | 0.121 |

(4) Purification of Produced D-3-phenyllactate

The D-3-phenyllactate produced in the culture medium was purified by an extraction method employing an organic solvent, and a recrystallization method. A mixed solvent of methanol and hexane (in a 1:1 mixture ratio) was employed as the extraction solvent.

Firstly, hydrochloric acid was added to acidify the culture supernatant from which cells had been removed by centrifugal separation, an equal quantity of extraction solvent was added thereto, stirring gently for 30 minutes to perform the extraction procedure.

Thereafter, the organic solvent layer was recovered, fresh extraction solvent was added again to the culture broth, and the steps discussed above were performed. These steps were performed twice, and the recovered organic solvent layer was evaporated to dryness in an evaporator, obtaining a solid powder containing D-3-phenyllactate.

In order to obtain highly pure D-3-phenyllactate from the solid powder obtained thereby, toluene was added and the powder was thoroughly dissolved at 90-100° C., then slowly cooled to obtain white crystals from the toluene solution.

The toluene was eliminated, and the washed white crystals were run through a chiral column and GC/MS (GC-2010 by SHIMADZU CO. LTD.). As a result, the white crystals were verified to be highly pure D-isomer of 3-phenyllactate.

A technique was thus established whereby fermentation production of optically active 3-D-phenyllactate may be performed employing the PPR of the present invention, to obtain 3-D-phenyllactate in the form of a highly pure product. Moreover, the produced quantity thereof is significantly more than reported in the past, which is beneficial for industrial application in the next section.

Example 4

Building of Optically Active 4-hydroxy-phenyllactate Production System Utilizing Gene Coding for PPR (1) Preparation of L-Tyrosine-Producing Coliform Bacteria into which the PPR Gene is Introduced The optically active 4-hydroxy-phenyllactate-producing strain was cultured overnight in LB culture medium (10.0 g/l tryptone, 5.0 g/L yeast extract, 10.0 g/L NaCl). Sterile glycerol was then added at a level of 20% of the entire quantity, and it was kept it at −80° C.

For pre-culture, 5.0 mL of LB culture medium was placed in a test tube, and the culture medium was inoculated with a 1/100-fold quantity of the glycerol preservation solution, followed by shake culture for about 6 hours at 37° C., 120 rpm.

First, a pTyrA plasmid for the ATCC31882 strain, which is a phenylalanine-producing strain (acquired from ATCC) was prepared in accordance with the procedure discussed previously, and was employed to introduce the tyrA gene (SEQ ID NO 23) in which the C is replaced by T on the $779^{th}$ base of the base sequence shown by SEQ ID NO 24, thereby substituting Ile for the $260^{th}$ Thr, to obtain a L-tyrosine-producing strain. A plasmid (pCWpprA or pHSGpprA) for this L-tyrosine-producing strain was prepared in accordance with the procedure discussed previously, and this was employed to further introduce the ppr gene, to prepare a transformant novel optically active hydroxyphenyllactate-producing strain (NST-pprA producing strain).

(2) Culture of Novel Optically Active Hydroxyphenyllactate-Producing Strain Having PPR The optically active hydroxyphenyllactate-producing strain having PPR was cultured in 50 mL of a D-hydroxyphenyllactate production culture medium (Tables 14 and 15) to which 20 g/L of glucose and 50 mg/L of kanamycin were added, by inoculation of a 1/100-fold quantity of the pre-culture broth discussed above, and shake culture for 24 hours at 37° C., 120 rpm, in a 500 mL-capacity vaned conical flask.

When the obtained transformant was cultured in a culture medium containing glucose as the carbon source, 4-hydroxyphenyllactate was detected in the culture medium. The produced 4-hydroxyphenyllactate was D-4-hydroxyphenyllactate. To date, fermentation production of 2.5 g/L D-4-hydroxyphenyllactate (8% yield vs. sugar) has been possible (Table 16).

TABLE 14

4-Hydroxyphenyllactate production culture medium composition (pH 6.5)

| | |
|---|---|
| 12.0 g/L | Na$_2$HPO$_4$ |
| 6.0 g/L | KH$_2$PO$_4$ |
| 0.50 g/L | NaCl |
| 1.00 g/L | NH$_4$Cl |
| 0.30 g/L | MgSO$_4$•7H$_2$O |
| 0.015 g/L | CaCl$_2$•2H$_2$O |
| 0.015 g/L | Thiamine HCl |
| 10.0 g/L | Tryptone |
| 5.00 g/L | Yeast extract |
| 2.0 ml/L | trace element 2 solution |

TABLE 15

Trace element 2 solution

| | |
|---|---|
| 4.00 g | ZnSO$_4$•7H$_2$O |
| 1.10 g | H$_3$BO$_3$ |
| 0.50 g | MnCl•4H$_2$O |
| 1.00 g/L | FeSO$_4$•7H$_2$O |
| 0.16 g/L | CoCl$_2$•6H$_2$O |
| 0.16 g/L | CuSO$_4$•5H$_2$O |
| 0.11 g/L | (NH$_4$)$_6$Mo$_7$O$_{24}$•4H$_2$O |
| 5.00 g/L | EDTA (2Na) |
| in 100 ml | distilled water |

TABLE 16

| Strain | Cell concentration (O.D.) | D-hydroxyphenyl-lactate production (g/L) | Yield vs. sugar (g-hydroxy-phenyllactate/g-glucose) |
|---|---|---|---|
| *Escherichia coli* K12 | 6.1 | n.d. | |
| ATCC31882 strain/pTyrA | 6.0 | n.d. | |
| ATCC31882/pTyrA/pHSGpprA | 5.4 | 2.5 | 0.08 |

(3) Purification of Optically Active 4-hydroxy-phenyllactate Produced by Microorganism Containing Gene Coding for PPR The D-4-hydroxyphenyllactate produced in the culture medium was purified by an extraction method employing an organic solvent, and a recrystallization method. A mixed solvent of methanol and hexane (in a 1:1 mixture ratio) was employed as the extraction solvent.

Firstly, hydrochloric acid was added to acidify (to pH 2.5-3.5) the culture supernatant from which cells had been removed by centrifugal separation, an equal quantity of extraction solvent was added thereto, stirring gently for 30 minutes to perform the extraction procedure.

Thereafter, the organic solvent layer was recovered, fresh extraction solvent was added again to the culture broth, and the steps discussed above were performed. The recovered organic solvent layer was evaporated to dryness in an evaporator, obtaining a solid powder containing D-4-hydroxyphenyllactate.

In order to obtain highly pure D-4-hydroxyphenyllactate from the solid powder obtained thereby, toluene was added and the powder was thoroughly dissolved at 90-100° C., then slowly cooled to obtain white crystals from the toluene solution.

Figure 23:
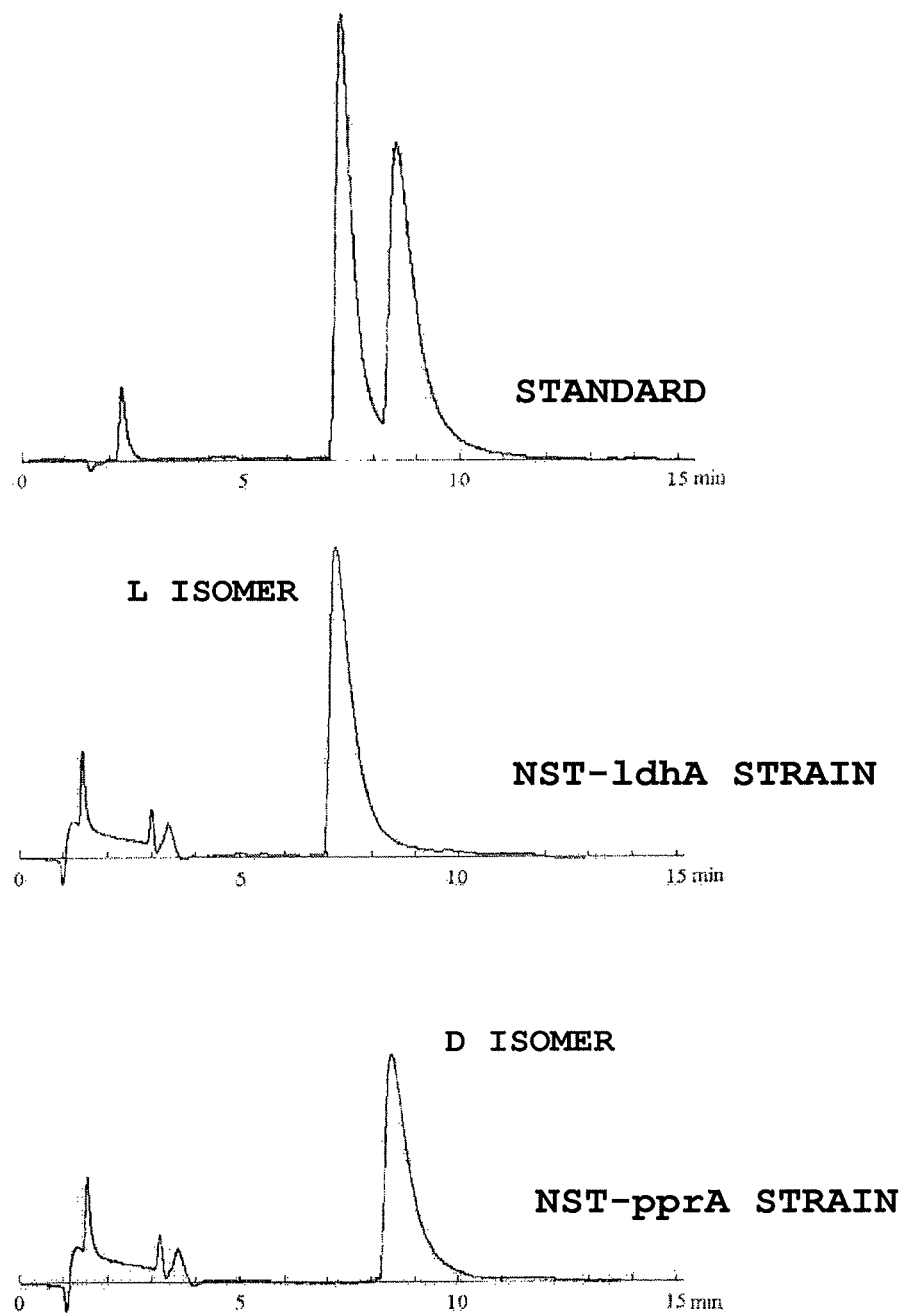
FIG. 23 HPLC analysis of 4-hydroxyphenyllactate. Standard; D,L-4-hydroxyphenyllactate (left: L-4-hydroxyphenyllactate/right: D-4-hydroxyphenyllactate); L-4-hydroxyphenyllactate from NST-ldhA strain; D-4-hydroxyphenyllactate produced by NST-pprA strain.

The toluene was eliminated, and the washed white crystals were run through a chiral column and GC/MS (GC-2010 by SHIMADZU CO. LTD.), as a result of which the white crystals were verified to be highly pure D-4-hydroxyphenyllactate (approximately 99% pure) (see FIG. 23).

Example 5

Fermentation Production of D-4-hydroxyphenyllactate Utilizing *W. Fluorescens* TK1 Strain of Yeast It was shown that the strain is capable of converting tyrosine added to the culture medium into 4-hydroxyphenyllactate. It is thought that the strain produces 4-hydroxyphenyllactate from glucose starting material, through the shikimate pathway via 4-hydroxyphenylpyruvate. The 4-hydroxyphenyllactate produced is the optically active isomer (D-4-hydroxyphenyllactate).

(Quantification of 4-hydroxyphenyllactate by High-Performance Liquid Chromatography (HPLC))

Using HPLC, quantification of hydroxyphenyllactate in samples was performed through analysis under the following conditions.

In the case of analysis of a culture broth, the culture medium supernatant from which cells were removed by filtration, centrifugal separation, or the like is used as the sample.

Analyzer: HP-1100 (Hewlett-Packard)
Column: TSKgel ODS-80™ (4.6×150 mm, Tosoh, Tokyo, Japan)
Column temperature: 28° C.
Flow velocity: 0.8 mL/min
Mobile phase: 20 mm potassium phosphate buffer (pH 2.5): methanol (6:4, v/v)

(Qualification of 4-hydroxyphenyllactate by Gas Chromatography-Mass Spectrometer (GC/MS))

5 mL of the culture broth, adjusted from pH 9 to 10 with 1% NaOH, was reduced-pressure dried in a centrifugal evaporator. The precipitate obtained thereby was completely suspended in 200 µL of 1% NaOH, 167 µL of methanol, and 34 µL of pyridine. To this was added 20 µL of methyl chlorocarbonate, stirring vigorously to methylate the specimen. After repeating the operation of adding methyl chlorocarbonate and stirring, 400 µL of chloroform was added and stirred. Next, 50 mM of sodium bicarbonate was added, and after stirring, the aqueous layer was removed. The chloroform layer obtained thereby was completely dehydrated by adding 0.1 g of sodium sulfate to the chloroform layer thusly obtained, and the organic acids contained in the solution thusly obtained were measured by GC/MS (GCMS-QP2010 Plus by Shimadzu). Conditions for the analysis were as follows.

Analyzer: GC/MS-QP2010 Plus (Shimadzu)
Column: DB-5 (0.32 mm×30 m)
Column temperature: 60° C. (2 min)–8° C./min–180° C. (5 min)–40° C./min–220° C. (5 min)
Interface temperature: 230° C.
Ion source temperature: 250° C.
Carrier gas: He
Flow rate: 30 mL/min (Optical isomerism of produced D-4-hydroxyphenyllactate)
(Chiral analysis employing HPLC)

The optical isomerism of D-4-hydroxyphenyllactate in the culture broth was determined employing HPLC, under the following analysis conditions. The culture supernatant from which cells were removed from the culture broth by filtration, centrifugal separation, or the like is used as the sample.

Analyzer: HP-1100 (Hewlett-Packard)
Column: Nucleosil Chiral-1 (Macherey-Nagel)
Column temperature: 60° C.
Flow velocity: 1.2 mL/min
Mobile phase: 0.5 mM CuSO$_4$ (Optical Isomerism of Produced 4-hydroxyphenyllactate)

The culture supernatant was recovered and appropriately diluted with methanol to obtain a sample for analysis. Measurement of hydroxyphenyllactate concentration was determined employing HPLC, under the following analysis conditions.

Analyzer: HP-1100 (Hewlett-Packard)
Column: ODS-column (5C18-MS-II: COSMSIL)
Column temperature: 28° C.
Flow velocity: 0.8 mL/min
Mobile phase: 20 mM phosphoric acid:methanol=4:6

Utilizing the PPR enzyme of the present invention, it is possible to convert tyrosine to D-4-hydroxyphenyllactate. Furthermore, by utilizing a transformant such that production occurs via the shikimate pathway and hydroxyphenylpyruvate, it is possible to produce D-4-hydroxyphenyllactate from glucose starting material.

Moreover, utilizing the PPR of the present invention and the gene that codes for it, selective formation of D-4-hydroxyphenyllactate is possible.

Therefore, a technique has been established whereby fermentation production of D-phenyllactate and D-4-hydroxyphenyllactate may be performed to obtain D-phenyllactate and D-4-hydroxyphenyllactate in the form of highly pure products. Moreover, the produced quantity thereof is significantly more than reported in the past, which is beneficial for industrial application in the next section.

INDUSTRIAL APPLICABILITY

According to the present invention there are obtained PPR and the pprA gene coding for the same, whereby it is possible for highly pure, optically active 3-phenyllactate and 4-hydroxyphenyllactate to be obtained efficiently from a uniquely discovered novel D-3-phenyllactate-producing strain. Through formation of a transformant into which the pprA gene is inserted, highly pure, optically active 3-phenyllactic acid and 4-hydroxyphenyllactate may be obtained efficiently from inexpensive glucose starting material, making possible manufacture though genetic engineering as well.

This optically active 3-phenyllactate is of interest in a wide range of fields and shows promise for utilization, for example, in polyaromatic based plastic starting materials, biocompatible materials, functional materials, and pharmaceutical or agricultural intermediates. Likewise, optically active 4-hydroxyphenyllactate shows promise for utilization as food additives, pharmaceuticals, agricultural chemicals, and the like. Furthermore, [these compounds] have the possibility of representing a breakthrough for building fermentation production techniques for aromatic compounds, which has been considered difficult in the past.

The invention claimed is:

1. A method of producing D phenyllactate or D-4-hydroxyphenyllactate, comprising
    transforming a microorganism with a recombinant vector containing
    a complementary polynucleotide coding for an amino acid sequence having at least 90% identity to an amino acid sequence shown by SEQ ID NO: 4,
    culturing the transformed microorganism with a substrate, and
    recovering D-phenyllactate or D-4-hydroxyphenyllactate from a microorganism culture.

2. The method according to claim 1 wherein the microorganism is coliform bacteria or a phenylalanine- or tyrosine-producing recombinant microorganism.

3. The method according to claim 1, wherein the substrate is one or more substrates selected from D-glucose, L-phenylalanine, L-tyrosine, phenylpyruvate, and 4-hydroxyphenylpyruvate.

4. A microorganism designated as *Wickerhamia fluorescens* TK1, and deposited with the Patent Organism Depository (IPOD) of National Institute of Advanced Industrial Science and Technology under Accession No. FERM BP-11466.

5. The method according to claim 1, wherein the method comprises recovering the D-phenyllactate.

6. The method according to claim 1, wherein the method comprises recovering the D-4-hydroxyphynyllactate.

7. The method according to claim 1, wherein the complementary polynucleotide codes for an amino acid sequence comprising the amino acid sequence of SEQ ID NO: 4.

8. The method according to claim 1, wherein the complementary polynucleotide codes for an amino acid sequence consisting of the amino acid sequence of SEQ ID NO: 4.

* * * * *